United States Patent [19]
Russo-Rodriguez et al.

[11] Patent Number: 6,107,291
[45] Date of Patent: Aug. 22, 2000

[54] AZEPINE OR LARGER MEDIUM RING DERIVATIVES AND METHODS OF USE

[75] Inventors: Sandra E. Russo-Rodriguez, Superior; Kevin Koch, Boulder, both of Colo.; Andreas Termin, Encinitas, Calif.; Conrad Hummel, Louisville, Colo.

[73] Assignee: Amgen Inc., Thousand Oaks, Calif.

[21] Appl. No.: 09/213,077

[22] Filed: Dec. 16, 1998

Related U.S. Application Data

[60] Provisional application No. 60/068,227, Dec. 19, 1997.

[51] Int. Cl.⁷ .................. A61K 31/40; C07D 487/04; C07D 223/02
[52] U.S. Cl. ................. 514/212; 514/211; 540/484; 540/596; 540/604
[58] Field of Search .................... 514/211, 212; 540/484, 604, 596

[56] References Cited

U.S. PATENT DOCUMENTS 5,552,419  9/1996  MacPherson ................... 514/357

FOREIGN PATENT DOCUMENTS

| 039051 | of 0000 | European Pat. Off. . |
| 606046 | of 0000 | European Pat. Off. . |
| 803505 | of 0000 | European Pat. Off. . |
| WO 96/33172 | of 0000 | WIPO . |
| WO 97/05865 | of 0000 | WIPO . |
| WO 97/18194 | of 0000 | WIPO . |
| WO 98/08827 | of 0000 | WIPO . |

OTHER PUBLICATIONS

Reich et al., J. Amer. Chem. Soc., 97:19, p. 5434 (1975).
Svensson et al., Drug Metabolism Reviews, 19(2), 165–194 (1988).
Bundgaard, J. Med. Chem., 32(12), 2503 (1989).
Baldwin et al., Tetrahedron, 45(19), 6309 (1989).
Schuster et al., Angew. Chem. Int. Ed. Engel, 36:2036–2056 (1997).
Ninomiya et al., Tetrahedron, 30:2151 (1974).
Wadsworth, Organic Reactions, 25:73–253 (1977).
Rabjohn, Organic Reactions, 24:261–415 (1976).
Posner, Organic Reactions, 19:1–113 (1972).
Gearing et al., Nature, 370:555–557 (1994).
Mohler et al., Nature, 370:218–220 (1994).
Shohami et al., J. Cereb. Blood Flow Metab., 14:615–619 (1994).
Lahdevirta et al., The American J. Med., 85:289 (1988).
Clouse et al., J. Immunol., 142:431–438 (1989).
Maini et al., Immunological Reviews, No. 144, pp. 195–223 (1995).
McGeehan et al., Nature, 370:558–561 (1994).
Liu et al., Neuroscience Letters, 164:125–128 (1993).
Liu et al., Stroke, 25:1481–1488 (1994).

*Primary Examiner*—Mukund J. Shah
*Assistant Examiner*—Pavanaram K Sripada
*Attorney, Agent, or Firm*—Frank Ungemach; Steven M. Odre

[57] ABSTRACT

Selected novel azepine and larger medium ring compounds are effective for prophylaxis and treatment of inflammation, tissue degradation and related diseases. The invention encompasses novel compounds, analogs, prodrugs and pharmaceutically acceptable salts thereof, pharmaceutical compositions and methods for prophylaxis and treatment of inflamation, tissue degradation and related diseases. The subject invention also relates to processes for making such compounds as well as to intermediates useful in such processes.

25 Claims, No Drawings

AZEPINE OR LARGER MEDIUM RING DERIVATIVES AND METHODS OF USE

This application claims priority of Provisional Application No. 60/068,227, Dec. 19, 1997.

BACKGROUND OF THE INVENTION

The present invention relates to metalloproteinase inhibitors and, more particularly, relates to novel compounds, compositions and methods for prophylaxis and treatment of inflammation, tissue degradation and the like. This invention, in particular, relates to novel azepine and larger medium ring compounds, compositions containing such compounds and methods of use of such compounds. The subject invention also relates to processes for making such compounds as well as to intermediates useful in such processes.

Metalloproteinase enzymes, such as collagenases, stromelysins, gelatinases and TNF convertase, may contribute to the onset or etiology of, or exacerbate disease states which are related to, connective tissue degradation, secretion of proinflammatory cytokines and the like. For example, matrix metalloproteinases, such as collagenases, stromelysins and gelatinases, are thought to be involved in the tissue breakdown observed in rheumatoid arthritis; osteoarthritis; osteopenias (e.g., osteoporosis); periodontitis; gingivitis; corneal, epidermal and gastric ulceration; and tumour metastasis, invasion and growth; in neuroinflammatory disorders, such as myelin degradation (e.g., multiple sclerosis); and in angiogenesis dependent diseases, such as arthritic conditions; cancer; solid tumor growth; psoriasis; proliferative retinopathies; neovascular glaucoma; ocular tumours; angiofibromas; hemangiomas; nephritis; pulmonary inflammation; and restenosis.

Tumor Necrosis Factor alpha (TNF-α) is a proinflammatory cytokine secreted by a variety of cells including monocytes and macrophages in response to many inflammatory stimuli (e.g., lipopolysaccharide—LPS) or external cellular stress (e.g., osmotic shock, peroxide). Elevated levels of TNF play a major role in mediating many inflammatory disease states. Elevated levels of TNF-α may contribute to the onset, etiology, or exacerbate the following disease states: rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those viruses sensitive to TNF-α inhibition—HIV-1, HIV-2, HIV-3, cytomegalovirus (CMV), influenza, adenovirus, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; and fever and mylagias due to infection.

Several approaches have been taken to block the effects of TNF-α. One approach involves utilizing soluble receptors for TNF-α (e.g., TNFR-55 or TNFR-75) which have demonstrated efficacy in animal models of TNF-α mediated disease states. A second approach to neutralizing TNF-α utilizing a monoclonal antibody specific to TNF-α, cA2, has demonstrated improvement in swollen joint count in a Phase II human trial of rheumatoid arthritis (Feldmann et al., Immunological Reviews p.195–223 (1995)).

The above approaches block the effects of TNF-α by either protein sequesterization or receptor antagonism, but an additional approach to blockade is to intervene in the cellular secretion of TNF. TNF convertase is thought to be a metalloproteinase enzyme involved in the cellular secretion of TNF-α (Mohler et al., Nature 370:218–220, 1994; Gearing et al., Nature 370:555–557, 1994; McGeehan et al., Nature 370:558–561, 1994). Inhibition of TNF convertase is thought to be an additional approach to intervene in the cellular secretion of TNF-α. For example, a metalloproteinase inhibitor was shown to inhibit cellular secretion of TNF-α, in vitro and in vivo, which was thought to be due to inhibition of TNF convertase (McGeehan et al., Nature 370:558–561, 1994). While evidence as to the nature of intervention by metalloproteinase inhibitors in the cellular secretion of TNF-α exists, additional or alternative mechanisms of action by which such compounds inhibit TNF secretion may be involved, such as by intervening at a point on the pathway between extracellular stimulus and secretion of protein.

Since TNF-α is upstream in the cytokine cascade of inflammation wherein elevated levels of TNF-α lead to elevated levels of other cytokines including IL-1, IL-6 and IL-8, inhibiting the secretion of TNF-α may also reduce levels of other cytokines including but not limited to IL-1, IL-6 or IL-8.

Further, TNF-α is thought to play a role in head trauma, stroke and ischemia. For instance, in animal models of head trauma (rat), TNF-α levels increased in the contused hemisphere (Shohami et al., J. Cereb. Blood Flow Metab. 14:615–619 (1994)). In a model of ischemia wherein the middle cerebral artery was occluded in rats, the levels of mRNA of TNF-α increased (Feurstein et al., Neurosci. Lett. 164:125–128 (1993)). Administration of TNF-α into the rat cortex resulted in significant PMN accumulation in capillaries and adherance in small blood vessels. The TNF-α promotes the infiltration of other cytokines (IL-1b, IL-6) and also chemokines, which promote neutrophil infiltration into the infarct area (Feurstein Stroke 25:1481–1488 (1994)).

TNF-α also may play a role in promoting certain viral life cycles and disease states associated with them. For instance, TNF-α secreted by monocytes induced elevated levels of HIV expression in a chronically infected T cell clone (Clouse et al., J. Immunol. 142:431 (1989)). The role of TNF-α in the HIV associated states of cachexia and muscle degradation has been discussed (Lahdevirta et al., The American J. Med. 85:289 (1988)).

WO 96/33172 discloses N-arylsulfonyl and N-heteroarylsulfonyl substituted 6 membered ring heterocycle hydroxamic acid derivatives, such as N-arylsulfonyl- and N-heteroarylsulfonyl-piperidinyl-2-hydroxamic acid compounds, and their preparation and use as inhibitors of matrix metalloproteinases and TNF production.

EP 606046 discloses N-arylsulfonyl and N-heteroarylsulfonyl substituted 5–6 membered ring heterocycle hydroxamic acid derivatives, such as N-arylsulfonyl- and N-heteroarylsulfonyl-piperidinyl-2-hydroxamic acid compounds and N-arylsulfonyl- and N-heteroarylsulfonyl-1,2,3,4-tetrahydroisoquinolinyl-2-hydroxamic acid compounds, preparation and use as inhibitors of matrix metalloproteinases.

WO 97/18194 discloses certain cyclic and heterocyclic N-substituted α-substituted iminohydroxamic and carboxylic acids, and their preparation and use as inhibitors of matrix metalloproteinases.

EP 803505 discloses optionally substituted aryl fused N-heterocycles and their preparation and use as inhibitors of metalloproteinases.

BRIEF DESCRIPTION OF THE INVENTION

The present invention relates to selected metalloproteinase inhibitory compounds, analogs and pharmaceutically acceptable salts and prodrugs thereof. The subject compounds are characterized as azepine and larger medium ring compounds. The compounds are useful in the prophylaxis and treatment of inflammation, tissue degradation and related diseases. Therefore, this invention also encompasses pharmaceutical compositions and methods for prophylaxis and treatment of inflamation, tissue degradation and related diseases. The subject invention also relates to processes for making such compounds, as well as to intermediates useful in such processes.

DETAILED DESCRIPTION OF THE INVENTION

In accordance with the present invention, there is provided a compound of the Formula I below:

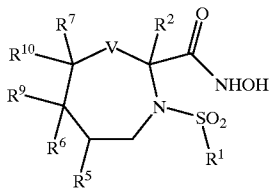

(I)

or a pharmacutically acceptable salt thereof, wherein $R^1$ is (1) an alkyl, alkenyl, alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$_3$, —S(O)R$^3$, —S(O)$_2$R$^3$, —C(O)R$^3$, —NR$^3$R$^4$, amino, alkanoylamino, alkylsulfonylamino, alkoxycarbonylamino, alkoxycarbonyl, cyano, halo, azido, alkyl or haloalkyl;

preferably, $R^1$ is (1) an $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH , —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, $C_1$–$C_8$ alkanoyl amino, $C_1$–$C_8$ alkylsulfonylamino, $C_1$–$C_8$ alkoxycarbonyl amino, $C_1$–$C_8$ alkoxycarbonyl, cyano, halo, azido, $C_1$–$C_8$ alkyl or $C_1$–$C_8$ haloalkyl of 1–3 halo radicals;

more preferably, $R^1$ is (1) a $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, $C_1$–$C_4$ alkanoylamino, $C_1$–$C_4$ alkylsulfonylamino, $C_1$–$C_4$ alkoxy carbonylamino, $C_1$–$C_4$ alkoxycarbonyl, cyano, halo, azido, $C_1$–$C_6$ alkyl or $C_1$–$C_4$ haloalkyl of 1–3 halo radicals;

more preferably, $R^1$ is (1) a $C_1$–$C_{12}$ alkyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —CF$_3$ radicals;

more preferably, $R^1$ is (1) an $C_1$–$C_{12}$ alkyl radical optionally substituted by 1–3 radicals of —OH, —OR$^3$, —SR$^3$, —S(O)$_2$R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —CF$_3$ radicals;

more preferably, $R^1$ is (1) an $C_1$–$C_4$ alkyl radical substituted by 1–2 radicals of —OH, —OR$^3$, —NR$^3$R$^4$, aryl or heteroaryl; or (2) an aryl radical optionally substituted by a monocyclic heteroaryl radical of 5–6 ring members; or (3) a heteroaryl radical optionally substituted by a phenyl radical; wherein the phenyl, aryl and heteroaryl radicals of (1), (2) and (3) are optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals;

more preferably, $R^1$ is aryl or heteroaryl radicals optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals; and more preferably, $R^1$ is an aryl radical optionally substituted by 1–2 radicals of hydroxy, —OR$^3$, —S(O)$_2$R$^3$, —NR$^3$R$^4$, amino, acetylamino, methylsulfonylamino, halo, $C_1$–$C_4$ alkyl or —CF$_3$ radicals;

more preferably, $R^1$ is an phenyl radical optionally substituted by 1–2 radicals of hydroxy, —OR$^3$, —S(O)$_2$R$^3$, —NR$^3$R$^4$, amino, acetylamino, methylsulfonylamino, halo, $C_1$–$C_4$ alkyl or —CF$_3$ radicals;

most preferably, $R^1$ is an phenyl radical optionally substituted by 1–2 radicals of hydroxy, —OR$^3$, halo, methyl or —CF$_3$ radicals; and provided that the total number of phenyl, aryl, heteroaryl, cycloalkyl and heterocyclyl radicals in $R^1$ is preferably 0–3, more preferably, 0–2, most preferably, 1–2;

wherein each $R^3$ is independently an alkyl, haloalkyl, aryl, heteroaryl, aryl-alkyl or heteroaryl-alkyl radical, wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each $R^3$ is independently a $C_1$–$C_8$ alkyl, $C_1$–$C_8$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals;

more preferably, each $R^3$ is independently a $C_1$–$C_4$ alkyl, $C_1$–$C_4$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^3$ is independently an $C_1$–$C_4$ alkyl, —CF$_3$, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —CF$_3$ or —OCF$_3$;

more preferably, each $R^3$ is independently a $C_1$–$C_4$ alkyl, —CF$_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —CF$_3$ or —OCF$_3$;

more preferably, each $R^3$ is independently a $C_1$–$C_4$ alkyl, —CF$_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_2$ alkoxy, $C_1$–$C_2$ alkylthiol, amino, acetylamino, methylsulfonylamino, $C_1$–$C_2$ alkylsulfonyl, $C_1$–$C_4$ alkoxycarbonylamino, $C_1$–$C_4$ alkoxycarbonyl, halo, $C_1$–$C_2$ alkyl, —CF$_3$ or —OCF$_3$;

more preferably, each $R^3$ is independently a $C_1$–$C_4$ alkyl, —CF$_3$, aryl, heteroaryl, arylmethyl or heteroarylmethyl radical;

more preferably, each $R^3$ is independently an $C_1$–$C_4$ alkyl, —CF$_3$, phenyl, heteroaryl, phenylmethyl or heteroarylmethyl radical;

most preferably, each $R^3$ is independently an methyl, —CF$_3$, phenyl, heteroaryl, phenylmethyl or heteroarylmethyl radical; and each $R^4$ is independently a hydrogen or alkyl radical; preferably, each $R^4$ is independently a hydrogen or $C_1$–$C_8$ alkyl radical; more preferably, each $R^4$ is independently a hydrogen or $C_1$–$C_4$ alkyl radical; most preferably, each $R^4$ is independently a hydrogen or methyl radical; and $R^2$ is a hydrogen or alkyl radical; preferably, $R^2$ is a hydrogen or $C_1$–$C_4$ alkyl radical; more preferably, $R^2$ is a hydrogen or methyl radical; and most preferably, $R^2$ is a hydrogen radical; and V is —CR$^8$R$^{11}$— or —CR$^8$R$^{11}$—CHR$^{12}$—; preferably, V is —CR$^8$R$^{11}$—; alternatively, preferably, V is —CR$^8$R$^{11}$—CHR$^{12}$—;

wherein $R^{11}$ and $R^{12}$ are each independently (1) a hydrogen, —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, cycloalkyl, aryl or heteroaryl radical; or (2) an alkyl, alkenyl or alkynyl radical optionally substituted with 1–3 radicals of —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, aryl or heteroaryl; wherein the cycloalkyl, aryl and heteroaryl radicals of (1) and (2) are optionally substituted by 1–3 radicals of hydroxy, alkoxy, alkylthiol, amino, alkanoylamino, alkylsulfonylamino, alkoxycarbonylamino, alkoxycarbonyl, cyano, halo, azido, alkyl, haloalkyl or haloalkoxy;

preferably, $R^{11}$ and $R^{12}$ are each independently (1) a hydrogen, —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, cycloalkyl, aryl or heteroaryl radical; or (2)

an $C_1$–$C_8$ alkyl, $C_2$–$C_8$ alkenyl or $C_2$–$C_8$ alkynyl radical optionally substituted with 1–3 radicals of —$OR^{20}$, —$SR^{21}$, —$C(O)R^{22}$, —$NR^{33}$—$C(O)$—$R^{31}$—$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals;

more preferably, $R^{11}$ and $R^{12}$ are each independently (1) a hydrogen, —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_8$ alkyl, $C_2$–$C_8$ alkenyl or $C_2$–$C_8$ alkynyl radical optionally substituted with 1–3 radicals of —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, $R^{11}$ and $R^{12}$ are each independently (1) a hydrogen, —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_4$ alkyl, $C_2$–$C_4$ alkenyl or $C_2$–$C_4$ alkynyl radical optionally substituted with 1–3 radicals of —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–3 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals;

more preferably, $R^{11}$ and $R^{12}$ are each independently (1) a hydrogen, —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_4$ alkyl, $C_2$–$C_4$ alkenyl radical optionally substituted with 1–3 radicals of —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–2 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals;

more preferably, $R^{11}$ and $R^{12}$ are each independently (1) a hydrogen, —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_4$ alkyl or $C_2$–$C_4$ alkenyl radical optionally substituted with 1–3 radicals of —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–2 radicals of hydroxy, $C_1$–$C_4$ alkoxy, $C_1$–$C_4$ alkylthiol, methylsulfonyl, halo, azido, $C_1$–$C_4$ alkyl, —$CF_3$ or —$OCF_3$ radicals;

more preferably, $R^{11}$ and $R^{12}$ are each independently (1) a hydrogen, —$OR^{20}$, —$NR^{33}$—$C(O)$—$R^{31}$, —$NR^{33}$—$S(O)_2$—$R^{30}$, cycloalkyl, aryl or heteroaryl radical; or (2) an $C_1$–$C_4$ alkyl or $C_2$–$C_4$ alkenyl radical optionally substituted with 1–2 radicals of —$OR^{20}$, —$SR^{21}$, —$C(O)R^{22}$, —$NR^{33}$—$C(O)$—$R^{31}$, —$NR^{33}$—$S(O)_2$—$R^{30}$, aryl or heteroaryl; wherein the cycloalkyl, aryl and heteroaryl radicals of (1) and (2) are optionally substituted by 1–2 radicals of hydroxy, $C_1$–$C_2$ alkoxy, $C_1$–$C_2$ alkylthiol, halo, azido, $C_1$–$C_2$ alkyl, —$CF_3$ or —$OCF_3$ radicals;

more preferably, $R^{11}$ and $R^{12}$ are each independently (1) a hydrogen, —$OR^{20}$, —$NR^{33}$—$C(O)$—$R^{31}$, —$NR^{33}$—$S(O)_2$—$R^{30}$, cycloalkyl, aryl or heteroaryl radical; or (2) an $C_1$–$C_4$ alkyl or $C_2$–$C_4$ alkenyl radical optionally substituted with 1–2 radicals of —$OR^{20}$, —$NR^{33}$—$C(O)$—$R^{31}$, —$NR^{33}$—$S(O)_2$—$R^{30}$, aryl or heteroaryl; wherein the cycloalkyl, aryl and heteroaryl radicals of (1) and (2) are optionally substituted by 1–2 radicals of hydroxy, $C_1$–$C_2$ alkoxy, $C_1$–$C_2$ alkylthiol, halo, azido, $C_1$–$C_2$ alkyl, —$CF_3$ or —$OCF_3$ radicals;

more preferably, $R^{11}$ and $R^{12}$ are each independently (1) a hydrogen, —$OR^{20}$, aryl or heteroaryl radical; or (2) an $C_1$–$C_4$ alkyl or $C_2$–$C_4$ alkenyl radical optionally substituted with 1–2 radicals of —$OR^{20}$, aryl or heteroaryl; wherein the aryl and heteroaryl radicals of (1) and (2) are optionally substituted by 1–2 radicals of hydroxy, $C_1$–$C_2$ alkoxy, halo, $C_1$–$C_2$ alkyl, —$CF_3$ or —$OCF_3$ radicals;

more preferably, $R^{11}$ and $R^{12}$ are each independently (1) a hydrogen, —$OR^{20}$, phenyl or heteroaryl radical; or (2) an $C_1$–$C_4$ alkyl or $C_2$–$C_4$ alkenyl radical optionally substituted with 1–2 radicals of —$OR^{20}$, phenyl or heteroaryl; wherein the phenyl and heteroaryl radicals of (1) and (2) are optionally substituted by 1–2 radicals of hydroxy, $C_1$–$C_2$ alkoxy, halo, $C_1$–$C_2$ alkyl, —$CF_3$ or —$OCF_3$ radicals; and most preferably, $R^{11}$ and $R^{12}$ are each independently (1) a hydrogen, —$OR^{20}$, phenyl or heteroaryl radical; or (2) an $C_1$–$C_4$ alkyl or $C_2$–$C_4$ alkenyl radical optionally substituted with 1–2 radicals of —$OR^{20}$, phenyl or heteroaryl; wherein the phenyl and heteroaryl radicals of (1) and (2) are optionally substituted by 1–2 radicals of hydroxy, methoxy, halo, methyl, —$CF_3$ or —$OCF_3$ radicals;

more preferably, when V is —$CHR^{11}$—$CHR^{12}$—, one of $R^{11}$ and $R^{12}$ is a hydrogen, hydroxy, $C_1$–$C_4$ alkoxy or $C_1$–$C_4$ alkyl radical and the other is as described above for $R^{11}$ and $R^{12}$;

wherein each $R^{20}$ is independently a hydrogen, alkyl, alkenyl, aryl, heteroaryl, aryl-alkyl, heteroaryl-alkyl, alkanoyl, aroyl or heteroaroyl radical; wherein the alkyl and alkenyl radicals are optionally substituted by —C(O)R$^{22}$; and wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each R$^{20}$ is independently a hydrogen, C$_1$–C$_8$ alkyl, C$_2$–C$_8$ alkenyl, aryl, heteroaryl, aryl-C$_1$–C$_4$-alkyl, heteroaryl-C$_1$–C$_4$-alkyl, C$_1$–C$_8$ alkanoyl, aroyl or heteroaroyl radical; wherein the alkyl and alkenyl radicals are optionally substituted by —C(O)R$^{22}$; and wherein the aryl and heteroaryl radicals are optionally substituted by 1–3 radicals of hydroxy, C$_1$–C$_4$ alkoxy, C$_1$–C$_4$ alkylthiol, amino, C$_1$–C$_8$ alkanoylamino, C$_1$–C$_8$ alkylsulfonylamino, C$_1$–C$_4$ alkylsulfinyl, C$_1$–C$_4$ alkylsulfonyl, C$_1$–C$_8$ alkoxycarbonylamino, C$_1$–C$_8$ alkoxycarbonyl, cyano, halo, azido, C$_1$–C$_8$ alkyl, C$_1$–C$_8$ haloalkyl of 1–3 halo radicals or C$_1$–C$_8$ haloalkoxy of 1–3 halo radicals;

more preferably, each R$^{20}$ is independently a hydrogen, C$_1$–C$_4$ alkyl, C$_2$–C$_4$ alkenyl, aryl, heteroaryl, aryl-C$_1$–C$_4$-alkyl, heteroaryl-C$_1$–C$_4$-alkyl, C$_1$–C$_4$ alkanoyl, aroyl or heteroaroyl radical; wherein the alkyl and alkenyl radicals are optionally substituted by —C(O)R$^{22}$; and wherein the aryl and heteroaryl radicals are optionally substituted by 1–3 radicals of hydroxy, C$_1$–C$_4$ alkoxy, C$_1$–C$_4$ alkylthiol, amino, C$_1$–C$_4$ alkanoylamino, C$_1$–C$_4$ alkylsulfonylamino, C$_1$–C$_4$ alkylsulfinyl, C$_1$–C$_4$ alkylsulfonyl, C$_1$–C$_4$ alkoxycarbonylamino, C$_1$–C$_4$ alkoxycarbonyl, cyano, halo, azido, C$_1$–C$_4$ alkyl, C$_1$–C$_4$ haloalkyl of 1–3 halo radicals or C$_1$–C$_4$ haloalkoxy of 1–3 halo radicals;

more preferably, each R$^{20}$ is independently a hydrogen, C$_1$–C$_4$ alkyl, C$_2$–C$_4$ alkenyl, aryl, heteroaryl, aryl-C$_1$–C$_4$-alkyl, heteroaryl-C$_1$–C$_4$-alkyl, C$_1$–C$_4$ alkanoyl, aroyl or heteroaroyl radical; wherein the alkyl and alkenyl radicals are optionally substituted by —C(O)R$^{22}$; and wherein the aryl and heteroaryl radicals are optionally substituted by 1–3 radicals of hydroxy, C$_1$–C$_4$ alkoxy, C$_1$–C$_4$ alkylthiol, amino, acetylamino, methylsulfonylamino, methylsulfinyl, methylsulfonyl, C$_1$–C$_4$ alkoxycarbonylamino, C$_1$–C$_4$ alkoxycarbonyl, cyano, halo, azido, C$_1$–C$_4$ alkyl, —CF$_3$ or —OCF$_3$ radicals;

more preferably, each R$^{20}$ is independently a hydrogen, C$_1$–C$_4$ alkyl, C$_1$–C$_4$ alkyl—C(O)R$^{22}$, C$_2$–C$_4$ alkenyl, aryl, heteroaryl, aryl-C$_1$–C$_2$-alkyl, heteroaryl-C$_1$–C$_2$-alkyl or C$_1$–C$_4$ alkanoyl radical; and wherein the aryl and heteroaryl radicals are optionally substituted by 1–2 radicals of hydroxy, C$_1$–C$_4$ alkoxy, C$_1$–C$_4$ alkylthiol, halo, azido, C$_1$–C$_2$ alkyl, —CF$_3$ or —OCF$_3$ radicals;

more preferably, each R$^{20}$ is independently a hydrogen, C$_1$–C$_4$ alkyl, C$_2$–C$_4$ alkenyl, aryl, heteroaryl, aryl-C$_1$–C$_2$-alkyl, heteroaryl-C$_1$–C$_2$-alkyl or C$_1$–C$_4$ alkanoyl radical;

more preferably, each R$^{20}$ is independently a hydrogen, C$_1$–C$_4$ alkyl, C$_2$–C$_4$ alkenyl, phenyl, heteroaryl, phenyl-C$_1$–C$_2$-alkyl, heteroaryl-C$_1$–C$_2$-alkyl or radical; and most preferably, each R$^{20}$ is independently a hydrogen, methyl, propenyl, phenyl, heteroaryl, phenyl-C$_1$–C$_2$-alkyl or heteroaryl-C$_1$–C$_2$-alkyl radical;

wherein each R$^{21}$ is independently an alkyl, alkyl-C(O)R$^{22}$, aryl, heteroaryl, aryl-alkyl or heteroaryl-alkyl radical; wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each R$^{21}$ is independently a C$_1$–C$_8$ alkyl, C$_1$–C$_8$ alkyl-C(O)R$^{22}$, aryl, heteroaryl, aryl-C$_1$–C$_4$-alkyl or heteroaryl-C$_1$–C$_4$-alkyl radical; wherein the aryl and heteroaryl radicals are optionally substituted by 1–3 radicals of hydroxy, C$_1$–C$_4$ alkoxy, C$_1$–C$_4$ alkylthiol, amino, C$_1$–C$_8$ alkanoylamino, C$_1$–C$_8$ alkylsulfonylamino, C$_1$–C$_4$ alkylsulfinyl, C$_1$–C$_4$ alkylsulfonyl, C$_1$–C$_8$ alkoxycarbonylamino, C$_1$–C$_8$ alkoxycarbonyl, cyano, halo, azido, C$_1$–C$_8$ alkyl, C$_1$–C$_8$ haloalkyl of 1–3 halo radicals or C$_1$–C$_8$ haloalkoxy of 1–3 halo radicals;

more preferably, each R$^{21}$ is independently a C$_1$–C$_4$ alkyl, C$_1$–C$_4$ alkyl-C(O)R$^{22}$, aryl, heteroaryl, aryl-C$_1$–C$_4$-alkyl or heteroaryl-C$_1$–C$_4$-alkyl radical; wherein the aryl and heteroaryl radicals are optionally substituted by 1–3 radicals of hydroxy, C$_1$–C$_4$ alkoxy, C$_1$–C$_4$ alkylthiol, amino, C$_1$–C$_4$ alkanoylamino, C$_1$–C$_4$ alkylsulfonylamino, C$_1$–C$_4$ alkylsulfinyl, C$_1$–C$_4$ alkylsulfonyl, C$_1$–C$_4$ alkoxycarbonylamino, C$_1$–C$_4$ alkoxycarbonyl, cyano, halo, azido, C$_1$–C$_4$ alkyl, C$_1$–C$_4$ haloalkyl of 1–3 halo radicals or C$_1$–C$_4$ haloalkoxy of 1–3 halo radicals;

more preferably, each R$^{21}$ is independently a C$_1$–C$_4$ alkyl, C$_1$–C$_4$ alkyl-C(O)R$^{22}$, aryl, heteroaryl, aryl-C$_1$–C$_4$-alkyl or heteroaryl-C$_1$–C$_4$-alkyl radical; wherein the aryl and heteroaryl radicals are optionally substituted by 1–3 radicals of hydroxy, C$_1$–C$_4$ alkoxy, C$_1$–C$_4$ alkylthiol, amino, acetylamino, methylsulfonylamino, methylsulfinyl, methylsulfonyl, C$_1$–C$_4$ alkoxycarbonylamino, C$_1$–C$_4$ alkoxycarbonyl, cyano, halo, azido, C$_1$–C$_4$ alkyl, —CF$_3$ or —OCF$_3$ radicals; and most preferably, each R$^{21}$ is independently a C$_1$–C$_4$ alkyl, C$_1$–C$_4$ alkyl-C(O)R$^{22}$, aryl, heteroaryl, aryl-C$_1$–C$_2$-alkyl or heteroaryl-C$_1$–C$_2$-alkyl radical; wherein the aryl and heteroaryl radicals are optionally substituted by 1–2 radicals of hydroxy, C$_1$–C$_4$ alkoxy, C$_1$–C$_4$ alkylthiol, halo, azido, C$_1$–C$_2$ alkyl, —CF$_3$ or —OCF$_3$ radicals;

wherein each R$^{22}$ is independently a hydroxy, alkoxy, aryloxy, aryl-alkoxy, heteroaryloxy, heteroaryl-alkoxy or —NR$^{23}$R$^{24}$ radical; preferably, each R$^{22}$ is independently a hydroxy, C$_1$–C$_8$ alkoxy, aryloxy, aryl-C$_1$–C$_4$-alkoxy, heteroaryloxy, heteroaryl-C$_1$–C$_4$-alkoxy or —NR$^{23}$R$^{24}$ radical; more preferably, each R$^{22}$ is independently a hydroxy, C$_1$–C$_4$ alkoxy, aryloxy, aryl-C$_1$–C$_2$-alkoxy, heteroaryloxy, heteroaryl-C$_1$–C$_2$-alkoxy or —NR$^{23}$R$^{24}$ radical; and most preferably, each R$^{22}$ is independently a hydroxy or —NR$^{23}$R$^{24}$ radical;

wherein each R$^{23}$ is independently a hydrogen, alkyl, aryl, aryl-alkyl, heteroaryl or heteroaryl-alkyl radical; preferably, each R$^{23}$ is independently a hydrogen, C$_1$–C$_8$ alkyl, aryl, aryl-C$_1$–C$_4$-alkyl, heteroaryl or heteroaryl-C$_1$–C$_4$-alkyl radical; and most preferably, each R$^{23}$ is independently a hydrogen, C$_1$–C$_4$ alkyl, aryl, aryl-C$_1$–C$_2$-alkyl, heteroaryl or heteroaryl-C$_1$–C$_2$-alkyl radical; and each R$^{24}$ is independently a hydrogen or alkyl radical; preferably, each R$^{24}$ is independently a hydrogen or $C_1$–$C_8$ alkyl radical; more preferably, each $R^{24}$ is independently a hydrogen or $C_1$–$C_4$ alkyl radical; and most preferably, each $R^{24}$ is independently a hydrogen or $C_1$–$C_2$ alkyl radical; or —$NR^{23}R^{24}$ represents a heterocyclyl or heteroaryl radical; preferably, —$NR^{23}R^{24}$ represents a heterocyclyl or heteroaryl radical; and wherein the heterocyclyl, aryl and heteroaryl radicals of $R^{22}$, $R^{23}$ and —$NR^{23}R^{24}$ are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals;

more preferably, optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, optionally substituted by 1–3 radicals of hydroxy, $C_1$–$C_4$ alkoxy, $C_1$–$C_4$ alkylthiol, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, amino, —$CF_3$ or —$OCF_3$ radicals;

more preferably, optionally substituted by 1–2 radicals of hydroxy, $C_1$–$C_4$ alkoxy, $C_1$–$C_4$ alkylthiol, halo, azido, $C_1$–$C_4$ alkyl, —$CF_3$ or —$OCF_3$ radicals; and most preferably, optionally substituted by 1–2 radicals of hydroxy, $C_1$–$C_2$ alkoxy, $C_1$–$C_2$ alkylthiol, halo, azido, $C_1$–$C_2$ alkyl, —$CF_3$ or —$OCF_3$ radicals; and wherein $R^5$, $R^6$, $R^7$ and $R^8$ are each independently a hydrogen or alkyl radical; preferably, $R^5$, $R^6$, $R^7$ and $R^8$ are each independently a hydrogen or $C_1$–$C_4$ alkyl radical; and more preferably, $R^5$, $R^6$, $R^7$ and $R^8$ are each a hydrogen radical; or one of $CR^5$—$CR^6$, $CR^6$—$CR^7$ or $CR^7$—$CR^8$ is C=C (double bonded carbon atoms);

wherein $R^9$ and $R^{10}$ are each independently -B-A, provided that the combined total number of aryl, heteroaryl, cycloalkyl and heterocyclyl radicals in $R^9$, $R^{10}$, $R^{11}$ and $R^{12}$ is 0–3, preferably, 0–2;

wherein each B is independently a (1) bond; (2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and/or (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy; (3) heterocyclyl radical optionally substituted by 1–3 radicals of amino, alkylamino, dialkylamino, alkanoylamino, alkoxycarbonyl amino, alkylsulfonylamino, hydroxy, alkoxy, alkylthio, cyano, alkyl, haloalkyl or haloalkoxy; or (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;

preferably, each B is independently a (1) bond; (2) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano or halo, and/or (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkyl sulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals; (3) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_8$ haloalkyl of 1–3 halo radicals or $C_1$–$C_8$ haloalkoxy of 1–3 halo radicals;

more preferably, each B is independently a (1) bond; (2) $C_1$–$C_8$ alkyl radical optionally substituted by (a) a radical of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ halo alkoxy of 1–3 halo radicals; (3) heterocyclyl radical; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each B is independently a (1) bond; (2) $C_1$–$C_8$ alkyl radical optionally substituted by (a) a radical of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkyl thio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals; (3) heterocyclyl radical; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkyl sulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

more preferably, each B is independently a (1) bond; (2) $C_1$–$C_4$ alkyl radical optionally substituted by (a) a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, hydroxy, $C_1$–$C_2$ alkoxy, and/or (b) 1–2 halo radicals, and/or (c) a radical of heterocyclyl, aryl or heteroaryl optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals; (3) heterocyclyl radical; or (4) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

more preferably, each B is independently a (1) bond or $C_1$–$C_4$ alkyl radical; or (2) aryl or heteroaryl radical optionally substituted by a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals; and most preferably, each B is independently a bond, $C_1$–$C_4$ alkyl, aryl or heteroaryl radical;

wherein each A is independently a (1) hydrogen radical; (2) halo, cyano or nitro radical; (3) —$C(O)$—$R^{30}$, —$C(O)$—$OR^{31}$, —$C(O)$—$NR^{32}R^{31}$ or —$C(NR^{32})$—$NR^{32}R^{31}$ radical; (4) —$OR^{31}$, —$O$—$C(O)$—$R^{31}$, —$O$—$C(O)$—$NR^{32}R^{31}$ or —$O$—$C(O)$—$NR^{33}$—$S(O)_2$—$R^{30}$ radical; (5) —$SR^{31}$, —$S(O)$—$R^{30}$, —$S(O)_2$—$R^{30}$, —$S(O)_2$—$NR^{32}R^{31}$, —$S(O)_2$—$NR^{33}$—$C(O)$—$R^{31}$, —$S(O)_2$—$NR^{33}$—$C(O)$—$OR^{30}$ or —$S(O)_2$—$NR^{33}$—$C(O)$—$NR^{32}R^{31}$ radical; or (6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$C(NR^{32})$—$NR^{32}R^{31}$, —$NR^{33}$—$S(O)_2$—$R^{30}$ or —$NR^{33}$—$S(O)_2$—$NR^{32}R^{31}$ radical;

preferably, each A is independently a (1) hydrogen radical; (2) halo, cyano or nitro radical; (3) —$C(O)$—$R^{30}$, —$C(O)$—$R^{31}$, —$C(O)$—$NR^{32}R^{31}$ or —$C(NR^{32})$—$NR^{32}R^{31}$ radical; (4) —$OR^{31}$, —$O$—$C(O)$—$R^{31}$, —$O$—$C(O)$—$NR^{32}R^{31}$ or —$O$—$C(O)$—$NR^{33}$—$S(O)_2$—$R^{30}$ radical; (5) —$SR^{31}$, —$S(O)$—$R^{30}$, —$S(O)_2$—$R^{30}$, —$S(O)_2$—$NR^{32}R^{31}$, —$S(O)_2$—$NR^{33}$—$C(O)$—$R^{31}$, —$S(O)_2$—$NR^{33}$—$C(O)$—$OR^{30}$ or —$S(O)_2$—$NR^{33}$—$C(O)$—$NR^{32}R^{31}$ radical; or (6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$C(NR^{32})$—$NR^{32}R^{31}$, —$NR^{33}$—$S(O)_2$—$R^{30}$ or —$NR^{33}$—$S(O)_2$—$NR^{32}R^{31}$ radical;

more preferably, each A is independently a hydrogen, halo, cyano, nitro, —$C(O)$—$R^{30}$, —$C(O)$—$OR^{31}$, —$C(O)$—$NR^{32}R^{31}$, —$C(NR^{32})$—$NR^{32}R^{31}$, —$OR^{31}$, —$O$—$C(O)$—$R^{31}$, —$O$—$C(O)$—$NR^{32}R^{31}$, —$SR^{31}$, —$S(O)$—$R^{30}$, —$S(O)_2$—$R^{30}$, —$S(O)_2$—$NR^{32}R^{31}$, —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$C(NR^{32})$—$NR^{32}R^{31}$, —$NR^{33}$—$S(O)_2$—$R^{30}$ or —$NR^{33}$—$S(O)_2$—$NR^{32}R^{31}$ radical;

more preferably, each A is independently a hydrogen, halo, —$C(O)$—$R^{30}$, —$C(O)$—$OR^{31}$, —$C(O)$—$NR^{32}R^{31}$, —$C(NR^{32})$—$NR^{32}R^{31}$, —$OR^{31}$, —$SR^{31}$, —$S(O)_2$—$R^{30}$, —$S(O)_2$—$NR^{32}R^{31}$, —$NR^{32}R^{31}$, —$NR^{33}$—$C(O)$—$R^{31}$, —$NR^{33}$—$C(O))$—$OR^{30}$, —$NR^{33}$—$C(O)$—$NR^{32}R^{31}$, —$NR^{33}$—$S(O)_2$—$R^{30}$ or —$NR^{33}$—$S(O)_2$—$NR^{32}R^{31}$ radical;

more preferably, each A is independently a hydrogen, halo, —$C(O)$—$R^{30}$, —$C(O)$—$NR^{32}R^{31}$, —$C(NR^{32})$—$NR^{32}R^{31}$, —$OR^{31}$, —$SR^{31}$, —$S(O)_2$—$R^{30}$, —$S(O)_2$—$NR^{32}R^{31}$, —$NR^{32}R^{31}$, —$NR^{33}$—$C(O)$—$R^{31}$ or —$NR^{33}$—$S(O)_2$—$R^{30}$ radical; and most preferably, each A is independently a hydrogen, halo, —$C(O)$—$R^{30}$ or —$C(O)$—$NR^{32}R^{31}$ radical;

wherein each $R^{30}$ is independently (1) alkyl, alkenyl or alkynyl radical optionally substituted by 1–3 radicals of —$CO_2R^{34}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonyl amino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy; (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

preferably, each $R^{30}$ is independently (1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{30}$ is independently (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{30}$ is independently (1) $C_1$–$C_6$ alkyl radical optionally substituted by 1–3 radicals of $CO_2R^{34}$, amino, $C_1$–$C_4$ alkylamino, di-($C_1$–$C_4$ alkyl) amino, $C_1$–$C_5$ alkanoylamino, ($C_1$–$C_4$ alkoxy) carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or (3) aryl or heteroaryl radical optionally substituted by 1–3 radicals of amino, $C_1$–$C_4$ alkylamino, di-($C_1$–$C_4$ alkyl)-amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

more preferably, each $R^{30}$ is independently (1) —$CF_3$ or $C_1$–$C_4$ alkyl radical optionally substituted by 1–2 radicals of —$CO_2R^{34}$, amino, $C_1$–$C_2$ alkylamino, di-($C_1$–$C_2$ alkyl)amino, $C_1$–$C_2$ alkanoylamino, ($C_1$–$C_4$ alkoxy)carbonylamino, N-(($C_1$–$C_4$ alkoxy)carbonyl)-N-($C_1$–$C_4$ alkyl)amino, hydroxy, $C_1$–$C_4$ alkoxy, or aryl-$C_1$–$C_2$-alkoxy, heterocyclyl, aryl or heteroaryl radicals, wherein the heterocyclyl, aryl and heteroaryl radicals are optionally substituted by 1–3 radicals of amino, $C_1$–$C_2$ alkylamino, di-($C_1$–$C_2$ alkyl) amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —$CF_3$ or —$OCF_3$ radicals; (2) heterocyclyl radical optionally substituted by 1–2 radicals of ($C_1$–$C_4$ alkoxy)carbonyl, hydroxy or $C_1$–$C_4$ alkyl; or (3) aryl or heteroaryl radicals optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —$CF_3$ or —$OCF_3$ radicals;

more preferably, each $R^{30}$ is independently (1) heterocyclyl radical optionally substituted by 1–2 radicals of ($C_1$–$C_4$ alkoxy)carbonyl, hydroxy or $C_1$–$C_4$ alkyl; or (2) heteroaryl radicals optionally substituted by 1–2 radicals of amino, $C_1$–$C_2$ alkylamino, di-($C_1$–$C_2$ alkyl) amino, $C_1$–$C_2$ alkanoylamino, hydroxy, $C_1$–$C_2$ alkoxy, halo, $C_1$–$C_4$ alkyl, —$CF_3$ or —$OCF_3$ radicals; and most preferably, each $R^{30}$ is independently a heterocyclyl radical optionally substituted by $C_1$–$C_4$ alkyl;

wherein each $R^{31}$ is independently hydrogen radical or (1) alkyl, alkenyl or alkynyl radical optionally substituted by 1–3 radicals of —$CO_2R^{34}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonylamino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy; (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

preferably, each $R^{31}$ is independently hydrogen radical or (1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl) amino, $C_1$–$C_5$ alkanoylamino, ($C_1$–$C_4$ alkoxy) carbonylamino, N-(($C_1$–$C_4$ alkoxy) carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)-amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{31}$ is independently hydrogen radical or (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{31}$ is independently hydrogen radical or (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

more preferably, $R^{31}$ is independently hydrogen radical or (1) —$CF_3$ or $C_1$–$C_4$ alkyl radical optionally substituted by 1–2 radicals of hydroxy, $C_1$–$C_2$ alkoxy or aryl-$C_1$–$C_2$-alkoxy, aryl or heteroaryl radicals, wherein the aryl and heteroaryl radicals are optionally substituted by 1–2 radicals of amino, $C_1$–$C_2$ alkylamino, di-($C_1$–$C_2$ alkyl) amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —$CF_3$ or —$OCF_3$ radicals; or (2) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —$CF_3$ or —$OCF_3$ radicals; and most preferably, each $R^{31}$ is independently hydrogen radical or (1) —$CF_3$ or $C_1$–$C_4$ alkyl radical optionally substituted by 1–2 radicals of aryl or heteroaryl radicals; or (2) aryl or heteroaryl radical;

wherein each $R^{32}$ is independently (1) hydrogen radical; (2) alkyl, alkenyl or alkynyl radical optionally substituted by 1–3 radicals of amino, alkylamino, dialkylamino, hydroxy, alkoxy, alkylthio, cyano or halo; or (3) aryl, heteroaryl, arylalkyl, heteroarylalkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, cyano, alkyl, haloalkyl or haloalkoxy;

preferably, each $R^{32}$ is independently (1) hydrogen radical; (2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or (3) aryl, heteroaryl, aryl-$C_1$–$C_4$-alkyl, heteroaryl-$C_1$–$C_4$- alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{32}$ is independently hydrogen or $C_1$–$C_4$ alkyl radical; and most preferably, each $R^{32}$ is independently a hydrogen or methyl radical;

wherein each $R^{33}$ is independently (1) hydrogen radical; (2) alkyl radical optionally substituted by a radical of heterocyclyl, aryl or heteroaryl which is optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; or (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy;

preferably, each $R^{33}$ is independently (1) hydrogen radical; (2) $C_1$–$C_4$ alkyl radical optionally substituted by a radical of heterocyclyl, aryl or heteroaryl which is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; or (3) heterocyclyl, aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{33}$ is independently hydrogen or $C_1$–$C_4$ alkyl radical; and most preferably, each $R^{33}$ is independently a hydrogen or methyl radical; and wherein each $R^{34}$ is independently hydrogen, alkyl, aryl, heteroaryl, arylalkyl or heteroarylalkyl radical, wherein the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy;

preferably, each $R^{34}$ is independently hydrogen or $C_1$–$C_4$ alkyl, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{34}$ is independently hydrogen or $C_1$–$C_4$ alkyl radical; and most preferably, each $R^{34}$ is independently a hydrogen or methyl radical.

The symbols used above have the following meanings:

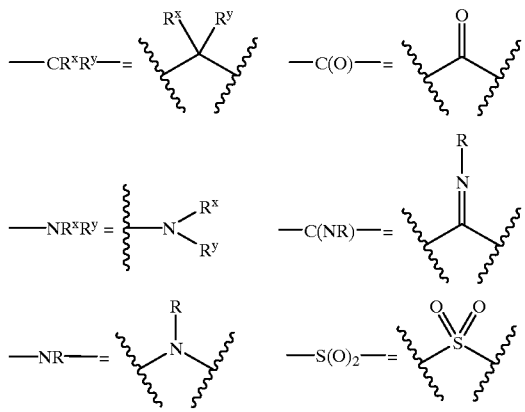

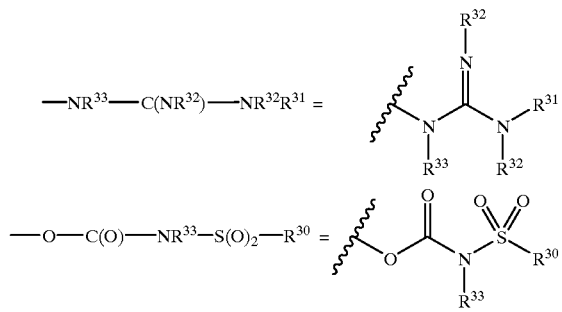

An aryl radical optionally substituted by an optionally substituted monocyclic heteroaryl or heterocyclyl radical of 5–6 ring members which is optionally substituted by a phenyl radical or monocyclic heteroaryl radical of 5–6 ring members means an aryl radical which is optionally substituted by (a) a monocyclic heteroaryl radical of 5–6 ring members optionally substituted by a phenyl radical or monocyclic heteroaryl radical of 5–6 ring members; or (b) a monocyclic heterocyclyl radical of 5–6 ring members optionally substituted by a phenyl radical or monocyclic heteroaryl radical of 5–6 ring members.

A heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members means a heteroaryl radical which is optionally substituted by (a) a phenyl radical optionally substituted by a phenyl radical or monocyclic heteroaryl radical of 5–6 ring members; (b) a monocyclic heteroaryl radical of 5–6 ring members optionally substituted by a phenyl radical or monocyclic heteroaryl radical of 5–6 ring members; or (c) a monocyclic heterocyclyl radical of 5–6 ring members optionally substituted by a phenyl radical or monocyclic heteroaryl radical of 5–6 ring members.

The compounds of this invention have in general several asymmetric centers and are depicted in the form of racemic mixtures. This invention is intended to encompass racemic mixtures, partially racemic mixtures and separate enantiomers and diastereomers. Preferably, the absolute configuration of the hydroxamic acid group is (R). Preferably, the relative configuration of the hydroxamic acid group and the substituents of V other than hydrogen (i.e., when $R^{11}$ and/or $R^{12}$ are other than hydrogen) is cis, i.e., the hydroxamic acid and the substituents of V are on the same face of the ring system.

Compounds of interest include the following:

cis-3-benzyl-1-(4-methoxyphenylsulfonyl)-azepane-2-hydroxamic acid;
trans-3-benzyl-1-(4-methoxyphenylsulfonyl)-azepane-2-hydroxamic acid;
trans-3-phenyl-1-(4-methoxyphenylsulfonyl)-azepane-2-hydroxamic acid;
1-(4-methoxyphenylsulfonyl)-azepane-2-hydroxamic acid;
acetic acid (2-hydroxycarbamoyl-1-(4-methoxyphenylsulfonyl)-azepan-3-yl)methyl ester;
3-hydroxymethyl-1-(4-methoxyphenylsulfonyl)-azepane-2-hydroxamic acid;
3-benzyloxymethyl-1-(4-methoxyphenylsulfonyl)-azepane-2-hydroxamic acid;
1-(4-methoxyphenylsulfonyl)-3-phenylsulfanylmethyl-azepane-2-hydroxamic acid;
1-(4-methoxyphenylsulfonyl)-3-styryl-azepane-2-hydroxamic acid;
3-(2-hydroxycarbamoyl-1-(4-methoxyphenylsulfonyl)-azepan-3-yl)acrylic acid;
acetic acid (2-hydroxycarbamoyl-1-(4-methoxyphenylsulfonyl)-2,3,4,7-tetrahydro-1H-azepin-3-yl)methyl ester;
3-hydroxymethyl-1-(4-methoxyphenylsulfonyl)-2,3,4,7-tetrahydro-1H-azepine-2-hydroxamic acid;
3-benzyloxymethyl-1-(4-methoxyphenylsulfonyl)-2,3,4,7-tetrahydro-1H-azepine-2-hydroxamic acid;
1-(4-methoxyphenylsulfonyl)-3-phenylsulfanylmethyl-2,3,4,7-tetrahydro-1H-azepine-2-hydroxamic acid; and
3-benzofuran-2-yl-1-(4-methoxyphenylsulfonyl)-2,3,4,7-tetrahydro-1H-azepine-2-hydroxamic acid.

As utilized herein, the following terms shall have the following meanings:

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkynyl", alone or in combination, means a straight-chain or branched chain hydrocarbon radical having one or more triple bonds, preferably 1–2 triple bonds and ore preferably one triple bond, and containing referably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkynyl radicals include ethynyl, propynyl (propargyl), butynyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Alkylsulfonylamino", alone or in combination, means a radical of the type "R—S(O)$_2$—NH—" wherein "R—S(O)$_2$—" is an alkylsulfonyl radical as defined above, wherein the amino radical may optionally be substituted, such as with alkyl, aryl, aralkyl, cycloalkyl, cycloalkylalkyl and the like.

"Aryl", alone or in combination, means a phenyl, biphenyl or naphthyl radical which is optionally substituted with one or more substituents selected from alkyl, alkoxy, halogen, hydroxy, amino, azido, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy) phenyl, 3-methyl-4-methoxyphenyl, 4-$CF_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 4-(4-methoxyphenyl)phenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like.

"Aryl-alkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 2-naphthylmethyl, 4-methoxyphenylmethyl and the like.

"Aryl-alkoxy", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aryloxy", alone or in combination, means a radical of the type "R—O—" wherein "R" is an aryl radical as defined above.

"Aroyl", alone or in combination, means a radical of the type "R—C(O)—" wherein "R" is an aryl radical as defined above and "—C(O)—" is a carbonyl.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonylamino", alone or in combination, means an amino substituted carbonyl substituted on a second amino (ureido) radical, wherein each amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Benzo", alone or in combination, means the divalent radical $C_6H_4=$ derived from benzene.

"Bicyclic" as used herein is intended to include both fused ring systems, such as naphthyl and β-carbolinyl, and substituted ring systems, such as biphenyl, phenylpyridyl, naphthyl and diphenylpiperazinyl.

"Cycloalkyl", alone or in combination, means a saturated or partially saturated, preferably one double bond, monocyclic, bicyclic or tricyclic alkyl radical, preferably monocyclic, containing preferably 3–10 carbon atoms ($C_3$–$C_{10}$), more preferably 3–8 carbon atoms ($C_3$–$C_8$), even more preferably 3–6 carbon atoms ($C_3$–$C_6$), which is optionally be benzo fused and which is optionally substituted as defined herein with respect to the definition of aryl. Examples of such cycloalkyl radicals include cyclopropyl, cyclobutyl, cyclopentyl, cyclohexyl, dihydroxycyclohexyl, cycloheptyl, octahydronaphthyl, tetrahydronaphthyl, dimethoxytetrahydronaphthyl, 2,3-dihydro-1H-indenyl and the like.

"Cycloalkylalkyl", alone or in combination, means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, hydroxycyclopentylpropyl, tetrahydronaphthylpropyl, cyclohexylbutyl and the like.

"Heteroatoms" means nitrogen, oxygen and sulfur heteroatoms.

"Heterocyclyl", alone or in combination, means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heterocyclylalkyl", alone or in combination, means an alkyl radical as defined above in which at least one hydrogen atom, preferably 1–2, is replaced by a heterocyclyl radical as defined above, such as pyrrolidinylmethyl, tetrahydrothienylmethyl, piperidinylethyl and the like.

"Heteroaryl", alone or in combination, means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally benzo fused or saturated carbocyclic fused, preferably 3–4 carbon atoms ($C_3$–$C_4$) to form 5–6 ring membered rings and which is optionally substituted as defined above with respect to the definitions of aryl and heterocyclyl. More preferably, "heteroaryl", alone or in combination, is a radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused. Examples of such heteroaryl groups include imidazolyl, 1-benzyloxycarbonylimidazol-4-yl, pyrrolyl, pyrazolyl, pyridyl, 2-(1-piperidinyl)pyridyl, 2-(4-benzyl piperazin-1-yl)-1-pyridinyl, pyrazinyl, triazolyl, furyl, thienyl, oxazolyl, thiazolyl, indolyl, quinolinyl, 1-oxido-2-quinolinyl, isoquinolinyl, 5,6,7,8-tetrahydroquinolyl, 5,6,7,8-tetrahydroisoquinolinyl, quinoxalinyl, benzothiazolyl, β-carbolinyl, benzofuryl, benzimidazolyl, benzoxazolyl and the like.

"Heteroaroyl", alone or in combination, means a radical of the type "R—C(O)—" wherein "R" is an heteroaryl radical as defined above and "—C(O)—" is a carbonyl.

"Heteroaryl-alkyl", alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl) methyl and the like.

"Haloalkoxy", alone or in combination, means an alkoxy radical as defined above in which at least one hydrogen atom, preferably 1–3, is replaced by a halogen radical, more preferably fluoro or chloro radicals. Examples of such haloalkoxy radicals include 2,2,2-trifluoroethoxy, chloromethoxy, 2-bromoethoxy, fluoromethoxy, difluoromethoxy, trifluoromethoxy, bis (trifluoromethyl)methoxy and the like.

"Sulfinyl", alone or in combination, means a diradical of the type "—S(O)—" wherein "S(O)" is a mono-oxygenated sulfur atom. "Sulfonyl", alone or in combination, means a diradical of the type "—S(O)$_2$—" wherein "S(O)$_2$" is a di-oxygenated sulfur atom.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Procedures for preparing the compounds of this invention are set forth below. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Preparation of Compounds of Formula I

The compounds of the present invention represented by Formula I above can be prepared using various synthesis techniques, many of which are included by reference. In particular, compounds of the present invention can be prepared following the general procedures discussed below.

A general synthesis useful for the preparation of the novel compounds of this invention is illustrated in Scheme I. The synthesis in Scheme I is based on a Schmidt ring expansion to produce the medium ring, after introduction of substitution via conjugate addition. In accordance with this embodiment, a substituted α,β unsaturated ketone prepared by methods known in the art, is treated with an alkyl or aryl (optionally substituted with heteroatoms) organometallic reagent, preferably a cuprate or copper catalyzed grinard (see Posner, Org. React. 1972, 19, 1–113) from −78° C. to room temperature, preferably in an ether solvent and the resulting anion trapped with a chloroformate or other acylating agent. The substituted β-keto ester is then rearranged under Schmidt conditions (see Scriven Azides and Nitrenes, Academic Press, 1984) to provide the lactam.

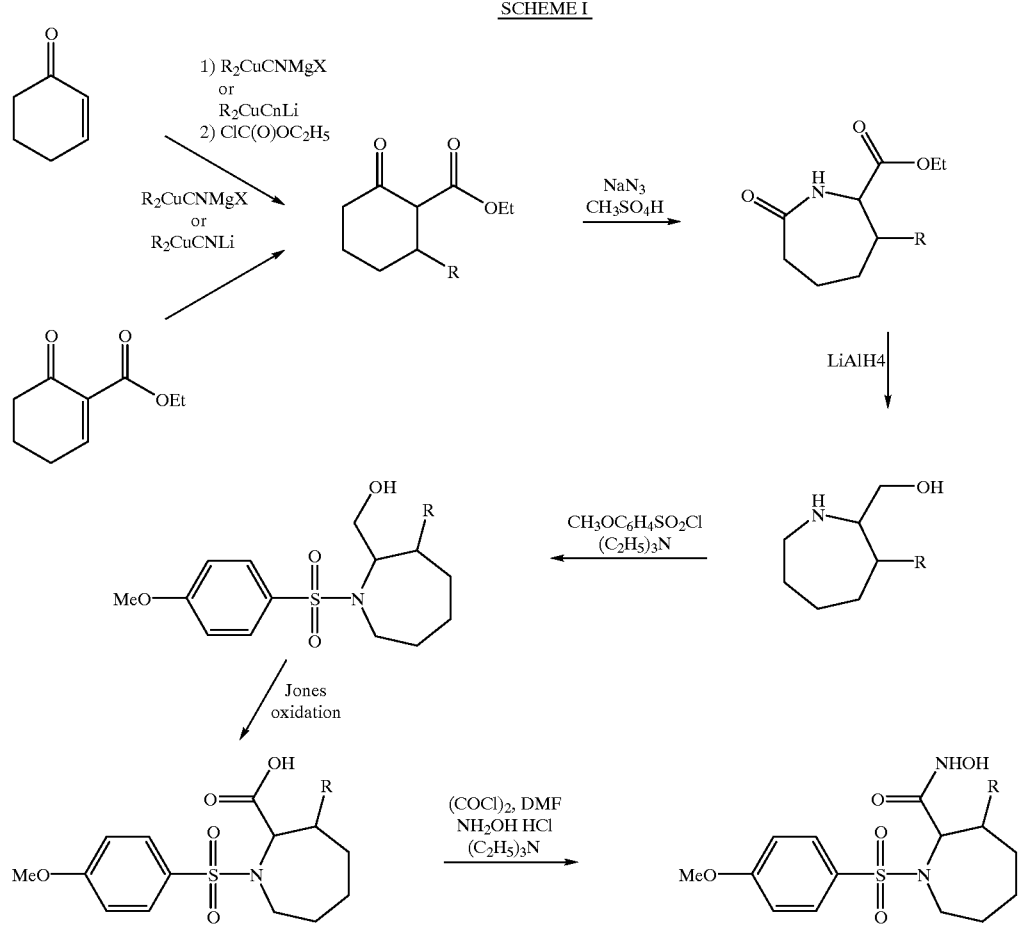

SCHEME I

The lactam is reduced by methods known by one skilled in the art preferably with Lithium aluminum hydride or Red-Al in THF, to provide the amino alcohols. Sulfonylation with a sulfonyl halide in the presence of a base, preferably a hindered amine base such as triethyl amine in a chlorinated solvent provides the substituted sulfonamide. Oxidation under standard conditions (see Hudlicky, Oxidations in Organic Chemistry, ACS mongraph 186, 1990), preferably under Jones conditions provides the acid. Activation of the acid under known conditions, preferably as the acid chloride and condensation with hydroxyl amine provide the hydroxamic acid final product final product.

Preferably, when utilizing the general synthesis of Scheme I in the preparation of the novel compounds of this invention, R will not contain aldehyde, halogenated or any other radicals well known to those skilled in the art which have the potential of interfering with, competing with or inhibiting the bond formation reaction.

The readily available aspartic, or glutamic acid derivative is protected and allylated as described previously for an analog (see Baldwin, Tetrahedron, 1989, 45, 6309 and references cited therein). Mitsunobu reaction of the resulting sulfonamide (see Mitsunobu, Synthesis, 1981, 1) provides the bis olefin. Treatment of the resulting olefin with a metathesis reagent (see Schuster, Angew. Chem. Int. Ed. Engl. 1997, 36, 2036) provides the cyclized olefin. Saponification, as known by one skilled in the art, followed by curtius rearrangment of the resultant acid under known conditions (Tetrahedron, 1974, 30, 2151) provides the desired carbamates. The t-butyl acid protected carbamates

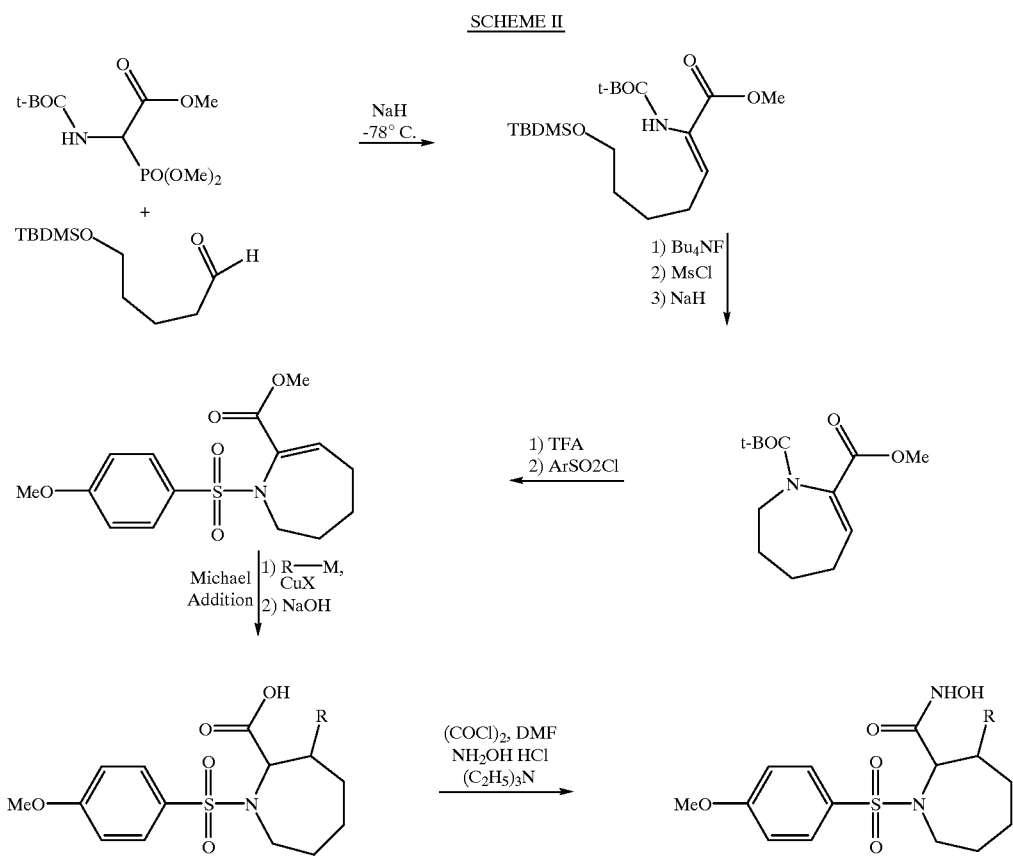

A second general synthesis useful for the preparation of the novel compounds of this invention is illustrated in Scheme II, which employs a convergent route to the azepine ring. According to this method, the readily available Horner-emmons reagent is reacted under standard conditions (see Wadsworth, Org. Reactions, 1977, 25, 73) with an aldehyde variably substituted by a silyl ether as well as additional substitution (to introduce $R^5$, $R^6$, $R^7$, $R^9$ and $R^{10}$) on the alkyl chain to provide the α,β-unsaturated ester. Deprotection of the silyl group, activation of the alcohol to provide a leaving group and intramolecular base catalyzed closure provides a similar intermediate to that described in Scheme I. Subsequent deprotection and treatment as described previously provides the desired hydroxamic acid products.

A third general synthesis useful for the preparation of the novel compounds of this invention is illustrated in Scheme III, which employs a convergent route to the azepine ring.

can be deprotected with concentrated trifluoroacetic acid (TFA) to provide the final products. Additionally, by choosing the appropriate alcohol trapping agent for the Curtius rearrangement, for example, 4-methoxy benzyl alcohol, the carbamate may be diferentially deprotected to the amine with dilute (3%) TFA in a chlorinated solvent to provide the t-butyl protected acid, amine salt. Sulfonylation, as described previously, or treatment with the appropiate alkylating or acylating agent as known by one skilled in the art and deprotection of the t-butyl ester as described provides the carboxylic acid intermediates. Larger rings can be formed by using homologues of allyl-iodide or allyl alcohol, such as 4-iodo-1-butene, 4-hydroxy-1-butene, 5-iodo-1-pentene, 5-hydroxy-1-pentene, 4-iodo-2-butene, 4-hydroxy-2-butene and the like.

SCHEME III

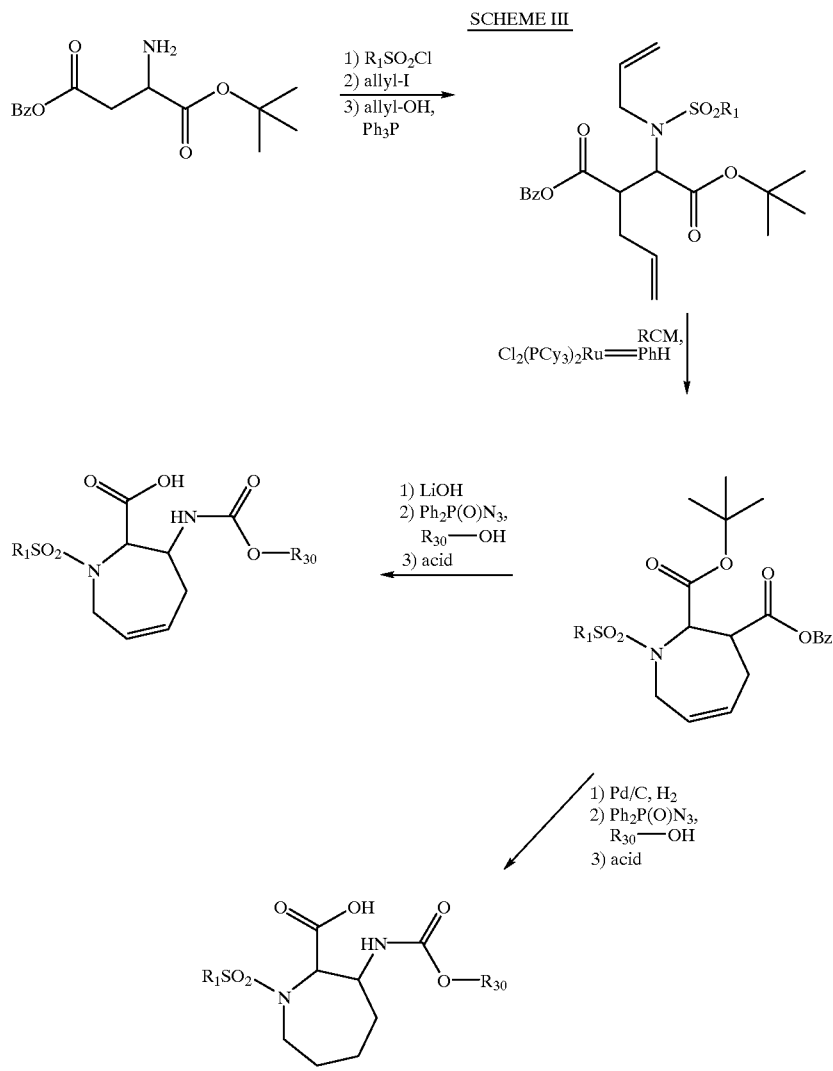

Intermediates from Scheme III can be used as starting materials for substituents $R^5$, $R^6$, $R^7$, $R^9$ and $R^{10}$. For example, the aspartic acid derivative, can be alkylated with a variety of polysubstituted allyl iodides or triflates such as $CH_2=CH_2CHR^7R^{10}I$ followed by Mitzunubu reaction with with allyl and homoallyl alcohols to provide intermediates for methathesis reaction. The compounds claimed may also be prepared by funtionalization of the olefinic intermediates after metathesis. For example, the olefin can be hydrogenated under standard conditions, preferably, Pd/C under an atmosphere of hydrogen in a solvent such as a alcohol, or ethyl acetate. The olefin can be hydroborated with a borane reagent, (see Brown, Borane Reagents, Academic Press, NY, 1988) preferably, $BH_3$-DMS, and the subsequent borane complex oxidized with $H_2O_2$ to provide the alcohol or with chromium agents to the ketone. The ketone can serve as a electrophile with Wittig reagents, organometallic agents or can be reacted with aldehydes under basic or acidic conditions to undergo aldol condensations. The olefins can undergo allylic oxidation with chromium or preferably selenium reagents (see Rabjohn, Org. Reactions, 1976, 24, 261) as known in the art to provide allylic alcohols which can be activated to generate a leaving group and can be substituted with carbon, oxygen, nitrogen or sulphur nucleophiles as known in the art under neutral or basic conditions with or without palladium or lewis acid catalysis. Additional compounds can be prepared by treatment of the olefin with a aryl or alkenyl halide or triflate in the presence of a palladium catalyst to undergo a Heck reaction (for an extensive reveiw of bond formation using palladium catalysis see Tsuji, Palladium Reagents and Catalysis, Wiley, 1995). The formed olefin can be funtionalized as described above to provide additional substitution. The olefin can be epoxidized with MCPBA or a related peroxide to for the epoxide that can be substutued in the presence or absence or a lewis acid with a reactive Carbon, nitrogen, oxygen or sulphur nucleophil as known in the art.

Alternatively, substituted urea derivatives can be prepared by reacting the isocyanate intermediate formed in the Curtius rearrangement by using an amine ($HNR^{31}R^{32}$) in place of the alcohol ($R^{30}$—OH) (Scheme IV).

SCHEME IV

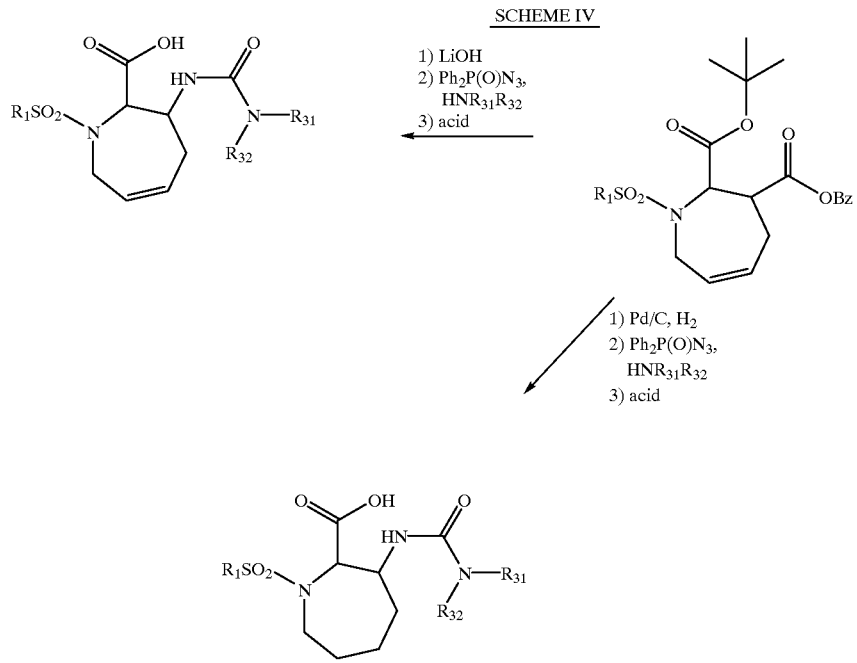

SCHEME V

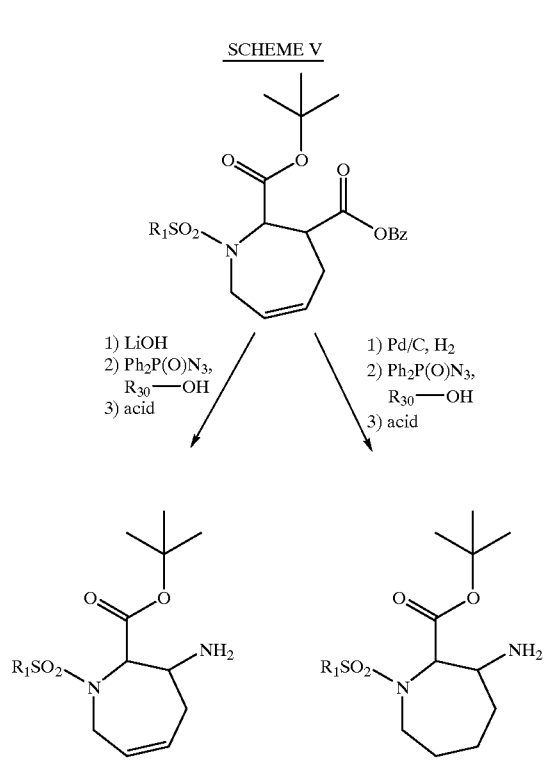

SCHEME VI

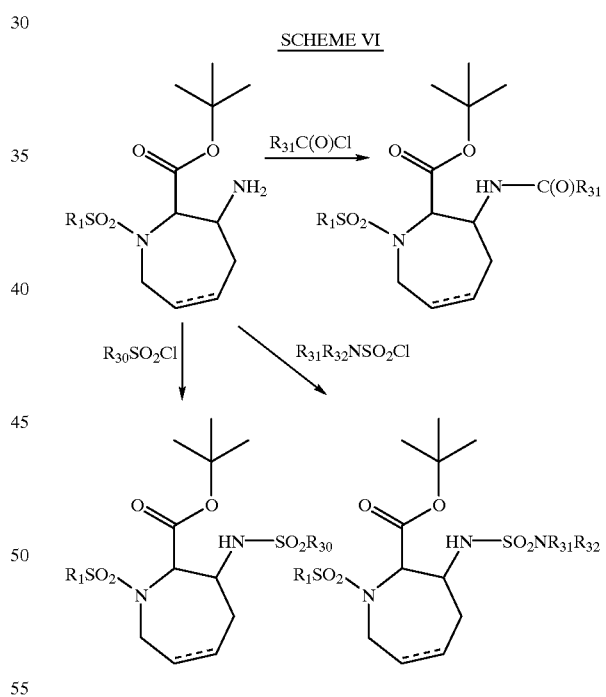

Further, the carbamate formed in Scheme III can be hydrolyzed in acid to the free amine (Scheme V) which can then be derivatized, such as by alkylation, reductive alkylation, sulfonylation, aminosulfonylation, acylated and the like, such as in Scheme VI.

It is apparent from the above description that no single general synthesis can be used in the preparation of all of the novel compounds of this invention, because some of the radicals, well known to those skilled in the art, will or may have the potential of interfering with, competing with or inhibiting the some of the reactions involved in the pathway. However, one skilled in the art is fully aware of appropriate point in the synthetic pathway when a radical may be introduced and when protecting groups can be used.

Sulfonyl halides can be prepared by the reaction of a suitable alkyl, aryl, heteroaryl, heterocyclyl and the like Grignard or lithium reagents with sulfuryl chloride, or sulfur dioxide followed by oxidation with a halogen, preferably chlorine. Alkyl, heteroaryl, heterocyclyl, aryl and the like Grignard or lithium reagents can be prepared from their corresponding halide (such as chloro or bromo) compounds which are commercially available or readily prepared from commercially available starting materials using known methods in the art. Alternatively, mercaptans may be oxidized to sulfonyl chlorides using chlorine in the presence of water under carefully controlled conditions. Additionally, sulfonic acids may be converted into sulfonyl halides using reagents such as $PCl_5$, $SOCl_2$, $ClC(O)C(O)Cl$ and the like, and also to anhydrides using suitable dehydrating reagents. The sulfonic acids are either commercially available or may be prepared using procedures well known in the art from commercially available starting materials. In place of the sulfonyl halides, sulfinyl halides or sulfenyl halides can be utilized to prepare compounds wherein the sulfonyl moiety is replaced by an sulfinyl or thio moiety, respectively. Arylsulfonic acids, benzo fused heterocyclyl sulfonic acids or heteroaryl sulfonic acids can be prepared by sulfonation of the aromatic ring by well known methods in the art, such as by reaction with sulfuric acid, $SO_3$, $SO_3$ complexes, such as $DMF(SO_3)$, $pyridine(SO_3)$, N,N-dimethylacetamide $(SO_3)$, and the like. Preferably, such sulfonyl halides are prepared from such aromatic compounds by reaction with $DMF(SO_3)$ and $SOCl_2$ or $ClC(O)C(O)Cl$. The reactions may be performed stepwise or in a single pot.

Additional R1 substitution can be obtained by further reactions on the sulfonamide after reaction of the sulfonyl halide with the related amine. For instance, nitro substituted aryl or heteroaryl sulphonamides can be reduced to the aniline and substituted or converted to the diazonium salt and reacted further to provide the described compounds by methods known to one skilled in the art. Additional R1 substitutions can be obtained by reaction of fluorine, halogen, or trifluoromethanesulfonyloxy substituted aryl or heteroaryl or alkyl sulfonyl chlorides with the related amine followed by substitution of the reactive intermediate with oxygen, nitrogen, sulfur or carbon nucleophile in the presence or absence of a transition metal catalyst such as palladium to provide the desired compounds.(For a monograph on the topic, see Miller, Aromatic Nucleophilic Substitution, Elsevier, N.Y., 1968).

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The compounds of the invention may be produced in racemic or optically pure form. When a single enantiomer is prepared, these may be synthesized by beginning with optically pure starting materials, by resolution of a basic or acidic racemic intermediate with the appropriate chiral acid or base respectivily, as known to one skilled in the art, or by the addition of a chiral protecting group to the racemic intermediate or final product where the diasteriomeric pair can be seperated by chromatoraphy or crystallization.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Prodrugs of the compounds of this invention are also contemplated by this invention. A prodrug is an active or inactive compound that is modified chemically through in vivo physiological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on a Bruker nuclear magnetic resonance spectrometer.

The following Examples illustrate the preparation of compounds of the present invention and intermediates useful in preparing the compounds of the present invention.

EXAMPLE 1

Example 1

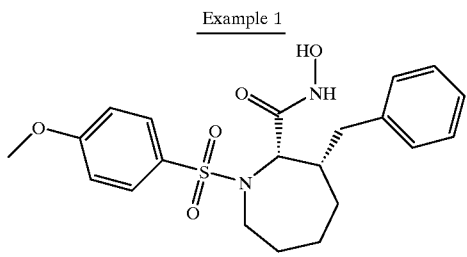

Preparation of cis-3-Benzyl-1-(4-methoxybenzenesulfonyl)-azepane-2-hydroxamic acid Step A. 2-Benzyl-6-oxo-cyclohexane carboxylic acid ethyl ester To a cooled (−78° C.) suspension of copper cyanide (1.02 g, 11.4 mmol) in 25-mL of anhydrous tetrahydrofuran was added benzylmagnesium chloride (6.2 mL of a 2.0 M solution in tetrahydrofuran, 12.5 mmol) dropwise over fifteen minutes with stirring under Argon. The bath temperature was allowed to warm to −60° C. over 45 minutes. A solution of 2-cyclohexenone (1.0 g, 10.4 mmol) in 10-mL of anhydrous tetrahydrofuran was cooled to −78° C., then added via cannula to the cuprate solution. The reaction was stirred at −78° C. for one hour then allowed to slowly warm to 0° C. The reaction solution was cooled to −78° C. and ethylchloroformate (1.24 g, 11.4 mmol) was added dropwise. The reaction was then allowed to warm slowly to room temperature and react for 18 hours. The reaction was diluted with 250-mL of methylene chloride and quenched with a solution of ammonium chloride buffered to pH 8 with ammonium hydroxide. The aqueous layer was extracted with another portion of methylene chloride. The combined organic phases were washed with water, brine, dried over sodium sulfate, filtered and concentrated to leave a viscous oil. Chromatography (silica gel, gradient of 1%–2.5% ethyl acetate in hexanes) afforded a mixture of diastereomers ((M+H)$^+$ 261.1, (M+NH$_4$)$^+$ 278.1).

Step B. 3-Benzyl-7-oxo-azepane-2-carboxylic acid ethyl ester

A solution of 2-benzyl-6-oxo-cyclohexane carboxylic acid ethyl ester (4.96 g, 19.1 mmol) in 160-mL of chloroform was added cooled to 0° C. on ice. Methanesulfonic acid (18.3 g, 190 mmol) was added in one portion and the solution allowed to equilibrate. Sodium azide (6.18 g, 95 mmol) was added in three portions over 10 minutes. After the addition was complete the reaction mixture was heated to reflux for 30 minutes. The reaction was diluted with 200-mL of chloroform and a 5% solution of sodium bicarbonate was carefully added until effervescence ceased. The aqueous layer was extracted with a second 100-mL portion of chloroform. The combined organic layers were washed with 5% sodium bicarbonate, brine, dried over sodium sulfate, filtered and concentrated to leave a mobile yellow oil. Chromatography (silica gel, 0–1% methanol in methylene chloride) afforded two pure diastereomers (cis and trans, (M+H)$^+$ 276.1) and mixed fractions.

Step C. cis-(3-Benzyl-azepan-2-yl)-methanol cis-3-Benzyl-7-oxo-azepane-2-carboxylic acid ethyl ester (0.46 g, 1.66 mmol) was charged into a 100-mL flame dried and argon flushed round bottom flask. 20-mL of anhydrous tetrahydrofuran was added and the solution cooled to 0° C. Lithium aluminum hydride (2.7 mL of 1.0M solution in tetrahydofuran, 2.7 mmol) was added dropwise. The reaction was heated to reflux and allowed to react for 18 hours. The solution was cooled to 0° C. then sodium sulfate-decahydrate was added in portions and the suspension stirred for 30 minutes. The suspension was filtered through a glass fiber filter to leave a clear solution which was concentrated in vacuo to leave a mobile yellow oil ((M+H)$^+$ 220.3) which was used without further purification.

Step D. cis-(3-Benzyl-1-(4-methoxybenzenesulfonyl)-azapan-2-yl)-methanol

A solution of cis-(3-Benzyl-azepan-2-yl)-methanol (282 mg, 1.29 mmol) in 10-mL of anhydrous methylene chloride was cooled to 0° C. Triethylamine (143 mg, 1.41 mmol) was added then 4-methoxybenzenesulfonyl chloride (280 mg, 1.35 mmol). The reaction was warmed to room temperature and allowed to react for 2 hours. 20-mL of methylene chloride was added and the crude reaction mixture washed twice with 5% sodium bicarbonate, once with brine, dried over sodium sulfate, filtered and concentrated in vacuo to leave an orange oil which was chromatographed (silica gel, 0–5% methanol in methylene chloride) to afford the pure product ((M+H)$^+$ 390.2, (M+NH$_4$)$^+$ 407.2).

Step E. cis-3-Benzyl-1-(4-methoxybenzenesulfonyl)-azepane-2-carboxylic acid

A solution of cis-(3-Benzyl-1-(4-methoxybenzene sulfonyl)-azapan-2-yl)-methanol(215 mg, 0.55 mmol) in 6.0 mL of acetone was added was cooled to 0° C. 1.0-mL of Jones reagent (Feiser and Feiser, Reagents for Organic Synthesis, Vol 1, p. 142, 1967) was added. The reaction was allowed to warm to room temperature then stirred for one hour. 20-mL of ethyl acetate was added followed by 10-mL of 10% sodium bisulfite. The layers were separated and the aqueous phase extracted with another portion of ethyl acetate. The acid was extracted twice with 0.1N sodium hydroxide then washed with ethyl acetate. The aqueous solution was reacidified to pH 3 with 1 M hydrochloric acid, extracted twice with ethyl acetate, dried over sodium sulfate, filtered, and concentrated in vacuo to leave a clear colorless oil which was used without further purification.

Step F. cis-3-Benzyl-1-(4-methoxybenzenesulfonyl)-azepane-2-hydroxamic acid cis-3-Benzyl-1-(4-methoxybenzenesulfonyl)-azepane-2-carboxylic acid (146 mg, 0.36 mmol) was dissolved in 4-mL of anhydrous methylene chloride. Dimethylformamide (10-µL) was added followed by oxalyl chloride (0.36-mL of a 2.0 M solution, 0.72 mmol). The reaction was allowed to stir at room temperature for 30 minutes. In a separate flask, 2.0-mL of tetrahydrofuran was used to suspend hydroxylamine hydrochloride (125 mg, 1.8 mmol). 0.2-mL of water was added to dissolve the mixture. The solution was cooled on ice then triethylamine (290 mg, 2.88 mmol) was added. This solution was stirred at 0° C. for 30 minutes. The acid chloride solution was then added and the reaction stirred at 0° C. for an additional 30 minutes. 20-mL of ethyl acetate was added followed by 20-mL of 0.25 M hydrochloric acid. The layers were separated and the aqueous phase was extracted with another 20-mL of ethyl acetate. The combined organic phases were washed with brine, dried over sodium sulfate, filtered, and concentrated to leave a clear colorless oil which was chromatographed (silica gel, 0–1% methanol in methylene chloride) to afford the title compound ((M+H)$^+$ 419.2, (M+NH$_4$)$^+$ 436.2).

EXAMPLE 2

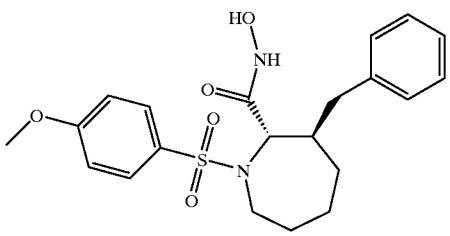

Preparation of trans-3-Benzyl-1-(4-methoxybenzenesulfonyl)-azepane-2-hydroxamic acid trans-3-Benzyl-1-(4-methoxybenzenesulfonyl)-azepane-2-carboxylic acid-hydroxyamide was synthesized from trans-3-Benzyl-7-oxo-azepane-2-carboxylic acid ethyl ester using the procedures for the preparation of cis-3-Benzyl-1-(4-methoxybenzenesulfonyl)-azepane-2-carboxylic acid-hydroxyamide.

EXAMPLE 3

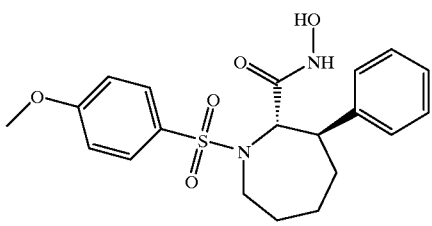

Preparation of trans-3-Phenyl-1-(4-methoxybenzenesulfonyl)-azepane-2-hydroxamic acid Step A. 2-Phenyl-6-oxo-azepane 2-carboxylic acid ethyl ester Copper cyanide (1.6 g, 17.8 mmol) was charged into a round bottomed flask and carefully flame dried under reduced pressure. The flask was then vented to argon and the process repeated two more times. 50-mL of anhydrous ether was added and the suspension cooled to −78° C. Phenyllithium (19.9-mL of 1.8 M in cyclohexanes, 35.8 mmol) was added dropwise. The reaction was allowed to warm to −60° C. over 30 minutes then cooled back down to −78° C. 6-Oxo-cyclohex-1-enecarboxylic acid ethyl ester (2.5 g, 14.9 mmol, prepared by the method of Reich et al, J. Amer. Chem Soc. 97, 19, pp.5434–5447, 1975) was dissolved in 7.5-mL of anhydrous ether, cooled to −78° C. and added to the cuprate solution via canula. The reaction was allowed to warm slowly to room temperature. 50-mL of ether was added to the reaction mixture and the reaction then quenched by addition of 50-mL of 2.0 M ammonium chloride. The layers were separated and the organic phase washed with another portion of ammonium chloride, brine, dried over sodium sulfate, filtered and concentrated in vacuo. The residue was chromatographed (silica gel, 1%–5% gradient of ethyl acetate in hexanes) to yield a mixture of diastereomers ((M+H)$^+$ 247.1, (M+NH$_4$)$^+$ 264.1).

Step B-F. trans-3-Phenyl-1-(4-methoxybenzenesulfonyl)-azeiane-2-hydroxamic acid trans-3-Phenyl-1-(4-methoxybenzenesulfonyl)-azepane-2-hydroxamic acid was synthesized from 2-Phenyl-6-oxo-azepane 2-carboxylic acid ethyl ester in the same manner as the procedures used for the preparation of cis-3-Benzyl-1-(4-methoxybenzenesulfonyl)-azepane-2-carboxylic acid-hydroxyamide.

EXAMPLE 4

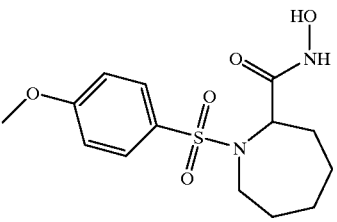

Preparation of 1-(4-methoxybenzenesulfonyl)-azepane-2-hydroxamic acid 1-(4-Methoxybenzenesulfonyl)-azepane-2-hydroxamic acid was synthesized from 6-oxo-cyclohexane carboxylic acid ethyl ester in the same manner as the procedures used for the preparation of cis-3-Benzyl-1-(4-methoxybenzene sulfonyl)-azepane-2-carboxylic acid-hydroxyamide.

EXAMPLE 5

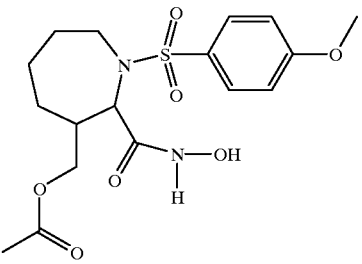

Preparation of Acetic acid 2-hydroxycarbamoyl-1-(4-methoxy-benzenesulfonyl)-azepan-3-ylmethyl ester Step A: 3-Hydroxymethyl-1-(4-methoxy-benzenesulfonyl)-azepane-2-carboxylic acid tert-butyl ester To a solution of 1-(4-Methoxy-benzenesulfonyl)-azepane-2,3-dicarboxylic acid 2-tert-butyl ester (1.06 g, 2.56 mmoL) in 12.8 mL THF at 0° C. was added a Borane-THF solution (1M, 6.4 mL) dropwise. The reaction was warmed to ambient temperature after 30 minutes and allowed to stir for 20 hours before cooling to ice bath temperature and carefully quenching with a 1:1 solution of acetic acid and water. This solution was stirred for 1 hour after which the majority of the solvent was removed under reduced pressure. The residue was dissolved in ethyl acetate and washed with brine. This solution was dried over anhydrous magnesium sulfate and filtered. The solvent was removed under reduced pressure and purified by column chromatography (silica: 25% to 30% ethyl acetate in hexanes) to yield 3-Hydroxymethyl-1-(4-methoxy-benzenesulfonyl)-azepane-2-carboxylic acid tert-butyl ester as a clear oil; MS: (M+H)$^+$=400, (M+NH$_4$)$^+$=417; and the cooresponding aldehyde (31 mg, 3%) as a clear oil; MS: (M+H)$^+$=398, (M+NH$^4$)$^+$=415.

Step B: 3-Acetoxymethyl-1-(4-methoxy-benzenesulfonyl)-azepane-2-carboxylic acid tert-butyl ester To a solution of 3-Hydroxymethyl-1-(4-methoxy-benzenesulfonyl)-azepane-2-carboxylic acid tert-butyl ester (0.5 g, 1.25 mmoL) in 6.3 mL dichlormethane was added triethylamine (0.19 mL, 1.38 mmoL) and dimethylaminopyridine (15 mg, 0.125 mmoL). This solution was cooled to 0° C. and acetic anhydride (0.18 ml, 1.88 mmoL) was added in at once. After 5 minutes the reaction was diluted with dichloromethane and washed sequentially with 0.5N HCl, water, and brine. The organic layer was dried over anhydrous magnesium sulfate and filtered. The solvent was removed under reduced pressure to yield 3-Acetoxymethyl-1-(4-methoxy-benzenesulfonyl)-azepane-2-carboxylic acid tert-butyl ester; MS: $(M+H)^+=442$, $(M+NH_4)^+=459$.

Step C: 3-Acetoxymethyl-1-(4-methoxy-benzenesulfonyl)-azepane-2-carboxylic acid

To a solution of 3-Acetoxymethyl-1-(4-methoxy-benzenesulfonyl)-azepane-2-carboxylic acid tert-butyl ester (266 mg, 0.6 mmoL) in 1.5 mL dichloromethane at 0° C. was added 1.5 mL of trifluoroacetic acid. The reaction was gradually allowed to warm to ambient temperature, and the solvent was removed under reduced pressure after 1.4 hours. The residue was azeotroped twice with toluene and purified by column chromatography (silica: 30% ethyl acetate in hexanes with 1% acetic acid to 4% methanol in dichloromethane with 1% acetic acid) to yield 3-Acetoxymethyl-1-(4-methoxy-benzenesulfonyl)-azepane-2-carboxylic acid quantitatively; MS: $(M+H)^+=386$, $(M+NH_4)^+=403$.

Step D: Acetic acid 2-hydroxycarbamoyl-1-(4-methoxy-benzenesulfonyl)-azepan-3-ylmethyl ester To a solution of 3-Acetoxymethyl-1-(4-methoxy-benzenesulfonyl)-azepane-2-carboxylic acid (107 mg, 0.28 mmoL) in 5.6 mL dichloromethane was added N,N-Diisopropyl ethyamine (0.195 mL, 1.12 mmoL). This solution was cooled to 0° C. and Hydroxyl amine (58.4 mg, 0.84 mmoL) was added followed by PyBroP (155 mg, 0333 mmoL). The reaction was warmed to ambient temperature after 15 minutes and was stopped after 5.5 hours. The residue was diluted with ethyl acetate and washed sequentially with 0.5N HCl, and brine. The organic layer was dried over anhydrous magnesium sulfate and filtered. The solvent was evaporated under reduced pressure and the residue was purified by column chromatography (silica: 0.5% to 1.5% methanol in dichloromethane) to yield Acetic acid 2-hydroxycarbamoyl-1-(4-methoxy-benzene sulfonyl)-azepan-3-ylmethyl ester; MS: $(M-H)^-=399$.

EXAMPLE 6

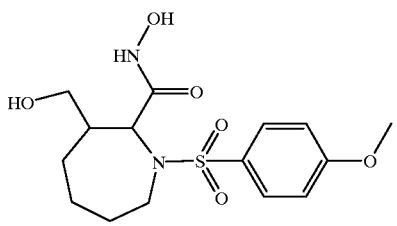

Preparation of 3-Hydroxymethyl-1-(4-methoxy-benzenesulfonyl)-azepane-2-carboxylic acid hydroxamide To a solution of Acetic acid 2-hydroxycarbamoyl-1-(4-methoxy-benzenesulfonyl)-azepan-3-ylmethyl ester in 1.1 mL methanol was added 0.1 mL of 1.0 M LiOH in water at ambient temperature. The reaction was stopped after 30 minutes by evaporating the solvent under reduced pressure. The residue was taken up in water and washed twice with diethyl ether, followed by acidification of the water to pH=1 with 1N HCl. The water layer was extracted twice with ethyl acetate which was dried over anhydrous magnesium sulfate and filtered. The solvent was evaporated under reduced pressure and was purified with column chromatography (silica: 2% to 8% methanol in dichloromethane) to yeild a thin film which was freeze-dried to yield 3-Hydroxymethyl-1-(4-methoxy-benzenesulfonyl)-azepane-2-carboxylic acid hydroxamide as a white lyopholate; MS: $(M-H)^-=357$.

EXAMPLE 7

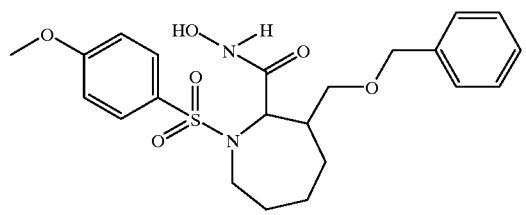

Preparation of 3-Benzyloxymethyl-1-(4-methoxy-benzenesulfonyl)-azeoane-2-carboxylic acid hydroxyamide Step A: 3-Benzyloxymethyl-1-(4-methoxy-benzenesulfonyl)-azepane-2-carboxylic acid To a solution of 3-Hydroxymethyl-1-(4-methoxy-benzenesulfonyl)-azepane-2-carboxylic acid tert-butyl ester (110 mg, 0.275 mmoL) in 3.9 mL cyclohexane and 1.95 mL of dichloromethane was added benzyl trichloracetimidate (0.1 mL, 0.55 mmoL). The solution was cooled to 0° C. and trifluoromethane sulfonic acid (0.008 mL, 0.091 mmoL) was added in. After 2.5 hours the reaction was filtered and the cake was washed with a 2:1 solution of cyclohexane and dichloromethane, the solvent was evaporated under reduced pressure and the residue was taken up in ethyl acetate. The solution was washed sequentially with dilute sodium bicarbonate and brine. The organic layer was dried over anhyrous magnesium sulfate, filtered, and the solvent evaporated under reduced pressure. The residue was purified by column chromatography (silica: 30% ethyl acetate in hexanes to 5% methanol in dichloromethane) to yield 3-Benzyloxymethyl-1-(4-methoxy-benzenesulfonyl)-azepane-2-carboxylic acid; MS: $(M+H)^+=434$, $(M-H)^-=432$.

Step B: 3-Benzyloxymethyl-1-(4-methoxy-benzenesulfonyl)-azepane-2-carboxylic acid benzhydryloxy-amide To a solution of 3-Benzyloxymethyl-1-(4-methoxybenzene sulfonyl)-azepane-2-carboxylic acid (19 mg, 0.044 mmoL) in 0.63 mL of dimethylformamide was added 1-Hydroxy-benzotriazole hydrate (7.1 mg, 0.0525 mmoL) and O-Benzhydryl-hydroxylamine (10.4 mg, 0.0525 mmoL). This solution was cooled to 0° C. and 1-(3-Dimethylamino propyl)-3-ethylcarbodiimide hydrochloride (10 mg, 0.0525 mmoL) was added in. The reaction was warmed to ambient temperature after 20 minutes, and the reaction was stopped after 3 hours by diluting with ethyl acetate. This solution was washed sequentially with saturated sodium bicarbonate, 0.5N HCl, and brine. The organic layer was dried over anhydrous magnesium sulfate, filtered, and the solvent removed under reduced pressure. The residue was purified by column chromatography (silica: 20% to 30% ethyl acetate in hexanes) to yield 3-Benzyloxymethyl-1-(4-methoxy-benzenesulfonyl)-azepane-2-carboxylic acid benzhydryloxy-amide; MS: $(M+H)^+=615$, $(M+NH_4)^+=632$.

Step C: 3-Benzyloxymethyl-1-(4-methoxy-benzenesulfonyl)-azepane-2-carboxylic acid hydroxyamide To a solution of 3-Benzyloxymethyl-1-(4-methoxy-benzenesulfonyl)-azepane-2-carboxylic acid benzhydryloxy-amide (10 mg, 0.016 mmoL) in 0.25 mL of dichloromethane at 0° C. was added 0.25 mL of trifluoroacetic acid followed by triethyl silane (3.7 mg, 0.032 mmoL). After 50 minutes the solvent was removed under reduced pressure and the residue was azeotroped twice with toluene. The residue was then purified by column chromatography (silica: 1.5% to 3% methanol in dichloromethane) to yield 3-Benzyloxymethyl-1-(4-methoxy-benzenesulfonyl)-azepane-2-carboxylic acid hydroxyamide; MS: (M−H)⁻=447.

EXAMPLE 8

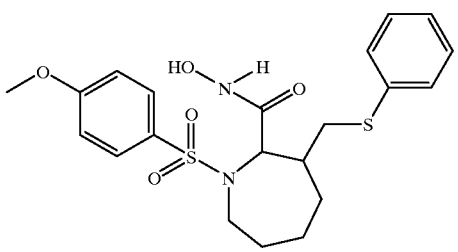

Preparation of 1-(4-Methoxy-benzenesulfonyl)-3-phenylsulfanylmethyl-azepane-2-carboxylic acid hydroxyamide Step A: 1-(4-Methoxy-benzenesulfonyl)-3-phenyl sulfanylmethyl-azepane-2-carboxylic acid tert-butyl ester To a solution of 3-Hydroxymethyl-1-(4-methoxy-benzenesulfonyl)-azepane-2-carboxylic acid tert-butyl ester (0.2 mg, 0.5 mmoL) in 6 mL of ethylene glycol dimethyl ether was added Diphenyl disulfide (0.55 g, 2.503 mmoL) and Tributyl phosphine (0.624 mL, 2.503 mmoL). The reaction was heated to reflux and cooled to ambient temperature after 20 minutes. The solvent was removed under reduced pressure, the residue dissolved in ethyl acetate and washed with brine. The organic layer was dried over anhydrous magnesium sulfate, and the solvent was removed under reduced pressure. The residue was purified by column chromatography (silica: 5% to 20% ethyl acetate in hexanes) to yield (0.110 g, 45%) of 1-(4-Methoxy-benzenesulfonyl)-3-phenylsulfanylmethyl-azepane-2-carboxylic acid tert-butyl ester; MS: (M+H)⁺⁼492, (M+NH₄)⁺=509.

Step B: 1-(4-Methoxy-benzenesulfonyl)-3-phenyl sulfanylmethyl-azenane-2-carboxylic acid hydroxyamide 1-(4-Methoxy-benzenesulfonyl)-3-phenylsulfanylmethyl-azepane-2-carboxylic acid hydroxyamide was synthesized from 1-(4-Methoxy-benzenesulfonyl)-3-phenylsulfanyl methyl-azepane-2-carboxylic acid tert-butyl ester in the same manner as the procedures used for the preparation of Acetic acid 2-hydroxycarbamoyl-1-(4-methoxybenzene sulfonyl)-azepan-3-ylmethyl ester: MS (M+H)⁺=451, (M+NH₄)⁺=468.

EXAMPLE 9

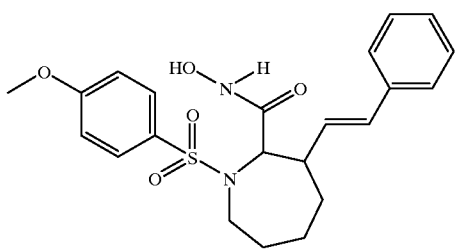

Preparation of 1-(4-Methoxy-benzenesulfonyl)-3-styryl-azepane-2-carboxylic acid hydroxyamide Step A: 3-Formyl-1-(4-methoxy-benzenesulfonyl)-azepane-2-carboxylic acid tert-butyl ester To a solution of Hydroxymethyl-1-(4-methoxy-benzene sulfonyl)-azepane-2-carboxylic acid tert-butyl ester (0.5 g, 1.25 mmoL) in 1.25 mL in THF was added sodium bromide (19 mg, 0.19 mmoL). This suspention was cooled to 0° C. and TEMPO (25 mg, 5%) was added in followed by 1.41 mL of a 0.129M solution of sodium bicarbonate in Clorox bleach. The magnetic stirring was increased to obtain a biphasic solution and kept at that rate for three hours while the reaction gradually warmed to ambient temperature. The reaction was then quenched with sodium sulfite (1.26 g). After 20 minutes water and ethyl acetate were added in, the layers were separated, and the organic layer was dried over anhydrous magnesium sulfate and filtered. The solvent removed under reduced pressure, and the residue was purified by column chromatography (silica: 15% to 25% ethyl acetate in hexanes) to yield 3-Formyl-1-(4-methoxy-benzenesulfonyl)-azepane-2-carboxylic acid tert-butyl ester; MS: (M+H)⁺=398, (M+NH₄)⁺=415.

Step B: 1-(4-Methoxy-benzenesulfonyl)-3-styryl-azepane-2-carboxylic acid tert-butyl ester To a solution of Benzyl triphenylphosphonium bromide (229 mg, 0.528 mmoL) in 2 mL of THF at 0° C. was added 2.0M butyl lithium solution (0.272 mL) in pentane. After five minutes the solution was warmed to ambient temperature, and kept at that temperature for 30 minutes before adding in the 3-Formyl-1-(4-methoxy-benzene sulfonyl)-azepane-2-carboxylic acid tert-butyl ester (200 mg, 0.503 mmoL) dissolved in 1.52 mL of THF. After 20 hours the reaction was quenched by adding water dropwise, the reaction was diluted with ethyl acetate and washed twice with brine. The organic layer was dried over anhydrous magnesium sulfate, filtered, and the solvent evaporated under reduced pressure. The residue was purified by column chromatography (silica: 20% to 25% ethyl acetate in hexanes) to yield 1-(4-Methoxy-benzenesulfonyl)-3-styryl-azepane-2-carboxylic acid tert-butyl ester; MS: (M+H)⁺= 472, (M+NH₄)⁺=489.

Step C: 1-(4-Methoxy-benzenesulfonyl)-3-styryl-azepane-2-carboxylic acid 1-(4-Methoxy-benzenesulfonyl)-3-styryl-azepane-2-carboxylic acid was synthesized from 1-(4-Methoxy-benzenesulfonyl)-3-styryl-azepane-2-carboxylic acid tert-butyl ester in the same manner as the procedures used for the preparation of 3-Acetoxymethyl-1-(4-methoxy-benzenesulfonyl)-azepane-2-carboxylic acid: MS (M+H)⁺= 416, (M+NH₄)⁺=433.

Step D: 1-(4-Methoxy-benzenesulfonyl)-3-styryl-azepane-2-carboxylic acid hydroxyamide 1-(4-Methoxy-benzenesulfonyl)-3-styryl-azepane-2-carboxylic acid hydroxyamide was synthesized from 1-(4-

Methoxy-benzenesulfonyl)-3-styryl-azepane-2-carboxylic acid in the same manner as the procedures used for the preparation of 3-Benzyloxymethyl-1-(4-methoxy-benzenesulfonyl)-azepane-2-carboxylic acid hydroxyamide: MS $(M+H)^+=431$, $(M+NH_4)^+=448$, $(M-H)^-=429$.

EXAMPLE 10

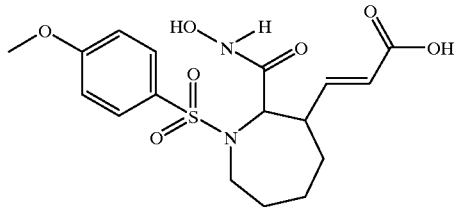

Preparation of 3-(2-Hydroxycarbamoyl-1-(4-methoxy-benzenesulfonyl)-azepan-3-yl)-acrylic acid Step A: 3-(2-Ethoxycarbonyl-vinyl)-1-(4-methoxybenzene sulfonyl)-azepane-2-carboxylic acid tert-butyl ester To a solution of 3-Formyl-1-(4-methoxy-benzenesulfonyl)-azepane-2-carboxylic acid tert-butyl ester (310 mg, 0.78 mmoL) in 8.1 mL benzene was added (Carboethoxymethylene) triphenylphosphorane (408 mg, 1.17 mmoL) at ambient temperature. An additional 310 mg was added after 24 hours, after which the reaction was allowed to proceed for 72 hours. The solvent was evaporated under reduced pressure and the residue was purified by column chromatograph (silica: 18% to 25% ethyl acetate in hexanes) to yield 3-(2-Ethoxycarbonyl-vinyl)-1-(4-methoxy-benzenesulfonyl)-azepane-2-carboxylic acid tert-butyl ester; MS: $(M+H)^+=468$, $(M+NHY_4)^-=485$.

Step B: 3-(2-Hydroxycarbamoyl-1-(4-methoxy-benzenesulfonyl)-azepan-3-yl)-acrylic acid ethyl ester 3-(2-Hydroxycarbamoyl-1-(4-methoxy-benzenesulfonyl)-azepan-3-yl)-acrylic acid ethyl ester was synthesized from 3-(2-Ethoxycarbonyl-vinyl)-1-(4-methoxybenzene sulfonyl)-azepane-2-carboxylic acid tert-butyl ester in the same manner as the procedures used for the preparation of Acetic acid 2-hydroxycarbamoyl-1-(4-methoxy-benzenesulfonyl)-azepan-3-ylmethyl ester: MS $(M+H)^+=427$.

Step C: 3-(2-Hydroxycarbamoyl-1-(4-methoxy-benzenesulfonyl)-azepan-3-yl)-acrylic acid To a solution of 3-(2-Hydroxycarbamoyl-1-(4-methoxy-benzenesulfonyl)-azepan-3-yl)-acrylic acid ethyl ester (41 mg, 0.096 mmoL) in 0.96 mL THF and 1.1 mL water was added lithium hydroxide (12 mg, 0.288 mmoL) at ambient temperature. After 3.5 hours the reaction solvent was evaporated under reduced pressure, and the residue was diluted with water and washed twice with diethyl ether. The water layer was acidified to pH=1 and extracted twice with ethyl acetate. The organic layer was washed with brine and dried over anhydrous magnesium sulfate, filtered, and the solvent evaporated under reduced pressure. The residue was freeze dried to yield 3-(2-Hydroxycarbamoyl-1-(4-methoxy-benzenesulfonyl)-azepan-3-yl)-acrylic acid; MS: $(M+H)^+=399$, $(M+NH_4)^+=416$, $(M-H)^-=397$.

EXAMPLE 11

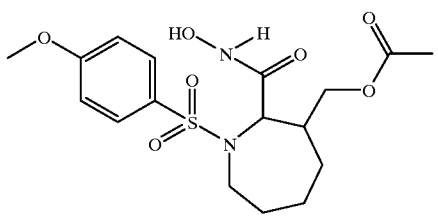

Preparation of Acetic acid 2-hydroxycarbamoyl-1-(4-methoxy-benzenesulfonyl)-2,3,4,7-tetrahydro-1H-azepin-3-ylmethyl ester Step A: 3-Hydroxymethyl-1-(4-methoxy-benzenesulfonyl)-2,3,4,7-tetrahydro-1H-azepine-2-carboxylic acid tert butyl ester To a stirred solution of 1-(4-Methoxy-benzenesulfonyl)-2,3,4,7-tetrahydro-1H-azepine-2,3-dicarboxylic acid 2-tert-butyl ester (1.17 g, 2.65 mmoL) in 26.5 mL THF at 0° C. was added triethylamine (0.406 mL, 2.915 mmoL) followed by isobutyl chloroformate (0.378 mL, 2.915 mmoL). This suspention was allowed to stir for one hour. The suspension was then filtered into a dropping funnel which was added dropwise to a previously prepared sodium borohydride (321 mg, 8,48 mmoL) solution in 1.63 mL of water at 0° C. After 2.5 hours the solvent was stripped and the residue was diluted with ethyl acetate and water. The solution was washed once with 0.5N HCL, the layers separated, and the organic layer was dried over anhydrous magnesium sulfate. The solvent was evaporated under reduced pressure and the residue was purified by column chromatography (silica: 25% to 35% ethyl acetate in hexanes) to yield 3-Hydroxymethyl-1-(4-methoxy-benzenesulfonyl)-2,3,4,7-tetrahydro-1H-azepine-2-carboxylic acid tert butyl ester; MS: $(M+H)^+=398$, $(M+NH_4)^+=415$.

Step B: 3-Acetoxymethyl-1-(4-methoxy-benzenesulfonyl)-2,3,4,7-tetrahydro-1H-azepine-2-carboxylic acid 3-Acetoxymethyl-1-(4-methoxy-benzenesulfonyl)-2,3,4,7-tetrahydro-1H-azepine-2-carboxylic acid was synthesized from 3-Hydroxymethyl-1-(4-methoxy-benzenesulfonyl)-2,3,4,7-tetrahydro-1H-azepine-2-carboxylic acid tert butyl ester in the same manner as the procedures used for the preparation of 3-Acetoxymethyl-1-(4-methoxy-benzenesulfonyl)-azepane-2-carboxylic acid: MS $(M-H)^-=382$.

Step C: Acetic acid 2-hydroxycarbamoyl-1-(4-methoxy-benzenesulfonyl)-2.3,4,7-tetrahydro-1H-azepin-3-ylmethyl ester To a solution of 3-Acetoxymethyl-1-(4-methoxy-benzenesulfonyl)-2,3,4,7-tetrahydro-1H-azepine-2-carboxylic acid (101 mg, 0.263 mmoL) in 3 mL dimethylformamide at −20° C. under an argon blanket was added O-(tert-Butyldimethyl-silyl)hydroxylamine (50 mg, 0.342 mmoL) followed by N,N-Diisopropylethylamine (0.069 mL, 0.342 mmoL). (O-(7-azabenzotriazol-1-yl)-1,1,3,3-tetramethyluronium hexafluorophosphate) (110 mg, 0.289 mmoL) was added in and the temperature was kept at −20° C. for 40 minutes before allowing to warm to ambient temperature. The reaction was allowed to stir for 19 hours at which time it was diluted with ethyl acetate. 10% citric acid was added in and stirred for 30 minutes, the reaction was then washed sequentially with water, 0.5N HCL, dilute sodium bibarbonate, and brine. The organic layer was dried over anhydrous magnesium sulfate, filtered, and the solvent removed under reduced pressure. The residue was purified by column chromatography (silica: 0.5% to 3% methanol in dichloromethane) to yield (33 mg, 31%) of Acetic acid 2-hydroxycarbamoyl-1-(4-methoxy-benzenesulfonyl)-2,3,4,7-tetrahydro-1H-azepin-3-ylmethyl ester; MS: (M+H)⁺=399, (M+NH₄)⁺=416.

EXAMPLE 12

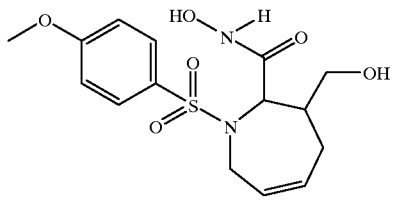

Preparation of 3-Hydroxymethyl-1-(4-methoxy-benzenesulfonyl)-2,3,4,7-tetrahydro-1H-azepine-2-carboxylic acid hydroxyamide 3-Hydroxymethyl-1-(4-methoxy-benzenesulfonyl)-2,3,4,7-tetrahydro-1H-azepine-2-carboxylic acid hydroxyamide was synthesized from Acetic acid 2-hydroxycarbamoyl-1-(4-methoxy-benzenesulfonyl)-2,3,4,7-tetrahydro-1H-azepin-3-ylmethyl ester in the same manner as the procedures used for the preparation of 3-Hydroxymethyl-1-(4-methoxybenzenesulfonyl)-azepane-2-carboxylic acid hydroxamide: MS (M−H)⁻=355.

EXAMPLE 13

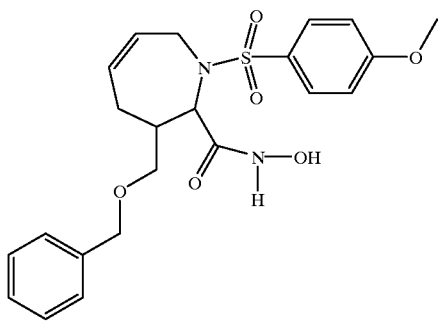

Preparation of 3-Benzyloxymethyl-1-(4-methoxy-benzenesulfonyl)-2,3,4,7-tetrahydro-1H-azepine-2-carboxylic acid hydroxyamide Step A: 3-Benzyloxymethyl-1-(4-methoxy-benzenesulfoyl)-2,3,4,7-tetrahydro-1H-azepine-2-carboxylic acid tert-butyl ester 3-Benzyloxymethyl-1-(4-methoxy-benzenesulfoyl)-2,3,4,7-tetrahydro-1H-azepine-2-carboxylic acid tert-butyl ester was synthesized from 3-Hydroxymethyl-1-(4-methoxy-benzenesulfonyl)-2,3,4,7-tetrahydro-1H-azepine-2-carboxylic acid tert butyl ester in the same manner as the procedures used for the preparation of 3-Benzyloxymethyl-1-(4-methoxy-benzenesulfonyl)-azepane-2-carboxylic acid: MS (M+H)⁺=488, (M+NH₄)⁺=505.

Step B: 3-Benzyloxymethyl-1-(4-methoxy-benzenesulfonyl)-2,3,4,7-tetrahydro-1H-azepine-2-carboxylic acid 3-Benzyloxymethyl-1-(4-methoxy-benzenesulfonyl)-2,3,4,7-tetrahydro-1H-azepine-2-carboxylic acid was synthesized from 3-Benzyloxymethyl-1-(4-methoxy-benzenesulfoyl)-2,3,4,7-tetrahydro-1H-azepine-2-carboxylic acid tert-butyl ester in the same manner as the procedures used for the preparation of ³-Acetoxymethyl-1-(4-methoxy-benzenesulfonyl)-azepane-2-carboxylic acid: MS (M−H)⁻=430.

Step C: 3-Benzyloxymethyl-1-(4-methoxy-benzenesulfonyl)-2,3,4,7-tetrahydro-1H-azepin-2-carboxylic acid hydroxyamide 3-Benzyloxymethyl-1-(4-methoxy-benzenesulfonyl)-2,3,4,7-tetrahydro-1H-azepine-2-carboxylic acid hydroxyamide was synthesized from 3-Benzyloxymethyl-1-(4-methoxy-benzene sulfonyl)-2,3,4,7-tetrahydro-1H-azepine-2-carboxylic acid in the same manner as the procedures used for the preparation of Acetic acid ²-hydroxycarbamoyl-1-(4-methoxy-benzenesulfonyl)-2,3,4,7-tetrahydro-1H-azepin-3-ylmethyl ester: MS (M+H)⁺=447, (M+NH₄)⁺=464.

EXAMPLE 14

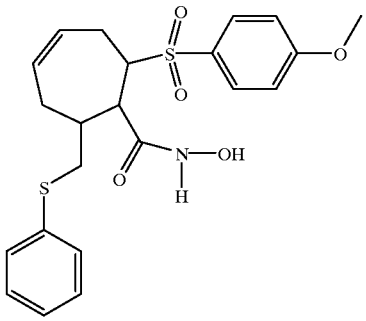

Preparation of 1-(4-Methoxy-benzenesulfonyl)-3-phenylsulfanylmethyl-2,3,4,7-tetrahydro-1H-azepine-2-carboxylic acid hydroxyamide Step A: 1-(4-Methoxy-benzenesulfonyl)-3-phenylsulfanylmethyl-2,3,4,7-tetrahydro-1H-azepine-2-carboxylic acid tert-butyl ester 1-(4-Methoxy-benzenesulfonyl)-3-phenylsulfanylmethyl-2,3,4,7-tetrahydro-1H-azepine-2-carboxylic acid tert-butyl ester was synthesized from 3-Hydroxymethyl-1-(4-methoxy-benzenesulfonyl)-2,3,4,7-tetrahydro-1H-azepine-2-carboxylic acid tert butyl ester in the same manner as the procedures used for the preparation of 1-(4-Methoxy-benzenesulfonyl)-3-phenylsulfanylmethyl-azepane-2-carboxylic acid tert-butyl ester: MS (M+H)⁺=490, (M+NH₄)⁺=507.

Step B: 1-(4-Methoxy-benzenesulfonyl)-3-phenylsulfanyl ethyl-2,3,4,7-tetrahydro-1H-azepine-2-carboxylic acid 1-(4-Methoxy-benzenesulfonyl)-3-phenylsulfanylmethyl-2,3,4,7-tetrahydro-1H-azepine-2-carboxylic acid was synthesized from 1-(4-Methoxy-benzenesulfonyl)-3-phenylsulfanylmethyl-2,3,4,7-tetrahydro-1H-azepine-2-carboxylic acid tert-butyl ester in the same manner as the procedures used for the preparation of 3-Acetoxymethyl-1-(4-methoxy-benzenesulfonyl)-azepane-2-carboxylic acid: MS (M−H)⁻=432.

Step C: 1-(4-Methoxy-benzenesulfonyl)-3-phenylsulfanyl methyl-2,3,4,7-tetrahydro-1H-azepine-2-carboxylic acid hydroxyamide 1-(4-Methoxy-benzenesulfonyl)-3-phenylsulfanylmethyl-2,3,4,7-tetrahydro-1H-azepine-2-carboxylic acid hydroxyamide was synthesized from 1-(4-Methoxy-benzenesulfonyl)-3-phenylsulfanylmethyl-2,3,4, 7-tetrahydro-1H-azepine-2-carboxylic acid in the same manner as the procedures used for the preparation of Acetic acid 2-hydroxycarbamoyl-1-(4-methoxy-benzenesulfonyl)-2,3,4,7-tetrahydro-1H-azepin-3-ylmethyl ester: MS (M+H)$^+$=449, (M+NH$_4$)$^+$=466.

EXAMPLE 15

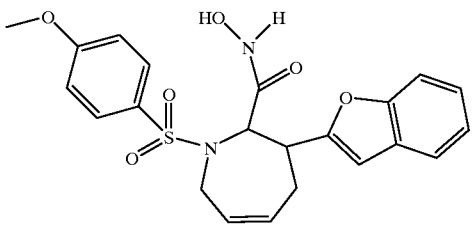

Preparation of 3-Benzofuran-2-yl-1-(4-methoxy-benzenesulfonyl)-2,3,4,7-tetrahydro-1H-azepine-2-carboxylic acid hydroxyamide Step A: 3-Benzofuran-2-yl-1-(4-methoxy-benzenesulfonyl)-2,3,4.7-tetrahydro-1H-azepine-2-carboxylic acid tert-butyl ester To a stirred solution of 1-(4-Methoxy-benzenesulfonyl)-2,3,4,7-tetrahydro-1H-azepine-2,3-dicarboxylic acid 2-tert-butyl ester (0.7 g, 1.59 mmoL) in 1.7 mL of dimethylformamide at 0° C. was added Imidazole (238 mg, 3.5 mmoL) and tert-Butyldimethlysilyl chloride (263 mg, 1.74 mmoL). The reaction was warmed to ambient temperature after one hour, and diluted with ethyl acetate after four hours. The reaction was washed sequentially with water, ammonium chloride, and brine. The organic layer was dried over anhydrous magnesium chloride, filtered and the solvent evaporated under reduced pressure. The crude was stored under high vacuum for 18 hours. The residue was then dissolved in dichlormethane and cooled to 0° C. To this solution was added catalytic dimethylformamide and (0.708 mL, 1.41 mmoL) of 2.0M oxalyl chloride. The reaction was warmed to ambient temperature after 30 minutes, and the solvent was evaporated under reduced pressure after three hours. The acid chloride was azeotroped twice with toluene and dissolved in one mL of toluene. This solution was added to a refluxing suspention of Benzene triphenylphosphine phenol (633 mg, 1.41 mmoL) and Triethylamine (0.59 mL, 4.23 mmoL) in 5.65 mL toluene. The reaction was kept at reflux for 2.5 hours and slowly cooled to ambient temperature over 18 hours. The reaction was then diluted with ethyl acetate and washed sequentially with 1N HCL, half saturated sodium bicarbonate, and brine. The organic layer was dried over anhydrous magnesium sulfate, filtered, and the solvent removed under reduced pressure. The residue was purified by column chromatography (silica: 5% to 15% ethyl acetate in hexanes) to yield 3-Benzofuran-2-yl-1-(4-methoxy-benzene sulfonyl)-2,3,4,7-tetrahydro-1H-azepine-2-carboxylic acid tert-butyl ester; MS: (M+H)$^+$=484, (M+NH$_4$)$^+$=501.

Step B: 3-Benzofuran-2-yl-1-(4-methoxy-benzenesulfonyl)-2,3,4,7-tetrahydro-1H-azepine-2-carboxylic acid 3-Benzofuran-2-yl-1-(4-methoxy-benzenesulfonyl)-2,3,4,7-tetrahydro-1H-azepine-2-carboxylic acid was synthesized from 3-Benzofuran-2-yl-1-(4-methoxy-benzenesulfonyl)-2,3,4,7-tetrahydro-1H-azepine-2-carboxylic acid tert-butyl ester in the same manner as the procedures used for the preparation of 3-Acetoxymethyl-1-(4-methoxy-benzenesulfonyl)-azepane-2-carboxylic acid: MS (M–H)$^{30}$ 426.

Step C: 1-(4-Methoxy-benzenesulfonyl)-3-phenylsulfanylmethyl-2,3,4,7-tetrahydro-1H-azepine-2-carboxylic acid hydroxyamide 1-(4-Methoxy-benzenesulfonyl)-3-phenylsulfanylmethyl-2,3,4,7-tetrahydro-1H-azepine-2-carboxylic acid hydroxyamide was synthesized from 3-Benzofuran-2-yl-1-(4-methoxy-benzenesulfonyl)-2,3,4,7-tetrahydro-1H-azepine-2-carboxylic acid in the same manner as the procedures used for the preparation of Acetic acid 2-hydroxycarbamoyl-1-(4-methoxy-benzenesulfonyl)-2,3,4,7-tetrahydro-1H-azepin-3-ylmethyl ester: MS (M–H)$^+$= 441.

EXAMPLE 16

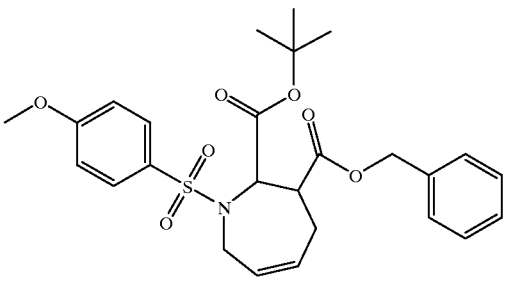

Preparation of 1-(4-Methoxy-benzenesulfonyl)-2,3,4,7-tetrahydro-1H-azepine-2,3-dicarboxylic acid 3-benzyl ester 2-tert-butyl ester Step A. 2-Aminosuccinic acid 4-benzyl ester 1-tert-butyl ester D-Aspartic acid β-benzylester (9 g, 40.3 mmol) is suspended in 75 ml Dioxane and 7.5 ml Sulfuric Acid and cooled to –15° C. 2-Methylpropene (75 ml) is added and the reaction mixture is sealed and stirred for 4 h at room temperature. The reaction mixture is then cooled to 0° C. and poured into 600 ml Diethylether and 325 ml 1M NaOH. The organic phase is separated and the water phase is extracted twice with 200 ml Diethylether. The combined organic fractions are dried with MgSO$_4$ for 30 min. and filtered. The Diethylether is evaporated and the remaining oil is dried at high vacuum for 24 hours: Cal. 280.2, found (MH)$^+$ 280.

Step B. 2-(4-Methoxy-benzenesulfonylamino)-succinic acid 4-benzyl ester 1-tert-butyl ester 2-Aminosuccinic acid 4-benzyl ester 1-tert-butyl ester (9.57 g, 33.4 mmol), Triethylamine (9.3 ml, 66.8 mmol) and 4-Methoxybenzenesulfonylchloride (6.9 g, 33.4 mmol) are solved in 50 ml Dichloromethane (DCM) and stirred at room temp. for 1 h. The reaction mixture is diluted with 50 ml DCM. 200 ml water are added and the organic phase is separated. The water phase is extracted twice with DCM. The combined organic extracts are dried with MgSO$_4$ and filtered. The solvent is evaporated and the remaining residue is recrystallized from Diethylether/Ethylacetate as white needles: $^1$H NMR (CDCl$_3$),ppm: 8.2 Hz, (d, 1H), 7.7 Hz (d, 2H), 7.3 Hz (m, 5H), 7.1 Hz (d, 2H), 5.05 Hz (d, 2H), 4.08 Hz (dd, 1H), 3.9 Hz (s, 3H), 2.72 Hz (dd, 1H), 2.59 Hz (dd, 1H) 1.21 Hz (s, 9H).

Step C. 2-Allyl-3-(4-methoxy-benzenesulfonylamino)-succinic acid 1-benzyl ester 4-tert-butyl ester 100 ml dry Tetrahydrofuran (THF) are cooled to –78° C. 1M THF-solution of Lithium bis(trimethylsilyl)amide (47.35 ml, 47.35 mmol) are added while the temperature is maintained. 2-(4-Methoxy-benzenesulfonylamino)-succinic acid 4-benzyl ester 1-tert-butyl ester (10.1 g, 22.5 mmol) are dissolved in 45 ml THF and added dropwise to the reaction solution. The reaction mixture is allowed to stir for 1 h and then warmed briefly to −40° C. After re-cooling to −78° C. Allyliodide (3.1 ml, 33.8 mmol) dissolved in 30 ml THF are added drop-wise. The reaction mixture is allowed to warm to −40° C. and is quenched with a NH$_4$Cl-solution. The organic phase is separated dried over MgSO$_4$ and filtered. The solvent is evaporated and the product is purified with a short flash-chromatography column. Hexane/Ethylacetate (9:1): Cal. 489.6 Found. (MH)$^+$ 490.

Step D. 2-Allyl-3-(allyl-(4-methoxy-benzenesulfonyl)-amino)-succinic acid 1-benzyl ester 4-tert-butyl ester Triphenylphosphine (1 g, 3.9 mmol) are solved in 60 ml Tetrahydrofuran (THF) and cooled to 0° C. Diazopropyl dicarboxylate (DIAD) (0.77 ml, 3.9 mmol) are added via syringe and the reaction mixture is stirred for 30 min. Allyl alcohol (16 μl, 0.23 mmol) is added to the yellow suspension and then after 10 min., 2-Allyl-3-(4-methoxy-benzenesulfonylamino)-succinic acid 1-benzyl ester 4-tert-butyl ester (1.4 g, 2.6 mmol) is added. The reaction mixture is stirred for 30 min. at 0° C. and is then allowed to warm to room temp. After evaporation of most of the THF and flash-chromatography with Hexane/Ethylacetate (2:1) the desired product is obtained: $^1$H NMR (CDCl$_3$ 400 MHz), ppm: 7.80 (d, 2H), 7.38 (m, 5H), 6.95 (d, 2H), 5.75 (m, 2H), 5.10 (m, 6H), 3.95 (m, 2H), 3.90 (s, 3H), 3.21 (ddd, 1H), 2.50 (ddd, 1H), 2.35 (ddd, 1H), 1.40 (s, 9H).

Step E. 1-(4-Methoxy-benzenesulfonyl)-2,3,4,7-tetrahydro-1H-azepine-2,3-dicarboxylic acid 3-benzyl ester 2-tert-butyl ester 2-Allyl-3-(allyl-(4-methoxy-benzenesulfonyl)-amino)-succinic acid 1-benzyl ester 4-tert-butyl ester (5.5 g, 10.4 mmol) are solved in 40 ml Dichloromethane and deoxygenated and flushed with Argon three times. The catalyst (RuCl$_2$(PCy$_3$)$_2$=—Ph) (100 mg, 0.12 mmol) is added and the reaction is deoxygenated and flushed with Argon one more time. The reaction solution is stirred for 7 h at room temperature. Another (90 mg, 0.11 mmol) of the Ruthenium catalyst are added and the reaction is stirred over night. Evaporation of the solvent followed by flash-chromatography, Hexane/Ethylacetate (3:1) afforded the product: $^1$H NMR (CDCl$_3$ 400 Mhz), ppm: 7.81 (d, 2H), 7.37 (m, 5H), 6.93 (d, 2H), 5.60 (m, 2H), 5.10 (m, 3H), 4.18 (dd, 1H), 4.05 (dd, 1H), 3.88 (s, 3H), 3.20 (ddd, 1H), 2.68 (m, 2H), 1.32 (s, 9H).

EXAMPLE 17

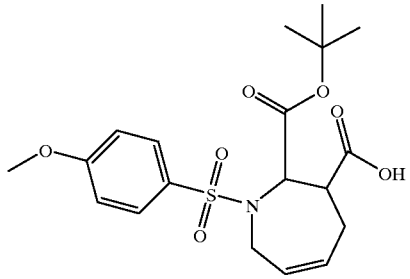

Preparation of 1-(4-Methoxy-benzenesulfonyl)-2,3,4,7-tetrahydro-1H-azepine-2,3-dicarboxylic acid 2-tert-butyl ester 1-(4-Methoxy-benzenesulfonyl)-2,3,4,7-tetrahydro-1H-azepine-2,3-dicarboxylic acid 3-benzyl ester 2-tert-butyl ester (6 g, 12 mmol) is dissolved in a mixture of 120 ml Tetrahydrofuran and 78 ml Water. LiOH.H$_2$O (1 g, 24 mmol) is added. After 45 min., more Water (15 ml) is added and the reaction solution is stirred at room temp. for 24 h. The solvent is evaporated and the remaining solid is resolved in Water/Diethylether. The water layer is acidified to pH 1. The organic phase is separated and the water phase is extracted twice with Ethylacetate. The combined organic fractions are dried with MgSO$_4$ and filtered. The solvent is evaporated to afford the product: Cal. 412.5, found (MH)$^+$ 412.1.

EXAMPLE 18

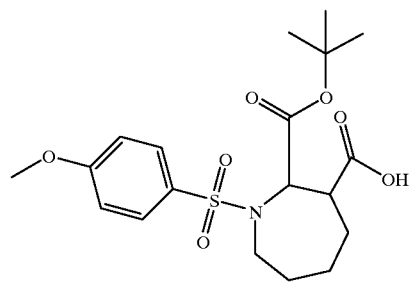

Preparation of 1-(4-Methoxy-benzenesulfonyl)-azepane-2,3-dicarboxylic acid 2-tert-butyl ester 1-(4-Methoxy-benzenesulfonyl)-2,3,4,7-tetrahydro-1H-azepine-2,3-dicarboxylic acid 3-benzyl ester 2-tert-butylester (2.28 g, 4.5 mmol) are dissolved in 40 ml Dioxane/Methanol (3:1). Palladium on charcoal (10%) (170 mg, 0.16 mmol) are added under an Argon flow. The flask is evacuated and flushed three times with Hydrogen. The reaction is stirred for 6 h at room temperature. Filtration through Celite and evaporation of the solvents afforded the product: $^1$H NMR (DMSO, 400 MHz), ppm: 7.81 (d, 2H), 6.95 (d, 2H), 5.40 (d, 1H), 3.68 (s, 3H), 3.65 (m, 1H), 3.25 (m, 1H), 2.92 (m, 1H), 2.15 (m, 1H), 1.95 (m, 1H), 1.78 (m, 2H) 1.25 (s, 9H).

EXAMPLE 19

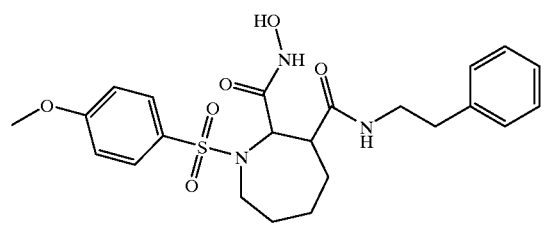

Preparation of 1-(4-Methoxy-benzenesulfonyl)-azepane-2,3-dicarboxylic acid 2-(hydroxamide) 3-(phenethylamide)

Step A. 1-(4-Methoxy-benzenesulfonyl)-3-phenethyl carbamoyl-azepane-2-carboxylic acid tert-butyl ester 1-(4-Methoxy-benzenesulfonyl)-azepane-2,3-dicarboxylic acid 2-tert-butyl ester (171 mg, 0.42 mmol) is dissolved in 5 ml Dimethylformamide (DMF). Phenethylamine (63 μl, 0.5 mmol), 1-Hydroxybenzotriazole (64 mg, 0.42 mmol) and 1-(3-Dimethyl-aminopropyl)-3-ethyl-carbo-diimide hydrochloride (EDC) (121 mg, 0.63 mmol) are added. The reaction mixture is stirred for 4 h at room temperature. The DMF is evaporated and the remaining oil is resolved in Ethylacetate, washed with 2 M Citric acid and then with 0.5 M NaHCO₃-solution. Flash-chromatography with Hexane/Ethylacetate (3:2) afforded the product: Cal. 517.6, found, (MH)⁺ 517.1.

Step B. 1-(4-Methoxy-benzenesulfonyl)-3-phenethyl carbamoyl-azepane-2-carboxylic acid 1-(4-Methoxy-benzenesulfonyl)-3-phenethylcarbamoyl-azepane-2-carboxylic acid tert-butyl ester (112 mg, 0.21 mmol) is dissolved in 4 ml Dichloromethane/Trifluoroacetic Acid (3:1) and stirred for 5 h at room temperature. The solvent/reagent are evaporated and the remaining oil is co-evaporated from Toluene twice. Flash-chromatography, Hexane/Ethylacetate (1:1) afforded the product: Cal. 459.6, found (MH)⁺ 459.

Step C. 1-(4-Methoxy-benzenesulfonyl)-azepane-2,3-dicarboxylic acid 2-(benzyloxyamide) 3-(phenethylamide)

1-(4-Methoxy-benzenesulfonyl)-3-phenethyl-carbamoyl-azepane-2-carboxylic acid (71 mg, 0.15 mmol) is dissolved in 5 ml Dimethylformamide (DMF). Benzylhydroxylamine (30 mg, 0.18 mmol), 1-Hydroxybenzotriazole (24 mg, 0.15 mmol), N-Methylmorpholine (42 μl, 0.37 mmol) and 1-(3-Dimethylaminopropyl)-3-ethylcarbodiimide hydrochloride (EDC) (35.5 mg, 0.18 mmol) are added. The reaction solution is stirred over night at room temperature. The solvent is evaporated and the residual oil is purified by flash-chromatography, Hexane/Ethylacetate (1:1): Exp. 566.7, found (MH)⁺ 566.2.

Step D. 1-(4-Methoxy-benzenesulfonyl)-azepane-2,3-dicarboxylic acid 2-(hydroxamide) 3-(phenethylamide)

1-(4-Methoxy-benzenesulfonyl)-azepane-2,3-dicarboxylic acid 2-(benzyloxyamide) 3-(phenethylamide) (60 mg, 0.11 mmol) is dissolved in 8 ml Dioxane/Methanol (1:1). The flask is flushed with Argon and Pd/C (10%) (40 mg) is added. The reaction suspension is flushed with Hydrogen and stirred for 7 h. The reaction suspension is filtered through Celite and the solvent is evaporated affording the product: Cal. 475.6, found (MH)⁺ 476.2.

EXAMPLE 20

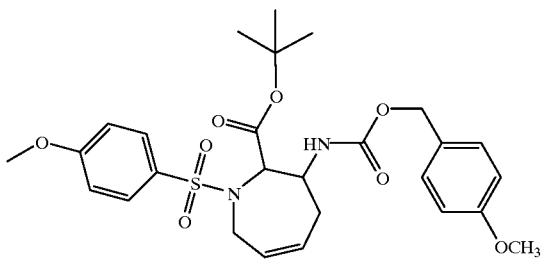

Preparation of 1-(4-Methoxy-benzenesulfonyl)-3-(4-methoxy-benzyloxycarbonyl-amino)-2,3,4,7-tetrahydro-1H-azepine-2-carboxylic acid tert-butyl ester The reaction is performed under an Argon atmosphere and exclusion of light. 1-(4-Methoxy-benzenesulfonyl)-2,3,4,7-tetrahydro-1H-azepine-2,3-dicarboxylic acid 2-tert-butyl ester (550 mg, 1.34 mmol) is dissolved in 7 ml dry Tetrahydrofuran (THF). Tripropyl amine (TPA) (280 μl, 1.47 mmol) is added and the reaction is stirred for 30 minutes at RT. Diphenyl phosphoryl azide (318 μl, 1.47 mmol) is added and the reaction is gradually heated to 40° C. for 3 h. The reaction temperature is then increased to reflux conditions for 6 h. The reaction mixture is allowed to cool to room temperature and 4-Methoxybenzylalcohol (184 μl, 1.47 mmol) is added. The reaction is heated to reflux over night. The solvent is evaporated. Flash-chromatography Hexane/Ethylacetate (2:1) afforded the product: Cal. 383.5 found (MH)⁺ 383.0.

EXAMPLE 21

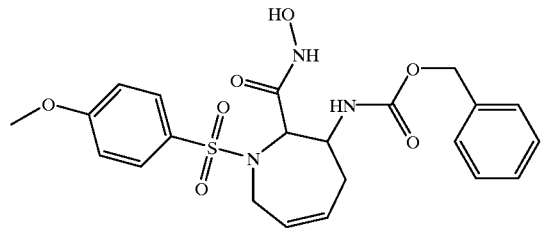

Preparation of (2-Hydroxycarbamoyl-1-(4-methoxybenzene sulfonyl)-2,3,4,7-tetrahydro-1H-azepine-3-yl)-carbamic acid benzyl ester Step A. 3-Benzyloxycarbonylamino-1-(4-methoxy-benzenesulfonyl)-2,3,4,7-tetrahydro-1H-azepine-2-carboxylic acid tert-butyl ester The reaction is performed under an Argon athmosphere. 1-(4-Methoxy-benzenesulfonyl)-2,3,4,7-tetrahydro-1H-azepine-2,3-dicarboxylic acid 2-tert-butyl ester (300 mg, 0.73 mmol) is dissolved in 4 ml Dioxane (dry). Tripropylamine (TPA) (98 μl, 0.73 mmol) is added and the reaction is stirred for 15 minutes at RT. Diphenyl phosphoryl azide (157 μl, 0.73 mmol) is added and the reaction is gradually heated to 60° C. for 3 h. The reaction is then allowed to cool to room temperature. Benzyl alcohol (235 μl, 2.2 mmol) is added and the reaction solution is heated to 60° C. over night. The reaction solution is diluted with Ethylacetate and washed with 2 M Citric Acid and Water. The organic phase is separated, dried with MgSO₄ and filtrated. The solvent is evaporated and the remaining oil is purified by flash-chromatography, Hexane/Ethylacetate (2:1): Cal. 516.6, found (MH)⁺ 517.

Step B. 3-Benzyloxycarbonylamino-1-(4-methoxy-benzene sulfonyl)-2,3,4,7-tetrahydro-1H-azepine-2-carboxylic acid 3-Benzyloxycarbonylamino-1-(4-methoxy-benzenesulfonyl)-2,3,4,7-tetrahydro-1H-azepine-2-carboxylic acid tert-butyl ester (28 mg, 0.054 mmol) is reacted in the same manner as 1-(4-Methoxy-benzenesulfonyl)-3-phenethyl carbamoyl-azepane-2-carboxylic acid tert-butyl ester to afford the free acid: Cal. 460.51, found (MH)⁺ 460.9.

Step C. (2-Hydroxycarbamoyl-1-(4-methoxybenzene sulfonyl)-2,3,4,7-tetrahydro-1H-azepine-3-yl)-carbamic acid benzyl ester 3-Benzyloxycarbonylamino-1-(4-methoxy-benzenesulfonyl)-2,3,4,7-tetrahydro-1H-azepine-2-carboxylic acid (21 mg, 0.043 mmol) is dissolved in dry Dimethylformamide (DMF) and cooled to −20° C. tert-Butyldimethylsilylhydroxyl amine (7 mg, 0.05 mmol), Hunigs Base (9.8 μl, 0.05 mmol) and O-(7-azabenzotriazol-1-yl)-1,1,3,3-tetramethyl uronium hexafluorophosphate (HATU) (18 mg, 0.05 mmol) are added. The reaction solution is stirred for 1 h and then allowed to warm to room temp. The solvent is evaporated. The residue is purified by flash-chromatography, Dichloromethane/Methanol (9:1), to afford the desired hydroxamide: Cal. 476.5, Found (MH)⁺ 476.

EXAMPLE 22

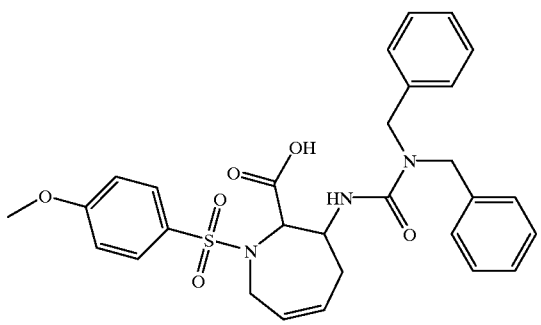

Preparation of 3-(3,3-Dibenzylureido)-1-(4-methoxy-benzenesulfonyl)-2,3 4,7-terahydro-1H-azepine-2-carboxylic acid Step A. 3-(3,3-Dibenzylureido)-1-(4-methoxy-benzenesulfonyl)-2,3,4,7-tetrahydro-1H-azepine-2-carboxylic acid tert-butyl ester The reaction is performed under an Argon blanket. 1-(4-Methoxy-benzenesulfonyl)-2,3,4,7-tetrahydro-1H-azepine-2,3-dicarboxylic acid 2-tert-butyl ester (204 mg, 0.5 mmol) is dissolved in 10 ml dry Dioxane. Tripropylamine (94 µl, 0.5 mmol) is added and then Diphenyl phosphoryl azide (DPPA). The reaction is heated to 75° C. for 5 h. After cooling to room temperature, Dibenzylamine (190.6 µl, 1 mmol) is added via syringe. The reaction is heated to 70° C. and stirred over night. Evaporation of the solvents and flash-chromatography, Hexane/Ethyl acetate (1:1) afforded the product: Cal. 606.8 found (MH)+ 606.2.

Step B. 3-(3,3-Dibenzylureido)-1-(4-methoxy-benzene sulfonyl)-2,3,4,7-terahydro-1H-azepine-2-carboxylic acid 3-(3,3-Dibenzylureido)-1-(4-methoxy-benzenesulfonyl)-2,3,4,7-tetrahydro-1H-azepine-2-carboxylic acid tert-butyl ester (200 mg, 0.33 mMol) is reacted in the same manner as 1-(4-Methoxybenzenesulfonyl)-3-phenethyl carbamoyl-azepane-2-carboxylic acid tert-butyl ester and purified by flash-chromatography, Dichloromethane/Methanol (9:1) to afford the free acid: Cal. 550.6 found (MH)+=550.

EXAMPLE 23

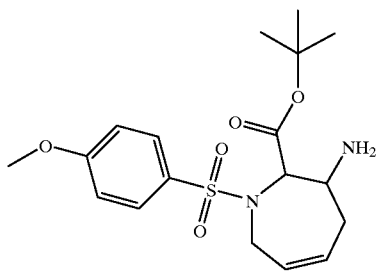

Preparation of 3-Amino-1-(4-methoxy-benzenesulfonyl)-2,3,4,7-tetrahydro-1H-azepine-2-carboxylic acid tert-butyl ester 1-(4-Methoxy-benzenesulfonyl)-3-(4-methoxybenzyloxy carbonyl-amino)-2,3,4,7-tetrahydro-1H-azepine-2-carboxylic acid tert-butyl ester (370 mg, 0.71 mMol) is dissolved in Dichloromethane (15 ml) containing 3% Trifluoroacetic Acid. The reaction is stirred for 1 h at room temperature. The solvents are evaporated and the remaining oil is co-evaporated twice with Toluene. Flash-chromatography Dichloromethane/Methanol (7:1) to afford the free amine: Cal. 546.6 found (MH)+=547.

EXAMPLE 24

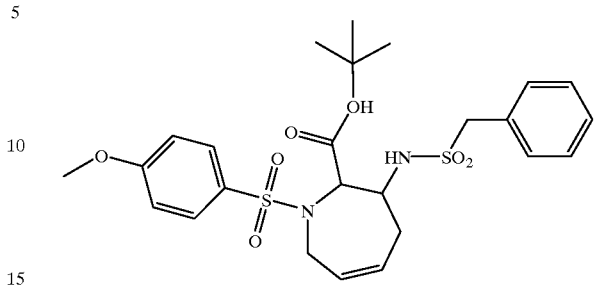

Preparation of 1-(4-Methoxy-benzenesulfonyl)-3-(phenylmethanesulfonylamino)-2,3 4,7-tetrahydro-1H-azepine-2-carboxylic acid Step A. 1-(4-Methoxy-benzenesulfonyl)-3-(phenylmethane sulfonylamino)-2,3,4,7-tetrahydro-1H-azepine-2-carboxylic acid tert-butyl ester 3-Amino-1-1(4-methoxy-benzenesulfonyl)-2,3,4,7-tetrahydro-1H-azepine-2-carboxylic acid tert-butyl ester (38 mg, 0.1 mmol) is dissolved in 3 ml dry Dichloromethane. Hunigs Base (42 µl, 0.24 mmol) is added and then alpha-Toluenesulfonyl chloride (28.4 mg, 0.15 mmol) is added. The reaction mixture is stirred at room temperature for 4 h. The solvent is evaporated and the remaining oil is purified by Flash-chromatography Hexane/Ethylacetate (2:1): $^1$H NMR (CDCl$_3$ 400 MHz), ppm: 7.75 (d, 2H), 7.50 (m, 2H),7.4 (m, 3H) 6.99 (d, 2H), 5.70 (m, 2H), 4.85 (d, 1H), 4.56 (d, 1H), 4.35 (dd, 2H), 4.22 (dd, 1H), 4.02 (m, 1H), 3.90 (m, 3H), 3.83 (m, 1H),2.50 (m, 1H), 2.30 (m, 1H), 1.30 (s, 9H).

Step B. 1-(4-Methoxy-benzenesulfonyl)-3-(phenylmethane sulfonylamino)-2,3,4,7-tetrahydro-1H-azepine-2-carboxylic acid 1-(4-Methoxy-benzenesulfonyl)-3-(phenylmethanesulfonyl amino)-2,3,4,7-tetrahydro-1H-azepine-2-carboxylic acid tert-butyl ester (29 mg, 0.054 mmol) is reacted in the same manner as 1-(4-Methoxybenzenesulfonyl)-3-phenethyl carbamoyl-azepane-2-carboxylic acid tert-butyl ester: Cal. 479.5 found (M–H)+ 778.6. Cal. 498.6, found (MNH$_4$)+ 498.1; $^1$H NMR (DMSO, 400 MHz), ppm: 7.85 (d, 2H), 7.38 (m, 5H) 7.01 (d, 2H), 5.5 (m, 2H) 4.45 (d, 2H), 4.30 (d, 2H), 4.15 (m, 2H), 4.00 (m, 1H), 3.90 (dd, 1H), 3.83 (s, 3H), 2.18 (m, 2H).

EXAMPLE 25

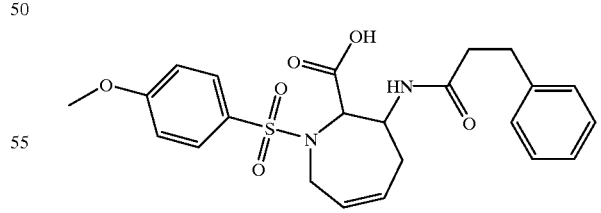

Preparation of 1-(4-Methoxy-benzenesulfonyl)-3-(3-phenylpropionylamino)-2,3,4,7-tetrahydro-1H-azepine-2-carboxylic acid Step A. 1-(4-Methoxy-benzenesulfonyl)-3-(3-phenyl-propionylamino)-2,3,4,7-tetrahydro-1H-azepine-2-carboxylic acid tert-butyl ester 3-Amino-1-(4-methoxy-benzenesulfonyl)-2,3,4,7-tetrahydro-1H-azepine-2-carboxylic acid tert-butyl ester (31 mg, 0.08 mmol) is dissolved in 4 ml Dichloromethane and cooled to 0° C. Hunigs Base (34 μl, 0.2 mmol) is added followed by Hydrocinnamyl chloride (18 μl, 0.12 mmol). The reaction is stirred 1 h at 0° C. and is then allowed to warm to room temperature. The solvents are evaporated and the remaining oil is purified by flash-chromatography, Dichloro-methane/Methanol (9:1) affording the product: Cal. 513.6 found (MH)⁺=514.9.

Step B. 1-(4-Methoxy-benzenesulfonyl)-3-(3-phenyl propionylamino)-2,3,4,7-tetrahydro-1H-azepine-2-carboxylic acid 1-(4-Methoxy-benzenesulfonyl)-3-(3-phenylpropionyl amino)-2,3,4,7-tetrahydro-1H-azepine-2-carboxylic acid tert-butyl ester (22 mg, 0.04 mmol) is reacted in the same manner as 1-(4-Methoxybenzenesulfonyl)-3-phenethyl carbamoyl-azepane-2-carboxylic acid tert-butyl ester and purified by flash-chromatography, Dichloromethane/Methanol (9:1) to afford the acid: Cal. 457.5 found (M–H)⁺ 456.6; ¹H NMR (DMSO, 400 MHz), ppm: 7.78 (d, 2H), 7.28 (m, 2H), 7.20 (m, 3H), 7.01 (d, 2H), 5.6 (m, 1H), 5.5 (m, 1H), 4.3 (m, 3H), 4.0 (m, 1H), 3.82 (s, 3H), 2.8 (t, 2H), 2.35 (m, 2H), 2.05 (m, 2H).

EXAMPLE 26

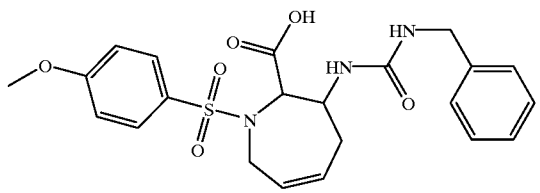

Preparation of 3-(3-Benzylureido)-1-(4-methoxy-benzenesulfonyl)-2,3,4,7-tetrahydro-1H-azepine-2-carboxylic acid Step A. 3-(3-Benzylureido)-1-(4-methoxy-benzenesulfonyl)-2,3,4,7-tetrahydro-1H-azepine-2-carboxylic acid tert-butyl ester 3-Amino-1-(4-methoxy-benzenesulfonyl)-2,3,4,7-tetrahydro-1H-azepine-2-carboxylic acid tert-butyl ester (33 mg, 0.09 mmol) is solved in 3 ml dry Dioxane. Benzylisocyanate (10.6 μl, 0.086 mmol) is added and the reaction is stirred at room temperature for 1 h. Evaporation of the solvent and flash-chromatography, Dichloromethane/Methanol (7:1) afforded the product: Cal. 515.6 found (MH)⁺ 515.9.

Step B. 3-(3-Benzylureido)-1-(4-methoxy-benzenesulfonyl)-2,3,4 7-tetrahydro-1H-azepine-2-carboxylic acid 3-(3-Benzylureido)-1-(4-methoxy-benzenesulfonyl)-2,3,4,7-tetrahydro-1H-azepine-2-carboxylic acid tert-butyl ester (25 mg, 0.05 mmol) is reacted in the same manner as 1-(4-Methoxybenzenesulfonyl)-3-phenethyl carbamoyl-azepane-2-carboxylic acid tert-butyl ester and purified by flash-chromatography, Dichloromethane/Methanol (9:1): Cal. 458.5 found (M–H)⁺ 458.2; ¹H NMR (DMSO, 400 MHz), ppm: 7.79 (d, 2H), 7.30 (m, 2H),7.20 (m, 3H) 7.02 (d, 2H), 5.60 (m, 1H), 5.50 (m, 1H) 4.3 (m, 3H), 4.00 (m, 1H), 3.93 (m, 3H), 2.81 (t, 2H),2.35 (m, 2H), 2.05 (m, 2H).

EXAMPLE 27

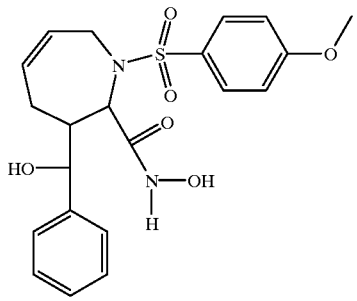

Preparation of 3-(Hydroxy-phenyl-methyl)-1-(4-methoxy-benzenesulfonyl)-2,3,4,7-tetrahydro-1H-azepine-2-hydroxamic acid Step A. 1-(4-Methoxy-benzenesulfonyl)-2,3,4,7-tetrahydro-1H-azepine-2,3-dicarboxylic acid 3-benzyl ester 1-(4-Methoxy-benzenesulfonyl)-2,3,4,7-tetrahydro-1H-azepine-2,3-dicarboxylic acid 3-benzyl ester 2-tert-butyl ester (1.6 g, 3.2 mmol) was dissolved in anhydrous methylene chloride (16 mL) and treated with trifluoroacetic acid (4 mL). The solution was stirred at ambient temperature for 3 hrs and then the solvents were removed in vacuo. The residue was coevaporated with toluene two times and then purified by column chromatography (silica) to yield 1-(4-methoxy-benzenesulfonyl)-2,3,4,7-tetrahydro-1H-azepine-2,3-dicarboxylic acid 3-benzyl ester; MS: (M+H)⁺ 446.

Step B. 2-Benzhydryloxycarbamoyl-1-(4-methoxy-benzenesulfonyl)-2,3,4,7-tetrahydro-1H-azepine-3-carboxylic acid benzyl ester 1-(4-Methoxy-benzenesulfonyl)-2,3,4,7-tetrahydro-1H-azepine-2,3-dicarboxylic acid 3-benzyl ester (417 mg, 0.94 mmoL) was dissolved in anhydrous DMF (5 mL) and cooled to 0° C. This solution was then treated with diphenylhydroxyl amine (265 mg, 1.12 mmoL) and HATU (391 mg, 1.0 mmoL). The reaction mixture was stirred 1 hr at 0° C. and then overnight at 25° C. This mixture was then concentrated in vacuo and purified by column chromatography (silica, 40% diethyl ether in hexanes) to yield 2-benzhydryloxycarbamoyl-1-(4-methoxy-benzenesulfonyl)-2,3,4,7-tetrahydro-1H-azepine-3-carboxylic acid benzyl ester; MS: (M+H)⁺ 627.

Step C. 7-Benzhydryloxy-1-(4-methoxybenzenesulfonyl)-2,5,5a,8a-tetrahydro-1H-pyrrolo[3,4-b]azepine-6,8-dione The 2-benzhydryloxycarbamoyl-1-(4-methoxy-benzenesulfonyl)-2,3,4,7-tetrahydro-1H-azepine-3-carboxylic acid benzyl ester (430 mg, 0.69 mmoL) was dissolved in a THF:H₂O (1:1, 10 mL) mixture and was then treated with LiOH (35 mg, 0.82 mmoL). This solution was stirred overnight at ambient temperature. The THF was removed in vacuo and the resulting mixture was acidified with 2 M aqueous citric acid. The product was extracted into diethyl ether, dried (Na₂SO₄) and concentrated. The residue was purified by flash chromatography (silica, 10% methanol in chloroform) to give 7-benzhydryloxy-1-(4-methoxybenzenesulfonyl)-2,5,5a,8a-tetrahydro-1H-pyrrolo[3,4-b]azepine-6,8-dione; MS: (M+H)⁺ 519.

Step D. 3-Benzoyl-1-(4-methoxy-benzenesulfonyl)-2,3,4,7-tetrahydro-1H-azepine-2-carboxylic acid benzhydryloxyamide 7-Benzhydryloxy-1-(4-methoxybenzenesulfonyl)-2,5,5a,8a-tetrahydro-1H-pyrrolo[3,4-b]azepine-6,8-dione (100 mg, 0.19 mmol) was dissolved in THF (2 mL) and cooled to −78°

C. This solution was treated dropwise with a 3 M solution of phenyl magnesium bromide in diethyl ether and then warmed to ambient temperature. The reaction mixture was stirred another 2.5 hrs at room temperature, cooled to 0° C., and quenched with saturated aqueous NH$_4$Cl (2 mL). This mixture was then diluted with H$_2$O and diethyl ether and the layers were separated. The organic phase was washed with brine, dried (Na$_2$SO$_4$) and concentrated. The residue was purified by flash chromatography (silica, 5 to 10% ethyl acetate in toluene) to give 3-benzoyl-1-(4-methoxy-benzenesulfonyl)-2,3,4,7-tetrahydro-1H-azepine-2-carboxylic acid benzhydryloxy-amide; MS: (M+H)$^+$ 596.9, (M+NH4)$^+$ 614.2.

Step E. 3-(Hydroxy-phenyl-methyl)-1-(4-methoxy-benzenesulfonyl)-2,3,4,7-tetrahydro-1H-azepine-2-carboxylic acid benzhydryloxy-amide 3-Benzoyl-1-(4-methoxy-benzenesulfonyl)-2,3,4,7-tetrahydro-1H-azepine-2-carboxylic acid benzhydryloxy-amide (32 mg, 0.054 mmoL) was dissolved in a methanol:dichloromethane (3:1, 1.3 mL) mixture and cooled to 0° C. This solution was treated with sodium borohydride and stirred 5 hrs at 0 to 25° C. The solvents were removed in vacuo and the residue was reconstituted in dichloromethane. This solution was washed with 1 M aqueous HCl, and H$_2$O, dried (Na$_2$SO$_4$) and concentrated. The residue was purified by flash chromatography (silica, 1.25% methanol in dichloromethane) to give 3-(hydroxy-phenyl-methyl)-1-(4-methoxy-benzenesulfonyl)-2,3,4,7-tetrahydro-1H-azepine-2-carboxylic acid benzhydryloxy-amide; MS: (M+H)$^+$ 598.8, (M+NH4)$^+$ 615.7.

Step F. 3-(Hydroxy-phenyl-methyl)-1-(4-methoxy-benzenesulfonyl)-2,3,4,7-tetrahydro-1H-azepine-2-carboxylic acid hydroxyamide A solution of 3-(hydroxy-phenyl-methyl)-1-(4-methoxy-benzenesulfonyl)-2,3,4,7-tetrahydro-1H-azepine-2-carboxylic acid benzhydryloxy-amide (5 mg, 0.008 mmoL) in dichloromethane (1 mL) was cooled to 0° C. This solution was treated with trifluoroacetic acid (0.1 mL) followed by a 0.31 M solution of triethylsilane in dichloromethane (0.026 mL). The reaction mixture was warmed from 0 to 25° C. over 35 minutes and then the solvents were removed in vacuo and the residue was coevaporated with toluene. The residue was purified by flash chromatography (silica, 5 to 10% methanol in dichloromethane) to give 3-(hydroxy-phenyl-methyl)-1(4-methoxy-benzenesulfonyl)-2,3,4,7-tetrahydro-1H-azepine-2-carboxylic acid hydroxyamide as a white solid; MS: (M–H)$^-$ 430.9.

EXAMPLE 28

Using the procedures of Examples 1–27 above the following compounds were also prepared:

1-(4-Methoxy-benzenesulfonyl)-azepane-2,3-dicarboxylic acid 2-(hydroxamide) 3-(phenmethylamide): Cal. 460.54 found (MH)$^+$=461;

1-(4-Methoxy-benzenesulfonyl)-azepane-2,3-dicarboxylic acid 2-(hydroxamide) 3-(phenpropylamide): Cal. 488.59 found (MH)$^+$=489;

1-(4-Methoxy-benzenesulfonyl)-azepane-2,3-dicarboxylic acid 2-(hydroxamide) 3-(4-phenoxy-2-ethylamide): Cal. 491.57 found (MH)$^+$=492;

1-(4-Methoxy-benzenesulfonyl)-azepane-2,3-dicarboxylic acid 2-(hydroxamide) 3-(thiopiperizineamide): Cal. 457.6 found (MH)$^+$=458;

1-(4-Methoxy-benzenesulfonyl)-azepane-2,3-dicarboxylic acid 2-(hydroxamide) 3-(phenylmethylsulfanylethylamide): Cal. 520.66 found (MH)$^+$=521;

1-(4-Methoxy-benzenesulfonyl)-azepane-2,3-dicarboxylic acid 2-(hydroxamide) 3-(4-Phenoxylphenethylamide): Cal. 566.6 found (MH)$^+$=567;

Cis-3-(4-Phenylbenzyl)-1-(4-methoxybenzenesulfonyl)-azepane-2-hydroxamic acid: Cal. 494.6 found (MH)$^+$=495;

Trans-3-(4-Phenylbenzyl)-1-(4-methoxybenzenesulfonyl)-azepane-2-hydroxamic acid: Cal. 494.6 found (MH)$^+$=495;

Trans-3-Methyl-1-(4-methoxybenzenesulfonyl)-azepane-2-hydroxamic acid: Cal. 342.4 found (MH)$^+$=343.

EXAMPLE 29

Using the procedures of Examples 1–27 above the following compounds can be prepared:

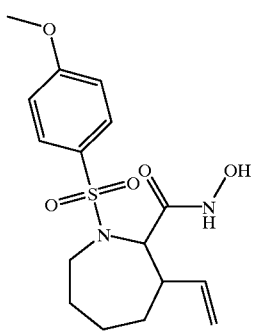

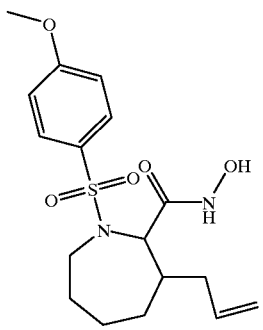

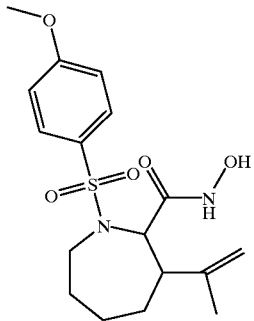

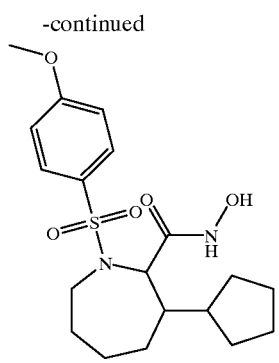
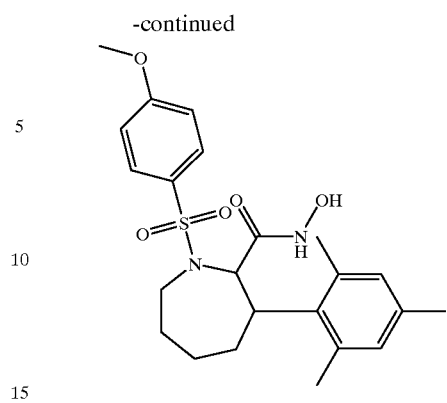
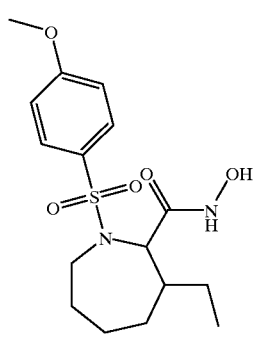
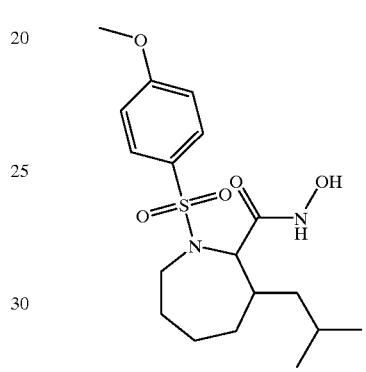
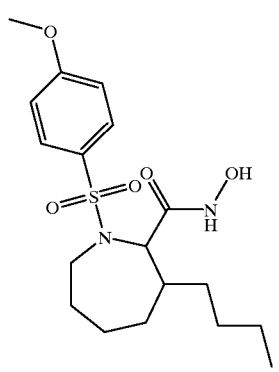
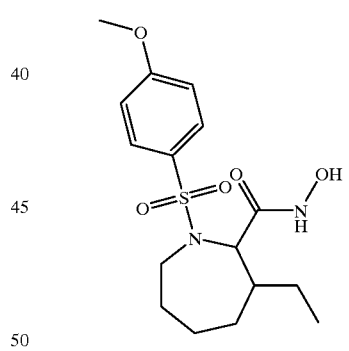
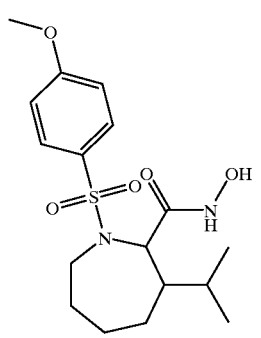
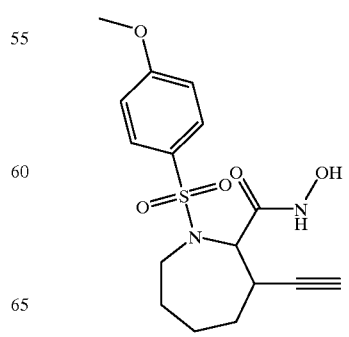

-continued

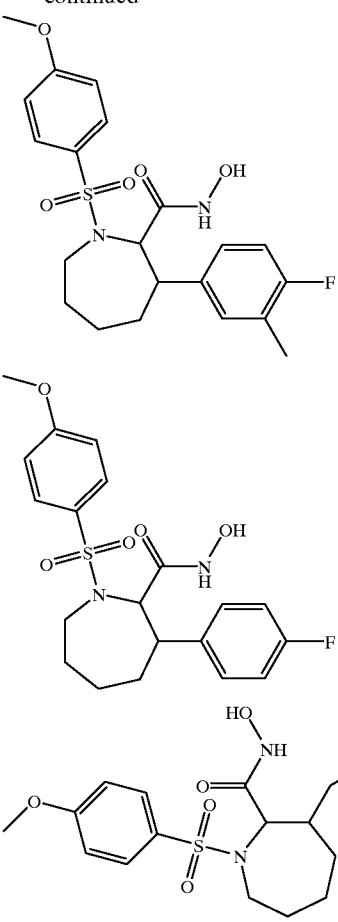

EXAMPLE 30

Using the procedures of the above general descriptions and the above examples, the compounds of Tables I–VI can be prepared.

TABLE I

| $R^1$ | $R^9$ | $R^{11}$ |
|---|---|---|
| 4-MeO—Ph— | BzMeN—C(O)— | HO— |
| 4-MeO—Ph— | phenyl | HO— |
| 4-MeO—Ph— | EtO—C(O)— | HO— |
| 4-MeO—Ph— | HO—C(O)— | HO— |
| 4-MeO—Ph— | 2-pyridyl | HO— |
| 4-CF₃O—Ph— | 3-pyridyl | H— |
| 4-MeO—Ph— | 4-morpholino-C(O)— | HO— |
| 4-MeO—Ph— | BzO—C(O)— | HO— |
| 4-Me—Ph— | Ph—NH—C(O)— | HO— |
| 3-MeO—Ph— | Bz—NH—C(O)— | HO— |

TABLE I-continued

| $R^1$ | $R^9$ | $R^{11}$ |
|---|---|---|
| 4-MeO—Ph— | BzEtN—C(O)— | HO— |
| 4-MeO—Ph— | (4,4-dimethyl pentyl)NHC(O)— | HO— |
| 4-Cl—Ph— | PhMeN—C(O)— | HO— |
| 2-thienyl | PhMeN—C(O)— | HO— |
| 4-MeO—Ph— | H— | BzNH—C(O)—O— |
| 3,4-dimethoxy-phenyl | H— | PhNH—C(O)—O— |
| 4-MeO—Ph— | H— | (4-PhO—Ph)NH—C(O)—O— |
| 4-MeO—Ph— | H— | i-propylNH—C(O)—O— |
| 4-MeO—Ph— | H— | MeNH—C(O)—O— |
| 4-MeO—Ph— | H— | (1-Ph-ethyl)NH—C(O)—O— |
| 4-MeO—Ph— | H— | (4-MeO—Ph)NH—C(O)—O— |
| 5-benzo-thiazolyl | H— | (2-Ph-ethyl)NH—C(O)—O— |
| phenyl | H— | vinyl- |
| 4-CN—Ph— | H— | HO— |
| 4-(Me—C(O)—NH)—Ph— | H— | HO— |
| 4-i-propyl-Ph— | H— | HO— |
| 4-Et—Ph— | H— | HO— |
| 4-t-butyl-Ph— | H— | H— |
| n-dodecyl | H— | HO— |
| n-octyl | H— | H— |
| 4-MeO—Ph— | Ph—SO₂—NH— | H— |
| 4-MeO—Ph— | MeC(O)—NH— | HO— |
| 4-MeO—Ph— | MeO—C(O)—NH— | (4-F—Ph)NH—C(O)—O— |
| 4-MeO—Ph— | methyl | H— |
| 4-MeO—Ph— | Ph—C(O)—NH— | HO— |
| 4-MeO—Ph— | H— | benzyl |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeO—Ph— | H— | H— |
| 4-MeO—Ph— | H— | H— |
| 4-MeO—Ph— | H— | H— |
| 4-MeO—Ph— | EtO—C(O)— | H— |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeS—Ph— | BzMeN—C(O)— | HO— |
| 4-Cl—Ph— | phenyl | Ph—SO₂—NH— |
| 4-CF₃O—Ph— | MeO—C(O)— | thienyl-S— |
| 5-benzo-dioxolyl | HO—C(O)— | HO— |
| 4-Me—Ph— | 2-pyridyl | HO— |
| 4-MeO—Ph— | 3-pyridyl | MeS— |
| 4-MeO—Ph— | 4-morpholino-C(O)— | HO— |
| n-dodecyl | BzO—C(O)— | HO— |
| 4-MeO—Ph— | Ph—NH—C(O)— | thienyl-NH—C(O)—O— |
| furyl | Bz—NH—C(O)— | HO— |
| 4-MeO—Ph— | 3-Ph-propyl-NH—C(O)— | 2-pyridyl-NH—C(O)—O— |
| 4-PhO—Ph— | (2-Ph-ethyl)(Me)N—C(O)— | HO— |
| 4-pyridyl | BzEtN—C(O)— | propargyl |

TABLE I-continued

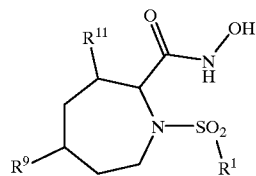

| R¹ | R⁹ | R¹¹ |
|---|---|---|
| 4-MeO—Ph— | (4,4-dimethyl pentyl)NHC(O)— | thienyl-O— |
| 4-MeO—Ph— | 3-pyridyl | HO— |
| 5-benzofuranyl | 4-morpholino-C(O)— | HO— |
| 4-MeO—Ph— | BzO—C(O)— | HO— |
| 4-MeO—Ph— | Bz—NH—C(O)— | HO— |
| 5-benzothiazolyl | Ph—NH—C(O)— | (1-Ph-ethyl)NH—C(O)—O— |
| 4-PhO—Ph— | 3-Ph-propyl-NH—C(O)— | HO— |
| 4-MeO—Ph— | (2-Ph-ethyl)(Me)N—C(O)— | vinyl |
| 4-MeO—Ph— | (4,4-dimethyl pentyl)NHC(O)— | PhNH—C(O)—O— |
| n-dodecyl | BzEtN—C(O)— | HO— |
| 4-morpholino | phenyl | PhNH—C(O)—O— |
| 2-naphthyl | 3-pyridyl | MeNH—C(O)—O— |
| 3,4-dimethoxyphenyl | 4-morpholino-C(O)— | i-propylNH—C(O)—O— |
| 4-piperidinyl-butyl | BzO—C(O)— | (4-PhO—Ph)NH—C(O)—O— |
| 6-benzodioxanyl | Ph—NH—C(O)— | thienyl-NH—C(O)—O— |
| 4-hydroxycyclohexyl | 2-pyridyl-NH—C(O)— | (4-MeO—Ph)NH—C(O)—O— |
| 4-MeO—Ph— | BzMeN—C(O)— | 3-(3-furyl)-butyl |
| 4-MeO—Ph— | 4-acetamido-phenyl | 4-methyl-pentyl |
| 4-MeO—Ph— | 3-pyridyl | 2-MeS-ethyl |
| 4-MeO—Ph— | H— | PhNH—C(O)-ethyl |
| 4-MeO—Ph— | 4-chlorobenzyl | 4-pyrid-3-yl-butyl |
| 4-MeO—Ph— | 4-pyridyl | 3-hydroxy-butyl |
| 4-MeO—Ph— | H— | PhNH—C(O)-methyl |
| 4-MeO—Ph— | HO—C(O)— | 2-(pyrid-3-yl-C(O)—NH)-ethyl |
| 4-MeO—Ph— | phenyl | 2-(2-thienyl-thio)ethyl |
| 4-MeO—Ph— | 3-pyridyl | 3-MeS-propyl |
| 4-MeO—Ph— | 4-morpholino-C(O)— | PhNH—C(O)-methyl |
| 4-MeO—Ph— | EtO—C(O)— | 2-phenoxyethyl |
| 4-MeO—Ph— | Ph—NH—C(O)— | 3-pyrid-3-yl-propyl |
| 4-MeO—Ph— | 2-pyridyl-NH—C(O)— | iso-butyl |
| 4-ClPh—Ph— | H— | phenethyl-C(O)—NH |
| 4-ClPh—Ph— | H— | benzyl-SO₂—NH |
| 4-MeO—Ph— | H— | benzyl-NH—C(O)—NH |
| 4-MeO—Ph— | H— | phenyl-NH—SO₂—NH— |
| 4-ClPh—Ph— | H— | benzyl-NH—SO₂—NH— |
| 4-MeO—Ph— | H— | benzyloxy-C(O)—NH— |
| 4-MeO—Ph— | H— | benzyl-NH—SO₂—NH— |

TABLE II

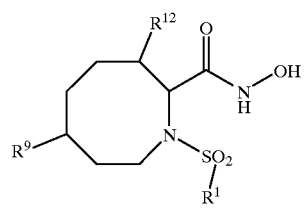

| R¹ | R⁹ | R¹² |
|---|---|---|
| 4-MeO—Ph— | BzMeN—C(O)— | HO— |
| 4-MeO—Ph— | phenyl | HO— |
| 4-MeO—Ph— | EtO—C(O)— | HO— |
| 4-MeO—Ph— | HO—C(O)— | HO— |
| 4-MeO—Ph— | 2-pyridyl | HO— |
| 4-CF₃O—Ph— | 3-pyridyl | H— |
| 4-MeO—Ph— | 4-morpholino-C(O)— | HO— |
| 4-MeO—Ph— | BzO—C(O)— | HO— |
| 4-Me—Ph— | Ph—NH—C(O)— | HO— |
| 3-MeO—Ph— | Bz—NH—C(O)— | HO— |
| 4-MeO—Ph— | BzEtN—C(O)— | HO— |
| 4-MeO—Ph— | (4,4-dimethyl pentyl)NHC(O)— | HO— |
| 4-Cl—Ph— | PhMeN—C(O)— | HO— |
| 2-thienyl | PhMeN—C(O)— | HO— |
| 4-MeO—Ph— | H— | BzNH—C(O)—O— |
| 3,4-dimethoxyphenyl | H— | PhNH—C(O)—O— |
| 4-MeO—Ph— | H— | MeNH—C(O)—O— |
| 4-MeO—Ph— | H— | i-propylNH—C(O)—O— |
| 4-MeO—Ph— | H— | (4-PhO—Ph)NH—C(O)—O— |
| 4-MeO—Ph— | H— | (1-Ph-ethyl)NH—C(O)—O— |
| 4-MeO—Ph— | H— | (4-MeO—Ph)NH—C(O)—O— |
| 5-benzothiazolyl | H— | (2-Ph-ethyl)NH—C(O)—O— |
| phenyl | H— | vinyl |
| 4-CN—Ph— | H— | HO— |
| 4-(Me—C(O)—NH)—Ph— | H— | HO— |
| 4-i-propyl-Ph— | H— | HO— |
| 4-Et—Ph— | H— | HO— |
| 4-t-butyl-Ph— | H— | H— |
| n-dodecyl | H— | H— |
| n-octyl | H— | H— |
| 4-MeO—Ph— | Ph—SO₂—NH— | H— |
| 4-MeO—Ph— | MeC(O)—NH— | HO— |
| 4-MeO—Ph— | MeO—C(O)—NH— | (4-F—Ph)NH—C(O)—O— |
| 4-MeO—Ph— | methyl | H— |
| 4-MeO—Ph— | Ph—C(O)—NH— | HO— |
| 4-MeO—Ph— | H— | benzyl |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeO—Ph— | H— | H— |
| 4-MeO—Ph— | H— | H— |
| 4-MeO—Ph— | EtO—C(O)— | H— |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeS—Ph— | BzMeN—C(O)— | HO— |
| 4-Cl—Ph— | phenyl | Ph—SO₂—NH— |
| 4-CF₃O—Ph— | MeO—C(O)— | thienyl-S— |
| 5-benzodioxolyl | HO—C(O)— | HO— |
| 4-Me—Ph— | 2-pyridyl | HO— |

TABLE II-continued

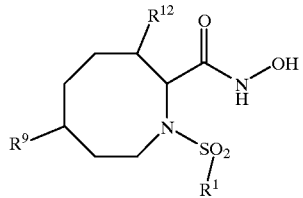

| R$^1$ | R$^9$ | R$^{12}$ |
|---|---|---|
| 4-MeO—Ph— | 3-pyridyl | MeS— |
| 4-MeO—Ph— | 4-morpholino-C(O)— | HO— |
| n-dodecyl | BzO—C(O)— | HO— |
| 4-MeO—Ph— | Ph—NH—C(O)— | thienyl-NH—C(O)—O— |
| furyl | Bz—NH—C(O)— | HO— |
| 4-MeO—Ph— | 3-Ph-propyl-NH—C(O)— | 2-pyridyl-NH—C(O)—O— |
| 4-PhO—Ph— | (2-Ph-ethyl)(Me)N—C(O)— | HO— |
| 4-pyridyl | BzEtN—C(O)— | propargyl |
| 4-MeO—Ph— | (4,4-dimethyl pentyl)NHC(O)— | thienyl-O— |
| 4-MeO—Ph— | 3-pyridyl | HO— |
| 5-benzofuranyl | 4-morpholino-C(O)— | HO— |
| 4-MeO—Ph— | BzO—C(O)— | HO— |
| 5-benzothiazolyl | Ph—NH—C(O)— | (1-Ph-ethyl)NH—C(O)—O— |
| 4-MeO—Ph— | Bz—NH—C(O)— | HO— |
| 4-PhO—Ph— | 3-Ph-propyl-NH—C(O)— | HO— |
| 4-MeO—Ph— | (2-Ph-ethyl)(Me)N—C(O)— | vinyl |
| n-dodecyl | BzEtN—C(O)— | HO— |
| 4-MeO—Ph— | (4,4-dimethyl pentyl)NHC(O)— | PhNH—C(O)—O— |
| 4-morpholino | phenyl | PhNH—C(O)—O— |
| 2-naphthyl | 3-pyridyl | MeNH—C(O)—O— |
| 3,4-dimethoxy-phenyl | 4-morpholino-C(O)— | i-propylNH—C(O)—O— |
| 4-piperidinyl-butyl | BzO—C(O)— | (4-PhO—Ph)NH—C(O)—O— |
| 6-benzodioxanyl | Ph—NH—C(O)— | thienyl-NH—C(O)—O— |
| 4-hydroxycyclohexyl | 2-pyridyl-NH—C(O)— | (4-MeO—Ph)NH—C(O)—O— |
| 4-MeO—Ph— | BzMeN—C(O)— | 3-(3-furyl)-butyl |
| 4-MeO—Ph— | 4-acetamidophenyl | 4-methylpentyl |
| 4-MeO—Ph— | 3-pyridyl | 2-MeS-ethyl |
| 4-MeO—Ph— | H— | PhNH—C(O)-ethyl |
| 4-MeO—Ph— | 4-chlorobenzyl | 4-pyrid-3-yl-butyl |
| 4-MeO—Ph— | 4-pyridyl | 3-hydroxybutyl |
| 4-MeO—Ph— | H— | PhNH—C(O)-methyl |
| 4-MeO—Ph— | HO—C(O)— | 2-(pyrid-3-yl-C(O)—NH)-ethyl |
| 4-MeO—Ph— | phenyl | 2-(2-thienyl-thio)ethyl |
| 4-MeO—Ph— | 4-morpholino-C(O)— | PhNH—C(O)-methyl |
| 4-MeO—Ph— | 3-pyridyl | 3-MeS-propyl |
| 4-MeO—Ph— | EtO—C(O)— | 2-phenoxyethyl |
| 4-MeO—Ph— | Ph—NH—C(O)— | 3-pyrid-3-yl-propyl |
| 4-MeO—Ph— | 2-pyridyl-NH—C(O)— | iso-butyl |

TABLE III

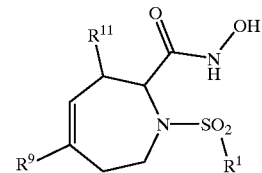

| R$^1$ | R$^9$ | R$^{11}$ |
|---|---|---|
| 4-MeO—Ph— | BzMeN—C(O)— | HO— |
| 4-MeO—Ph— | phenyl | HO— |
| 4-MeO—Ph— | EtO—C(O)— | HO— |
| 4-MeO—Ph— | HO—C(O)— | HO— |
| 4-MeO—Ph— | 2-pyridyl | HO— |
| 4-CF$_3$O—Ph— | 3-pyridyl | H— |
| 4-MeO—Ph— | 4-morpholino-C(O)— | HO— |
| 4-MeO—Ph— | BzO—C(O)— | HO— |
| 4-Me—Ph— | Ph—NH—C(O)— | HO— |
| 3-MeO—Ph— | Bz—NH—C(O)— | HO— |
| 4-MeO—Ph— | BzEtN—C(O)— | HO— |
| 4-MeO—Ph— | (4,4-dimethyl pentyl)NHC(O)— | HO— |
| 4-Cl—Ph— | PhMeN—C(O)— | HO— |
| 2-thienyl | PhMeN—C(O)— | HO— |
| 4-MeO—Ph— | H— | BzNH—C(O)—O— |
| 3,4-dimethoxy-phenyl | H— | PhNH—C(O)—O— |
| 4-MeO—Ph— | H— | MeNH—C(O)—O— |
| 4-MeO—Ph— | H— | 1-propylNH—C(O)—O— |
| 4-MeO—Ph— | H— | (4-PhO—Ph)NH—C(O)—O— |
| 4-MeO—Ph— | H— | (1-Ph-ethyl)NH—C(O)—O— |
| 4-MeO—Ph— | H— | (4—MeO—Ph)NH—C(O)—O— |
| 5-benzothiazolyl | H— | (2-Ph-ethyl)NH—C(O)—O— |
| phenyl | H— | vinyl- |
| 4-CN—Ph— | H— | HO- |
| 4-(Me—C(O)—NH)—Ph— | H— | HO— |
| 4-i-propyl-Ph— | H— | HO— |
| 4-Et—Ph— | H— | HO— |
| 4-t-butyl-Ph— | H— | H— |
| n-dodecyl | H— | HO— |
| n-octyl | H— | H— |
| 4-MeO—Ph— | Ph—SO$_2$—NH— | H— |
| 4-MeO—Ph— | MeC(O)—NH— | HO— |
| 4-MeO—Ph— | MeO—C(O)—NH— | (4-F—Ph)NH—C(O)—O— |
| 4-MeO—Ph— | methyl | H— |
| 4-MeO—Ph— | Ph—C(O)—NH— | HO— |
| 4-MeO—Ph— | H— | benzyl |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeO—Ph— | H— | H— |
| 4-MeO—Ph— | H— | H— |
| 4-MeO—Ph— | H— | H— |
| 4-MeO—Ph— | EtO—C(O)— | H— |
| 4-MeO—Ph— | H— | HO— |
| 4-MeO—Ph— | H— | PhNH—C(O)—O— |
| 4-MeO—Ph— | methyl | PhNH—C(O)—O— |
| 4-MeS—Ph— | BzMeN—C(O)— | HO— |
| 4-Cl—Ph— | phenyl | Ph—SO$_2$—NH— |
| 4-CF$_3$O—Ph— | MeO—C(O)— | thienyl-S- |
| 5-benzodioxolyl | HO—C(O)— | HO— |
| 4-Me—Ph— | 2-pyridyl | HO— |
| 4-MeO—Ph— | 3-pyridyl | MeS— |

TABLE III-continued

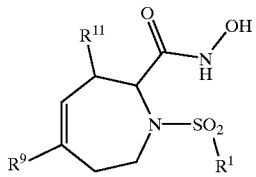

| R¹ | R⁹ | R¹¹ |
|---|---|---|
| 4-MeO—Ph— | 4-morpholino-C(O)— | HO— |
| n-dodecyl | BzO—C(O)— | HO— |
| 4-MeO—Ph— | Ph—NH—C(O)— | thienyl-NH—C(O)—O— |
| furyl | Bz—NH—C(O)— | HO— |
| 4-MeO—Ph— | 3-Ph-propyl-NH—C(O)— | 2-pyridyl-NH—C(O)—O— |
| 4-pyridyl | BzEtN—C(O)— | propargyl |
| 4-PhO—Ph— | (2-Ph-ethyl)(Me)N—C(O)— | HO— |
| 4-MeO—Ph— | (4,4-dimethyl pentyl)NHC(O)— | thienyl-O- |
| 4-MeO—Ph— | 3-pyridyl | HO— |
| 5-benzofuranyl | 4-morpholino-C(O)— | HO— |
| 4-MeO—Ph— | BzO—C(O)— | HO— |
| 5-benzo-thiazolyl | Ph—NH—C(O)— | (1-Ph-ethyl)NH—C(O)—O— |
| 4-MeO—Ph— | Bz—NH—C(O)— | HO— |
| 4-PhO—Ph— | 3-Ph-propyl-NH—C(O)— | HO— |
| 4-MeO—Ph— | (2-Ph-ethyl)(Me)N—C(O)— | vinyl |
| n-dodecyl | BzEtN—C(O)— | HO— |
| 4-MeO—Ph— | (4,4-dimethyl pentyl)NHC(O)— | PhNH—C(O)—O— |
| 4-morpholino | phenyl | PhNH—C(O)—O— |
| 2-naphthyl | 3-pyridyl | MeNH—C(O)—O— |
| 3,4-dimethoxy-phenyl | 4-morpholino-C(O)— | i-propylNH—C(O)—O— |
| 4-piperidinyl-butyl | BzO—C(O)— | (4-PhO—Ph)NH—C(O)—O— |
| 6-benzo-dioxanyl | Ph—NH—C(O)— | thienyl-NH—C(O)—O— |
| 4-hydroxy-cyclohexyl | 2-pyridyl-NH—C(O)— | (4-MeO—Ph)NH—C(O)—O— |
| 4-MeO—Ph— | BzMeN—C(O)— | 3-(3-furyl)-butyl |
| 4-MeO—Ph— | 3-pyridyl | 2-MeS-ethyl |
| 4-MeO—Ph— | 4-acetamido-phenyl | 4-methyl-pentyl |
| 4-MeO—Ph— | H— | PhNH—C(O)-ethyl |
| 4-MeO—Ph— | 4-chlorobenzyl | 4-pyrid-3-yl-butyl |
| 4-MeO—Ph— | 4-pyridyl | 3-hydroxy-butyl |
| 4-MeO—Ph— | H— | PhNH—C(O)-methyl |
| 4-MeO—Ph— | HO—C(O)— | 2-(pyrid-3-yl-C(O)—NH)-ethyl |
| 4-MeO—Ph— | phenyl | 2-(2-thienyl-thio)ethyl |
| 4-MeO—Ph— | 4-morpholino-C(O)— | PhNH—C(O)-methyl |
| 4-MeO—Ph— | 3-pyridyl | 3-MeS-propyl |
| 4-MeO—Ph— | EtO—C(O)— | 2-phenoxyethyl |
| 4-MeO—Ph— | Ph—NH—C(O)— | 3-pyrid-3-yl-propyl |
| 4-MeO—Ph— | 2-pyridyl-NH—C(O)— | iso-butyl |

TABLE IV

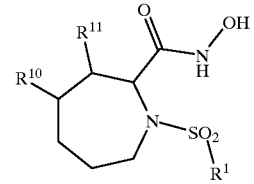

| R¹ | R¹⁰ | R¹¹ |
|---|---|---|
| 4-MeO-Ph- | BzMeN—C(O)— | HO— |
| 4-MeO-Ph- | phenyl | HO— |
| 4-MeO-Ph- | EtO—C(O)— | HO— |
| 4-MeO-Ph- | HO—C(O)— | HO— |
| 4-MeO-Ph- | 2-pyridyl | HO— |
| 4-CF₃O-Ph- | 3-pyridyl | H— |
| 4-MeO-Ph- | 4-morpholino-C(O)— | HO— |
| 4-MeO-Ph- | BzO—C(O)— | HO— |
| 4-Me-Ph- | Ph-NH—C(O)— | HO— |
| 3-MeO-Ph- | Bz-NH—C(O)— | HO— |
| 4-MeO-Ph- | (4,4-dimethyl pentyl)NHC(O)— | HO— |
| 4-Cl-Ph- | PhMeN—C(O)— | HO— |
| 2-thienyl | PhMeN—C(O)— | HO— |
| 4-MeO-Ph- | H— | BzNH—C(O)—O— |
| 3,4-dimethoxy-phenyl | H— | PhNH—C(O)—O— |
| 4-MeO-Ph- | H— | MeNH—C(O)—O— |
| 4-MeO-Ph- | H— | i-propylNH—C(O)—O— |
| 4-MeO-Ph- | H— | (4-PhO-Ph)NH—C(O)—O— |
| 4-MeO-Ph- | H— | (1-Ph-ethyl)NH—C(O)—O— |
| 4-MeO-Ph- | H— | (4-MeO-Ph)NH—C(O)—O— |
| 5-benzo-thiazolyl | H— | (2-Ph-ethyl)NH—C(O)—O— |
| phenyl | H— | vinyl- |
| 4-CN-Ph- | H— | HO— |
| 4-(Me-C(O)—NH)-Ph- | H— | HO— |
| 4-i-propyl-Ph- | H— | HO— |
| 4-Et-Ph- | H— | HO— |
| 4-t-butyl-Ph- | H— | H— |
| n-dodecyl | H— | HO— |
| n-octyl | H— | H— |
| 4-MeO-Ph- | Ph-SO₂—NH— | H— |
| 4-MeO-Ph- | MeC(O)—NH— | HO— |
| 4-MeO-Ph- | MeO—C(O)—NH— | (4-F-Ph)NH—C(O)—O— |
| 4-MeO-Ph- | methyl | H— |
| 4-MeO-Ph- | Ph-C(O)—NH— | HO— |
| 4-MeO-Ph- | H— | benzyl |
| 4-MeO-Ph- | H— | HO— |
| 4-MeO-Ph- | H— | PhNH—C(O)—O— |
| 4-MeO-Ph- | methyl | PhNH—C(O)—O— |
| 4-MeO-Ph- | H— | H— |
| 4-MeO-Ph- | EtO—C(O)— | H— |
| 4-MeS-Ph- | BzMeN—C(O)— | HO— |
| 4-Cl-Ph- | phenyl | Ph-SO₂—NH— |
| 4-CF₃O-Ph- | MeO—C(O)— | thienyl-S— |
| 5-benzo-dioxolyl | HO—C(O)— | HO— |
| 4-Me-Ph- | 2-pyridyl | HO— |
| 4-MeO-Ph- | 3-pyridyl | MeS— |
| 4-MeO-Ph- | 4-morpholino-C(O)— | HO— |
| n-dodecyl | BzO—C(O)— | HO— |
| 4-MeO-Ph- | Ph-NH—C(O)— | thienyl-NH—C(O)—O— |
| furyl | Bz-NH—C(O)— | HO— |
| 4-MeO-Ph- | 3-Ph-propyl-NH—C(O)— | 2-pyridyl-NH—C(O)—O— |

TABLE IV-continued

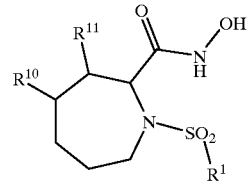

| R¹ | R¹⁰ | R¹¹ |
|---|---|---|
| 4-PhO-Ph- | (2-Ph-ethyl)(Me)N—C(O)— | HO— |
| 4-pyridyl | BzEtN—C(O)— | propargyl |
| 4-MeO-Ph- | (4,4-dimethylpentyl)NHC(O)— | thienyl-O— |
| 5-benzofuranyl | 4-morpholino-C(O)— | HO— |
| 5-benzothiazolyl | Ph-NH—C(O)— | (1-Ph-ethyl)NH—C(O)—O— |
| 4-PhO-Ph- | 3-Ph-propyl-NH—C(O)— | HO— |
| 4-MeO-Ph- | (2-Ph-ethyl)(Me)N—C(O)— | vinyl |
| n-dodecyl | BzEtN—C(O)— | HO— |
| 4-MeO-Ph- | (4,4-dimethylpentyl)NHC(O)— | PhNH—C(O)—O— |
| 4-morpholino phenyl | phenyl | PhNH—C(O)—O— |
| 3,4-dimethoxy-phenyl | 4-morpholino-C(O)— | i-propylNH—C(O)—O— |
| 4-piperidinyl-butyl | BzO—C(O)— | (4-PhO-Ph)NH—C(O)—O— |
| 6-benzodioxanyl | Ph-NH—C(O)— | thienyl-NH—C(O)—O— |
| 2-naphthyl | 3-pyridyl | MeNH—C(O)—O— |
| 4-hydroxy-cyclohexyl | 2-pyridyl-NH—C(O)— | (4-MeO-Ph)NH—C(O)—O— |
| 4-MeO-Ph- | BzMeN—C(O)— | 3-(3-furyl)-butyl |
| 4-MeO-Ph- | 4-acetamido-phenyl | 4-methyl-pentyl |
| 4-MeO-Ph- | 3-pyridyl | 2-MeS-ethyl |
| 4-MeO-Ph- | H— | PhNH—C(O)—ethyl |
| 4-MeO-Ph- | 4-chlorobenzyl | 4-pyrid-3-yl-butyl |
| 4-MeO-Ph- | 4-pyridyl | 3-hydroxybutyl |
| 4-MeO-Ph- | H— | PhNH—C(O)-methyl |
| 4-MeO-Ph- | HO—C(O)— | 2-(pyrid-3-yl-C(O)—NH)-ethyl |
| 4-MeO-Ph- | phenyl | 2-(2-thienyl-thio)ethyl |
| 4-MeO-Ph- | 3-pyridyl | 3-MeS-propyl |
| 4-MeO-Ph- | 4-morpholino-C(O)— | PhNH—C(O)—methyl |
| 4-MeO-Ph- | BtO—C(O)— | 2-phenoxyethyl |
| 4-MeO-Ph- | Ph-NH—C(O)— | 3-pyrid-3-yl-propyl |
| 4-MeO-Ph- | 2-pyridyl-NH—C(O)— | iso-butyl |

TABLE V

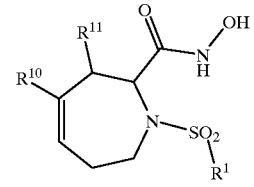

| R¹ | R¹⁰ | R¹¹ |
|---|---|---|
| 4-MeO-Ph- | BzMeN—C(O)— | HO— |
| 4-MeO-Ph- | phenyl | HO— |
| 4-MeO-Ph- | EtO—C(O)— | HO— |
| 4-MeO-Ph- | HO—C(O)— | HO— |
| 4-MeO-ph- | 2-pyridyl | HO— |
| 4-CF₃O-Ph- | 3-pyridyl | H— |
| 4-MeO-Ph- | BzO—C(O)— | HO— |
| 4-MeO-Ph- | 4-morpholino-C(O)— | HO— |
| 4-Me-Ph- | Ph-NH—C(O)— | HO— |
| 3-MeO-Ph- | Bz-NH—C(O)— | HO— |
| 4-MeO-Ph- | (4,4-dimethylpentyl)NHC(O)— | HO— |
| 4-Cl-Ph- | PhMeN—C(O)— | HO— |
| 2-thienyl | PhMeN—C(O)— | HO— |
| 4-MeO-Ph- | H— | BzNH—C(O)—O— |
| 3,4-dimethoxy-phenyl | H— | PhNH—C(O)—O— |
| 4-MeO-Ph- | H— | MeNH—C(O)—O— |
| 4-MeO-Ph- | H— | i-propylNH—C(O)—O— |
| 4-MeO-Ph- | H— | (4-PhO-Ph)NH—C(O)—O— |
| 4-MeO-Ph- | H— | (1-Ph-ethyl)NH—C(O)—O— |
| 4-MeO-Ph- | H— | (4-MeO-Ph)NH—C(O)—O— |
| 5-benzothiazolyl | H— | (2-Ph-ethyl)NH—C(O)—O— |
| phenyl | H— | vinyl- |
| 4-CN-Ph- | H— | HO— |
| 4-(Me-C(O)—NH)-Ph- | H— | HO— |
| 4-i-propyl-Ph- | H— | HO— |
| 4-Et-Ph- | H— | HO— |
| 4-t-butyl-Ph- | H— | H— |
| n-dodecyl | H— | HO— |
| n-octyl | H— | H— |
| 4-MeO-Ph- | Ph-SO₂—NH— | H— |
| 4-MeO-Ph- | MeC(O)—NH— | HO— |
| 4-MeO-Ph- | MeO—C(O)—NH— | (4-F-Ph)NH—C(O)—O— |
| 4-MeO-Ph- | methyl | H— |
| 4-MeO-Ph- | Ph-C(O)—NH— | HO— |
| 4-MeO-Ph- | H— | benzyl |
| 4-MeO-Ph- | H— | HO— |
| 4-MeO-Ph- | H— | PhNH—C(O)—O— |
| 4-MeO-Ph- | methyl | PhNH—C(O)—O— |
| 4-MeO-Ph- | H— | H— |
| 4-MeO-Ph- | H— | H— |
| 4-MeO-Ph- | EtO—C(O)— | H— |
| 4-MeS-Ph- | BzMeN—C(O)— | HO— |
| 4-Cl-Ph- | phenyl | Ph-SO₂—NH— |
| 4-CF₃O-Ph- | MeO—C(O)— | thienyl-S— |
| 5-benzodioxolyl | HO—C(O)— | HO— |
| 4-Me-Ph- | 2-pyridyl | HO— |
| 4-MeO-Ph- | 3-pyridyl | MeS— |
| 4-MeO-Ph- | 4-morpholino-C(O)— | HO— |

TABLE V-continued

[Structure: 7-membered ring with R10, R11 substituents, C(O)NHOH group, and N-SO2-R1]

| R¹ | R¹⁰ | R¹¹ |
|---|---|---|
| n-dodecyl | BzO—C(O)— | HO— |
| 4-MeO-Ph- | Ph-NH—C(O)— | thienyl-NH—C(O)—O— |
| 4-MeO-Ph- | 3-Ph-propyl-NH—C(O)— | 2-pyridyl-NH—C(O)—O— |
| furyl | Bz-NH—C(O)— | HO— |
| 4-PhO-Ph- | (2-Ph-ethyl)(Me)N—C(O)— | HO— |
| 4-pyridyl | BzEtN—C(O)— | propargyl |
| 4-MeO-Ph- | (4,4-dimethyl pentyl)NHC(O)— | thienyl-O— |
| 5-benzofuranyl | 4-morpholino-C(O)— | HO— |
| 5-benzothiazolyl | Ph-NH—C(O)— | (1-Ph-ethyl)NH—C(O)—O— |
| 4-PhO-Ph- | 3-Ph-propyl-NH—C(O)— | HO— |
| 4-MeO-Ph- | (2-Ph-ethyl)(Me)N—C(O)— | vinyl |
| n-dodecyl | BzEtN—C(O)— | HO— |
| 4-MeO-Ph- | (4,4-dimethyl pentyl)NHC(O)— | PhNH—C(O)—O— |
| 4-morpholino phenyl | phenyl | PhNH—C(O)—O— |
| 2-naphthyl | 3-pyridyl | MeNH—C(O)—O— |
| 3,4-dimethoxy-phenyl | 4-morpholino-C(O)— | i-propylNH—C(O)—O— |
| 4-piperidinyl-butyl | BzO—C(O)— | (4-PhO-Ph)NH—C(O)—O— |
| 6-benzodioxanyl | Ph-NH—C(O)— | thienyl-NH—C(O)—O— |
| 4-hydroxy-cyclohexyl | 2-pyridyl-NH—C(O)— | (4-MeO-Ph)NH—C(O)—O— |
| 4-MeO-Ph- | BzMeN—C(O)— | 3-(3-furyl)-butyl |
| 4-MeO-Ph- | 4-acetamido-phenyl | 4-methyl-pentyl |
| 4-MeO-Ph- | 3-pyridyl | 2-MeS-ethyl |
| 4-MeO-Ph- | H— | PhNH—C(O)—ethyl |
| 4-MeO-Ph- | 4-chlorobenzyl | 4-pyrid-3-yl-butyl |
| 4-MeO-Ph- | 4-pyridyl | 3-hydroxy-butyl |
| 4-MeO-Ph- | H— | PhNH—C(O)—methyl |
| 4-MeO-Ph- | HO—C(O)— | 2-(pyrid-3-yl-C(O)—NH)-ethyl |
| 4-MeO-Ph- | phenyl | 2-(2-thienyl-thio)ethyl |
| 4-MeO-Ph- | 3-pyridyl | 3-MeS-propyl |
| 4-MeO-Ph- | 4-morpholino-C(O)— | PhNH—C(O)—methyl |
| 4-MeO-Ph- | EtO—C(O)— | 2-phenoxyethyl |
| 4-MeO-Ph- | Ph-NH—C(O)— | 3-pyrid-3-yl-propyl |
| 4-MeO-Ph- | 2-pyridyl-NH—C(O)— | iso-butyl |

TABLE VI

[Structure: 8-membered ring with R10, R12 substituents, C(O)NHOH group, and N-SO2-R1]

| R¹ | R¹⁰ | R¹² |
|---|---|---|
| 4-MeO-Ph- | BzMeN—C(O)— | HO— |
| 4-MeO-Ph- | phenyl | HO— |
| 4-MeO-Ph- | EtO—C(O)— | HO— |
| 4-MeO-Ph- | HO—C(O)— | HO— |
| 4-MeO-Ph- | 2-pyridyl | HO— |
| 4-CF₃O-Ph- | 3-pyridyl | H— |
| 4-MeO-Ph- | 4-morpholino-C(O)— | HO— |
| 4-MeO-Ph- | BzO—C(O)— | HO— |
| 4-Me-Ph- | Ph-NH—C(O)— | HO— |
| 3-MeO-Ph- | Bz-NH—C(O)— | HO— |
| 4-MeO-Ph- | (4,4-dimethyl pentyl)NHC(O)— | HO— |
| 4-Cl-Ph- | PhMeN—C(O)— | HO— |
| 2-thienyl | PhMeN—C(O)— | HO— |
| 3,4-dimethoxy-phenyl | H— | PhNH—C(O)—O— |
| 4-MeO-Ph- | H— | BzNH—C(O)—O— |
| 4-MeO-Ph- | H— | i-propylNH—C(O)—O— |
| 4-MeO-Ph- | H— | (4-PhO-Ph)NH—C(O)—O— |
| 4-MeO-Ph- | H— | MeNH—C(O)—O— |
| 4-MeO-Ph- | H— | (1-Ph-ethyl)NH—C(O)—O— |
| 4-MeO-Ph- | H— | (4-MeO-Ph)NH—C(O)—O— |
| 5-benzothiazolyl | H— | (2-Ph-ethyl)NH—C(O)—O— |
| phenyl | H— | vinyl- |
| 4-CN-Ph- | H— | HO— |
| 4-(Me-C(O)—NH)-Ph- | H— | HO— |
| 4-i-propyl-Ph- | H— | HO— |
| 4-Et-Ph- | H— | HO— |
| 4-t-butyl-Ph- | H— | H— |
| n-dodecyl | H— | HO— |
| n-octyl | H— | H— |
| 4-MeO-Ph- | Ph-SO₂—NH— | HO— |
| 4-MeO-Ph- | MeC(O)—NH— | HO— |
| 4-MeO-Ph- | MeO—C(O)—NH— | (4-F-Ph)NH—C(O)—O— |
| 4-MeO-Ph- | methyl | H— |
| 4-MeO-Ph- | Ph-C(O)—NH— | HO— |
| 4-MeO-Ph- | H— | benzyl |
| 4-MeO-Ph- | H— | HO— |
| 4-MeO-Ph- | H— | PhNH—C(O)—O— |
| 4-MeO-Ph- | methyl | PhNH—C(O)—O— |
| 4-MeO-Ph- | H— | H— |
| 4-MeO-Ph- | H— | H— |
| 4-MeO-Ph- | EtO—C(O)— | H— |
| 4-MeS-Ph- | BzMeN—C(O)— | HO— |
| 4-Cl-Ph- | phenyl | Ph-SO₂—NH— |
| 4-CF₃O-Ph- | MeO—C(O)— | thienyl-S— |
| 5-benzodioxolyl | HO—C(O)— | HO— |
| 4-Me-Ph- | 2-pyridyl | HO— |
| 4-MeO-Ph- | 3-pyridyl | MeS— |
| 4-MeO-Ph- | 4-morpholino-C(O)— | HO— |
| 4-MeO-Ph- | Ph-NH—C(O)— | thienyl-NH—C(O)—O— |
| n-dodecyl | BzO—C(O)— | HO— |
| furyl | Bz-NH—C(O)— | HO— |
| 4-MeO-Ph- | 3-Ph-propyl-NH—C(O)— | 2-pyridyl-NH—C(O)—O— |

TABLE VI-continued

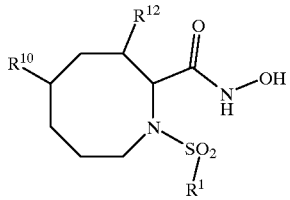

| R¹ | R¹⁰ | R¹² |
|---|---|---|
| 4-PhO-Ph- | (2-Ph-ethyl)(Me)N—C(O)— | HO— |
| 4-pyridyl | BzEtN—C(O)— | propargyl |
| 4-MeO-Ph- | (4,4-dimethylpentyl)NHC(O)— | thienyl-O— |
| 5-benzofuranyl | 4-morpholino-C(O)— | HO— |
| 5-benzothiazolyl | Ph-NH—C(O)— | (1-Ph-ethyl)NH—C(O)—O— |
| 4-PhO-Ph- | 3-Ph-propyl-NH—C(O)— | HO— |
| 4-MeO-Ph- | (2-Ph-ethyl)(Me)N—C(O)— | vinyl |
| 4-MeO-Ph- | (4,4-dimethylpentyl)NHC(O)— | PhNH—C(O)—C— |
| n-dodecyl | BzEtN—C(O)— | HO— |
| 4-morpholino | phenyl | PhNH—C(O)—O— |
| 2-naphthyl | 3-pyridyl | MeNH—C(O)—O— |
| 3,4-dimethoxyphenyl | 4-morpholino-C(O)— | i-propylNH—C(O)—O— |
| 4-piperidinyl-butyl | BzO—C(O)— | (4-PhO-Ph)NH—C(O)—O— |
| 6-benzodioxanyl | Ph-NH—C(O)— | thienyl-NH—C(O)—O— |
| 4-hydroxycyclohexyl | 2-pyridyl-NH—C(O)— | (4-MeO-Ph)NH—C(O)—O— |
| 4-MeO-Ph- | 3-pyridyl | 2-MeS-ethyl |
| 4-MeO-Ph- | BzMeN—C(O)— | 3-(3-furyl)-butyl |
| 4-MeO-Ph- | 4-acetamidophenyl | 4-methylpentyl |
| 4-MeO-Ph- | H— | PhNH—C(O)—ethyl |
| 4-MeO-Ph- | 4-chlorobenzyl | 4-pyrid-3-yl-butyl |
| 4-MeO-Ph- | 4-pyridyl | 3-hydroxybutyl |
| 4-MeO-Ph- | H— | PhNH—C(O)—methyl |
| 4-MeO-Ph- | HO—C(O)— | 2-(pyrid-3-yl-C(O)—NH)-ethyl |
| 4-MeO-Ph- | phenyl | 2-(2-thienyl-thio)ethyl |
| 4-MeO-Ph- | 3-pyridyl | 3-MeS-propyl |
| 4-MeO-Ph- | 4-morpholino-C(O)— | PhNH—C(O)—methyl |
| 4-MeO-Ph- | EtO—C(O)— | 2-phenoxyethyl |
| 4-MeO-Ph- | Ph-NH—C(O)— | 3-pyrid-3-yl-propyl |
| 4-MeO-Ph- | 2-pyridyl-NH—C(O)— | iso-butyl |

EXAMPLE 31

The following assays are in vitro assays which were used to characterize the ability of compounds of this invention to inhibit the production of TNF-α by monocytes following LPS stimulation, Human Monocyte TNF Convertase Assay, Human Neutrophil Collagenase Assay and Human Fibroblast Stromelysin Assay.

Lipopolysaccharide-activated Monocyte TNF Production Assay

Isolation of Monocytes

Test compounds were evaluated in vitro for the ability to inhibit the production of tumor necrosis factor (TNF) by monocytes activated with bacterial lipopolysaccharide (LPS). Fresh residual source leukocytes (a byproduct of plateletpheresis) were obtained from the local blood bank and peripheral blood mononuclear cells (PBMCs) were isolated by density gradient centrifugation on Ficol-Paque Plus (Pharmacia). PBMCs were suspended at $2 \times 10^6$/ml in DMEM supplemented to contain 2% FCS (10 mM), 0.3 mg/ml glutamate, 100 U/ml penicillin G and 100 mg/ml streptomycin sulfate (complete media). Cells were plated into Falcon flatbottom 96 well culture plates (200 μl/well) and cultured overnight at 37° C. and 6% $CO_2$. Nonadherent cells were removed by washing with 200 μl/well of fresh medium. Wells containing adherent cells (~70% monocytes) were replenished with 100 μl of fresh medium.

Preparation of Test Compound Stock Solutions

Test compounds were dissolved in DMS. Compound stock solutions were prepared to an initial concentration of 10–50 μM. Stocks were diluted initially to 20–200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μl complete medium. Monocytes were cultured with test compounds for 60 min at which time 25 μl of complete medium containing 30 ng/ml lipopolysaccharide from *E. coli* K532 were added to each well. Cells were cultured an additional 4 hrs. Culture supernatants were then removed and TNF present in the supernatants was quantified using an ELISA.

TNF ELISA

Flat bottom 96 well Corning High Binding ELISA plates were coated overnight (4° C.) with 150 μL/well of 3 μg/ml murine anti-human TNFa MAb (R&D Systems #MAB210). Wells were then blocked 1 h at room temperature with 200 μL/well of $CaCl_2$-free ELISA buffer supplemented to contain 20 mg/ml BSA (standard ELISA buffer: 20 mM, 150 mM NaCl, 2 mM $CaCl_2$, 0.15 mM thimerosal, pH 7.4). Plates were washed and replenished with 100 μl of test supernatants (diluted 1:3) or standards. Standards consisted of eleven 1.5-fold serial dilutions from a stock of 1 ng/ml recombinant human TNF (R&D Systems). Plates were incubated at room temperature for 1 h on orbital shaker (300 rpm), washed and replenished with 100 μl/well of 0.5 μg/ml goat anti-human TNFa (R&D systems #AB-210-NA) biotinylated at a 4:1 ratio. Plates were incubate for 40 min, washed and replenished with 100 μl/well of alkaline phosphatase-conjugated streptavidin (Jackson ImmunoResearch #016-050-084) at 0.02 μg/ml. Plates were incubated 30 min, washed and replenished with 200 μl/well of 1 mg/ml of p-nitrophenyl phosphate. After 30 min, plates were read at 405 nm on a Vmax plate reader.

Data Analysis

Standard curve data were fit to a second order polynomnial and unknown TNFa conentrations determined from their OD by solving this equation for concentration. TNF concentrations were then plotted vs. test compound concentration using a second order polynomial. This equation was then used to calculate the concentration of test compounds causing a 50% reduction in TNF production.

Hunan Monocyte TNF Convertase Assay

TNF convertase activity is demonstrated by hydrolytic cleavage of a dinitrophenyl (DNP)-labeled peptide substrate between amino acids Ala and Val. Dependent on the purity of the TNF convertase used in the reaction, hydrolysis of incorrectly clipped DNP-peptides are also possible. Human monocyte TNF convertase activity is determined by using DNP-labeled peptide substrate (1) DNP-SPLAQAVRSSSR-CONH2; and clipped peptides: (2) DNP-SPLAQ-COOH (incorrectly clipped between Gln and Ala); (3) DNP-SPLAQA-COOH (correctly clipped); and (4) DNP-SPLAQAV-COOH (incorrectly clipped between Val and Arg).

Full length and clipped DNP-peptides are separated and quantitated using reversed phase HPLC, monitoring at 350 nM (where dinitrophenyl absorbs). Inhibitors of TNF convertase in the reaction are detected by a decrease in peak height of peptide 3 and an increase in peak height of peptide 1. Inhibition is calculated as percent of control by comparing peak height of peptide 3 in samples with no inhibitors (control conditions) and peak height of peptide no. 3 in samples with inhibitors.

Typically, compounds at 2 mM in DMSO are first diluted 1:11.8 in 40 mM Tris, pH 7.5. A further 1:17 dilution of the compound occurs in the final reaction mixture. This reaction mixture contains 2.5 µL of the diluted compound, 20 µL of peptide 1, and 20 µL of TNF convertase. This results in a compound concentration of 10 µM, 0.5% DMSO, in the final reaction volume. Compounds are initially screened at 10 uM and selected compounds are further assayed to determine an $MIC_{50}$.

Human Neutrophil Collagenase Assay

Human neutrophil collagenase (HNC) activity is determined by using fluorogenic peptide substrate Dnp-Pro-b-Cyclohexyl-Ala-Gly-Cys (Me)-His-Ala-Lys-(N-methylanthranilic acid)-$NH_2$. The N-terminus Dnp group and the C-terminus N-methyl-anthranilyl moiety (Nma) are fluorescence self-quenching until the peptide is cleaved at the Gly-Cys(me) bond. The fluorescence from the cleavage products is measured on a Bio-Tek Instrument FL500 fluorescence micro-plate reader (excitation at 360 nm, emission at 460 nm). The assay is performed in a 96-well plate (in duplicate), and the Km=51 nM for the substrate, and Ki=722 nM for Actinonin have been determined. The test compounds (at 100, 33 & 10 mM) are compared for their inhibition of HNC activity on the substrate against the activity of Actinonin and Ki's were determined on selected compounds.

Human Fibroblast Stromelysin Assay

Human fibroblast stromelysin (HFS) activity is determined by using fluorogenic peptide substrate Dnp-Pro-b-Cyclohexyl-Ala-Gly-Cys(Me)-His-Ala-Lys-(N-methylanthranilic acid)-$NH_2$. The N-terminus Dnp group and the C-terminus N-methyl-anthranilyl moiety (Nma) are fluorescence self-quenching until the peptide is cleaved at the Gly-Cys(me) bond. The fluorescence from the cleavage products is measured on a Bio-Tek Instrument FL500 fluorescence micro-plate reader (excitation at 360 nm, emission at 460 nm). The assay is performed in a 96-well plate (in duplicate), and the Km=51 nM for the substrate, and Ki=722 nM for Actinonin (an inhibitor of enzyme activity; Sigma Chemical, St. Louis, Mo.; A6671) have been determined as the standard control. The test compounds (at 100, 33 & 10 mM) are compared for their inhibition of HFS activity on the substrate against the activity of Actinonin and Ki's were determined on selected compounds.

Inhibition of LPS-Induced TNF-α Production in Mice

Male DBA/1LACJ mice were dosed with vehicle or test compounds in a vehicle (the vehicle consisting of 0.5% tragacanth in 0.03 N HCl) prior to lipopolysaccharide (2 mg/kg, I.V.) injection. Ninety minutes after LPS injection, blood was collected and the serum was analyzed by ELISA for TNF levels.

The following compounds had a TNF convertase, HNC and/or HFS inhibition activity $IC_{50}$ of less than 10 µM:

Cis-3-Benzyl-1-(4-methoxybenzenesulfonyl)-azepane-2-hydroxamic acid;

Trans-3-Benzyl-1-(4-methoxybenzenesulfonyl)-azepane-2-hydroxamic acid;

Trans-3-Phenyl-1-(4-methoxybenzenesulfonyl)-azepane-2-hydroxamic acid;

1-(4-methoxybenzenesulfonyl)-azepane-2-hydroxamic acid;

Acetic acid 2-hydroxycarbamoyl-1-(4-methoxy-benzenesulfonyl)-azepan-3-ylmethyl ester;

3-Hydroxymethyl-1-(4-methoxy-benzenesulfonyl)-azepane-2-carboxylic acid hydroxamide;

3-Benzyloxymethyl-1-(4-methoxy-benzenesulfonyl)-azepane-2-carboxylic acid hydroxyamide;

1-(4-Methoxy-benzenesulfonyl)-3-phenylsulfanylmethyl-azepane-2-carboxylic acid hydroxyamide;

1-(4-Methoxy-benzenesulfonyl)-3-styryl-azepane-2-carboxylic acid hydroxyamide;

3-(2-Hydroxycarbamoyl-1-(4-methoxy-benzenesulfonyl)-azepan-3-yl)-acrylic acid;

Acetic acid 2-hydroxycarbamoyl-1-(4-methoxy-benzene sulfonyl)-2,3,4,7-tetrahydro-1H-azepin-3-ylmethyl ester;

3-Hydroxymethyl-1-(4-methoxy-benzenesulfonyl)-2,3,4,7-tetrahydro-1H-azepine-2-carboxylic acid hydroxyamide;

3-Benzyloxymethyl-1-(4-methoxy-benzenesulfonyl)-2,3,4,7-tetrahydro-1H-azepine-2-carboxylic acid hydroxyamide;

1-(4-Methoxy-benzenesulfonyl)-3-phenylsulfanylmethyl-2,3,4,7-tetrahydro-1H-azepine-2-carboxylic acid hydroxyamide;

3-Benzofuran-2-yl-1-(4-methoxy-benzenesulfonyl)-2,3,4,7-tetrahydro-1H-azepine-2-carboxylic acid hydroxyamide;

1-(4-Methoxy-benzenesulfonyl)-azepane-2,3-dicarboxylic acid 2-(hydroxamide) 3-(phenmethylamide);

1-(4-Methoxy-benzenesulfonyl)-azepane-2,3-dicarboxylic acid 2-(hydroxamide) 3-(phenethylamide);

1-(4-Methoxy-benzenesulfonyl)-azepane-2,3-dicarboxylic acid 2-(hydroxamide) 3-(phenpropylamide);

1-(4-Methoxy-benzenesulfonyl)-azepane-2,3-dicarboxylic acid 2-(hydroxamide) 3-(4-phenoxy-2-ethylamide);

1-(4-Methoxy-benzenesulfonyl)-azepane-2,3-dicarboxylic acid 2-(hydroxamide) 3-(phenylmethylsulfanylethylamide);

1-(4-Methoxy-benzenesulfonyl)-azepane-2,3-dicarboxylic acid 2-(hydroxamide) 3-(4-Phenoxyphenethylamide);

Cis-3-(4-Phenylbenzyl)-1-(4-methoxybenzenesulfonyl)-azepane-2-hydroxamic acid;

Trans-3-(4-Phenylbenzyl)-1-(4-methoxybenzenesulfonyl)-azepane-2-hydroxamic acid;

Trans-3-Methyl-1-(4-methoxybenzenesulfonyl)-azepane-2-hydroxamic acid;

(2-Hydroxycarbamoyl-1-(4-methoxybenzenesulfonyl)-2,3,4,7-tetrahydro-1H-azepine-3-yl)-carbamic acid benzyl ester; and 3-(Hydroxy-phenyl-methyl)-1-(4-methoxy-benzenesulfonyl)-2,3,4,7-tetrahydro-1H-azepine-2-hydroxamic acid.

Selected compounds from this invention have demonstrated in vivo activity in a LPS mouse model in which serum levels of TNF-α were reduced in the presence of compounds of this invention. The compounds from this invention can be shown to have antiinflammatory activity in a adjuvant arthritis model.

Methods of Treatment

All of the compounds of this invention are useful in the prophylaxis and treatment of TNF-α mediated disease states. The compounds are also useful in the prophylaxis and treatment of disease states in which HNC and/or HFS play a role. Preferably, the compounds of this invention are useful in the prophylaxis and treatment of rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those viruses sensitive to TNF-α inhibition - HIV-1, HIV-2, HIV-3, cytomegalovirus (CMV), influenza, adenovirus, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; brain trauma; atherosclerosis; Alzheimer's disease; multiple sclerosis; cerebral malaria; sepsis; septic shock; toxic shock syndrome; fever and mylagias due to infection.

The present invention provides a method of treating a disease state in which TNF-a, HNC and/or HFS levels are elevated which comprises administering an effective amount of a compound of this invention. Compounds of this invention are of use in the prophylaxis and acute or chronic therapy of any disease state in a human, or other mammal, which is exacerbated by or mediated by elevated or unregulated TNF-a, HNC and/or HFS by mammal's cells. More preferably, this invention relates to a method of lowering the levels of TNF-α in a mammal in need thereof which comprises administering an effective dose of a compound of this invention or a pharmaceutical composition thereof. In addition, this invention relates to a method of lowering the activity levels of HNC and/or HFS in a mammal in need thereof which comprises administering an effective dose of a compound of this invention or a pharmaceutical composition thereof.

A compound of this invention or a pharmaceutical composition thereof is useful in the treatment or prophylaxis of a number of disease states including rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those viruses sensitive to TNF-α inhibition - HIV-1, HIV-2, HIV-3, cytomegalovirus (CMV), influenza, adenovirus, and the herpes viuses including HSV-1, HSV-2, and herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; fever and mylagias due to infection.

Pharmaceutical Compositions

This invention further relates to the use of a compound of this invention in the manufacture of a medicament for the prophylaxis and treatment, either acutely or chronically, of TNF-α mediated disease states. In addition, the compounds of this invention are useful in the manufacture of a medicament for treating disease states in which HNC and/or HFS play a role.

This invention also relates to a pharmaceutical composition comprising a compound of this invention and a pharmaceutically acceptable carrier, and if desired other active ingredients. The compounds of this invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art.

For the prophylaxis and treatment of disease states, the compounds of the present invention may be administered orally, parentally, or by inhalation spray, rectally, or topically in dosage unit formulations containing conventional pharmaceutically acceptable carriers, adjuvants and vehicles. The term parenteral as used herein includes, subcutaneous, intravenous, intramuscular, intrasternal, infusion techniques or intraperitoneally.

The amount of active ingredient that may be combined with the carrier materials to produce a single dosage form will vary depending upon the host treated and the particular mode of administration.

The dosage regimen for treating a disease state with the compounds of this invention and/or compositions of this invention is based on a variety of factors, including the type of disease, the age, weight, sex and medical condition of the patient, the severity of the condition, the route of administration, pharmacological considerations such as the activity, efficacy, pharmacokinetic and toxicology profiles of the particular compound employed, whether a drug delivery system is utilized and whether the compound is administered as part of a drug combination. Thus the dosage regimen may vary widely. Dosage levels of the order from about 0.01 mg to 80 mg per kilogram of body weight per day, preferably from about 0.5 mg to 30 mg/kg, more preferably from about 1 mg to 15 mg/kg are useful for all methods of use disclosed herein. The pharmaceutically active compounds of this invention can be processed in accordance with convential methods of pharmacy to produce medicinal agents for administration to patients, mammals including humans.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 250 mg, preferably from about 25 to 150 mg. A suitable daily dose for a human or other mammal may vary widely depending on the condition of the patient and other factors.

The compounds of this invention may also be administered by injection as a composition with suitable carriers including saline, dextrose, or water. The daily parenteral dosage regimen wll be from about 0.1 to about 80 mg/kg of total body weight, preferably from about 0.5 to about 30 mg/kg, and more preferably from about 1 mg to 15 mg/kg.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

A suitable topical dose of compounds of this invention is 0.1 mg to 150 mg administered one to four, preferably two or three times daily. For topical administration, the active ingredient may comprise from 0.001% to 10% w/w, e.g. from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid peparations suitable for penetration through the skin such as liniments, lotions, ointments, creams, or pastes and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, sodium, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, benzyl alcohol, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form including granules, powders or suppositories or in a liquid form such as solutions, suspensions, or emulsions. The pharmaceutical compositions may be subjected to conventional pharmaceutical operations such as sterilization and/or may contain conventional adjuvants, such as preservatives, stabilizers, wetting agents, emulsifiers, buffers, etc.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more other agents. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of formula

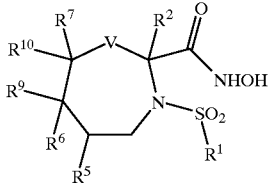

or a pharmaceutically acceptable salt thereof, wherein $R^1$ is (1) an alkyl, alkenyl, alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by a monocyclic heteroaryl or heterocyclyl radical of 5–6 ring members each of which is optionally substituted by a phenyl radical or monocyclic heteroaryl radical of 5–6 ring members; or (3) a heteroaryl radical optionally substituted by a phenyl or a monocyclic heteroaryl or heterocyclyl radical of 5–6 ring members each of which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, alkanoylamino, alkylsulfonylamino, alkoxycarbonylamino, alkoxycarbonyl, cyano, halo, azido, alkyl or haloalkyl; provided that the total number of phenyl, aryl, heteroaryl, cycloalkyl and heterocyclyl radicals in $R^1$ is 0–3;

wherein each $R^3$ is independently an alkyl, haloalkyl, aryl, heteroaryl, aryl-alkyl or heteroaryl-alkyl radical, wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy; and each $R^4$ is independently a hydrogen or alkyl radical;

$R^2$ is a hydrogen or alkyl radical;

V is —CR$^8$R$^{11}$— or —CR$^8$R$^{11}$—CHR$^{12}$—; wherein R$^{11}$ and R$^{12}$ are each independently (1) a hydrogen, —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, cycloalkyl, aryl or heteroaryl radical; or (2) an alkyl, alkenyl or alkynyl radical optionally substituted with 1–3 radicals of —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, aryl or heteroaryl; wherein the cycloalkyl, aryl and heteroaryl radicals of (1) and (2) are optionally substituted by 1–3 radicals of hydroxy, alkoxy, alkylthiol, amino, alkanoylamino, alkylsulfonylamino, alkoxycarbonylamino, alkoxycarbonyl, cyano, halo, azido, alkyl, haloalkyl or haloalkoxy;

wherein each $R^{20}$ is independently a hydrogen, alkyl, alkenyl, aryl, heteroaryl, aryl-alkyl, heteroaryl-alkyl, alkanoyl, aroyl or heteroaroyl radical; wherein the alkyl and alkenyl radicals are optionally substituted by —C(O)R$^{22}$; and wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy; and each $R^{21}$ is independently an alkyl, alkyl-C(O)R$^{22}$, aryl, heteroaryl, aryl-alkyl or heteroaryl-alkyl radical; wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

wherein each $R^{22}$ is independently a hydroxy, alkoxy, aryloxy, aryl-alkoxy, heteroaryloxy, heteroaryl-alkoxy or —NR$^{23}$R$^{24}$ radical; wherein each R$^{23}$ is independently a hydrogen, alkyl, aryl, aryl-alkyl, heteroaryl or heteroaryl-alkyl radical; and each R$^{24}$ is independently a hydrogen or alkyl radical; or —NR$^{23}$R$^{24}$ represents a heterocyclyl or heteroaryl radical; wherein the heterocyclyl, aryl and heteroaryl radicals of R$^{22}$, R$^{23}$ and —NR$^{23}$R$^{24}$ are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy; and $R^5$, $R^6$, $R^7$ and $R^8$ are each independently a hydrogen or alkyl radical; or one of CR$^5$—CR$^6$, CR$^6$—CR$^7$ or CR$^7$—CR$^8$ is C=C;

wherein $R^9$ and $R^{10}$ are each independently -B-A, provided that the combined total number of aryl, heteroaryl, cycloalkyl and heterocyclyl radicals in R$^9$, R$^{10}$, R$^{11}$ and R$^{12}$ is 0–3;

wherein each B is independently a
(1) bond;
(2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and/or (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;
(3) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl, haloalkyl or haloalkoxy; or
(4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;

each A is independently a
(1) hydrogen radical;
(2) halo, cyano or nitro radical;
(3) —C(O)—R$^{30}$, —C(O)—OR$^{31}$, —C(O)—NR$^{32}$R$^{31}$ or —C(NR$^{32}$)—NR$^{32}$R$^-$radical;
(4) —OR$^{31}$, —O—C(O)—R$^{31}$, —O—C(O)—NR$^{32}$R$^{31}$ or —O—C(O)—NR$^{33}$—S(O)$_2$—R$^{30}$ radical;

(5) —SR$^{31}$, —S(O)—R$^{30}$, S(O)$_2$—R$^{30}$, —S(O)$_2$—NR$^{32}$R$^{31}$, —S(O)$_2$R$^{33}$—C(O)—R$^{31}$, —S(O)$_2$—NR$^{33}$—C(O)—OR$^{30}$ or —S(O)$_2$—NR$^{33}$—C(O)—NR$^{32}$R$^{31}$ radical; or (6) —NR$^{32}$R$^{31}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—C(NR$^{32}$)—NR$^{32}$R$^{31}$, —NR$^{33}$—S(O)$_2$—R$^{30}$ or —NR$^{33}$—S(O)$_2$—NR$^{32}$R$^{31}$ radical;

wherein each R$^{30}$ is independently (1) alkyl, alkenyl or alkynyl radical optionally substituted by 1–3 radicals of —CO$_2$R$^{34}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonylamino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy;

(2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

each R$^{31}$ is independently hydrogen radical or R$^{30}$;

wherein each R$^{32}$ is independently (1) hydrogen radical;

(2) alkyl, alkenyl or alkynyl radical optionally substituted by 1–3 radicals of amino, alkylamino, dialkylamino, hydroxy, alkoxy, alkylthio, cyano or halo; or (3) aryl, heteroaryl, arylalkyl, heteroarylalkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, cyano, alkyl, haloalkyl or haloalkoxy; and each R$^{33}$ is independently (1) hydrogen radical;

(2) alkyl radical optionally substituted by a radical of heterocyclyl, aryl or heteroaryl which is optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; or (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; and each R$^{34}$ is independently hydrogen, alkyl, aryl, heteroaryl, arylalkyl or heteroarylalkyl radical, wherein the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy.

2. The compound of claim 1 or a pharmaceutically acceptable salt thereof, wherein R$^1$ is (1) an C$_1$–C$_{12}$ alkyl, C$_2$–C$_{12}$ alkenyl, C$_2$–C$_{12}$ alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by a monocyclic heteroaryl or heterocyclyl radical of 5–6 ring members each of which is optionally substituted by a phenyl radical or monocyclic heteroaryl radical of 5–6 ring members; or (3) a heteroaryl radical optionally substituted by a phenyl or a monocyclic heteroaryl or heterocyclyl radical of 5–6 ring members each of which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, C$_1$–C$_8$ alkanoylamino, C$_1$–C$_8$ alkylsulfonylamino, C$_1$–C$_8$ alkoxycarbonylamino, C$_1$–C$_8$ alkoxycarbonyl, cyano, halo, azido, C$_1$–C$_8$ alkyl or C$_1$–C$_8$ haloalkyl of 1–3 halo radicals; provided that the total number of phenyl, aryl, heteroaryl, cycloalkyl and heterocyclyl radicals in R$^1$ is 0–3;

wherein each R$^3$ is independently a C$_1$–C$_8$ alkyl, C$_1$–C$_8$ haloalkyl of 1–3 halo radicals, aryl, heteroaryl, aryl-C$_1$–C$_4$-alkyl or heteroaryl-C$_1$–C$_4$-alkyl radical, wherein the aryl and heteroaryl radicals are optionally substituted by 1–3 radicals of hydroxy, C$_1$–C$_4$ alkoxy, C$_1$–C$_4$ alkylthiol, amino, C$_1$–C$_8$ alkanoylamino, C$_1$–C$_8$ alkylsulfonylamino, C$_1$–C$_4$ alkylsulfinyl, C$_1$–C$_4$ alkylsulfonyl, C$_1$–C$_8$ alkoxycarbonylamino, C$_1$–C$_8$ alkoxycarbonyl, cyano, halo, azido, C$_1$–C$_8$ alkyl, C$_1$–C$_8$ haloalkyl of 1–3 halo radicals or C$_1$–C$_8$ haloalkoxy of 1–3 halo radicals; and each R$^4$ is independently a hydrogen or C$_1$–C$_8$ alkyl radical;

R$^2$ is a hydrogen or C$_1$–C$_4$ alkyl radical;

V is —CR$^8$R$^{11}$— or —CR$^8$R$^{11}$—CHR$^{12}$—; wherein R$^{11}$ and R$^{12}$ are each independently (1) a hydrogen, —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, cycloalkyl, aryl or heteroaryl radical; or (2) an C$_1$–C$_8$ alkyl, C$_2$–C$_8$ alkenyl or C$_2$–C$_8$ alkynyl radical optionally substituted with 1–3 radicals of —OR$^{20}$, —SR$^{21}$, —C(O)R$^{22}$, —NR$^{33}$—C(O)—R$^{31}$, —NR$^{33}$—C(O)—OR$^{30}$, —NR$^{33}$—C(O)—NR$^{32}$R$^{31}$, —NR$^{33}$—S(O)$_2$—R$^{30}$, —NR$^{33}$—S(O)$_2$—NR$^{32}$R$^{31}$, aryl or heteroaryl; wherein the cycloalkyl, aryl and heteroaryl radicals of (1) and (2) are optionally substituted by 1–3 radicals of hydroxy, C$_1$–C$_4$ alkoxy, C$_1$–C$_4$ alkylthiol, amino, C$_1$–C$_8$ alkanoylamino, C$_1$–C$_8$ alkylsulfonylamino, C$_1$–C$_8$ alkylsulfinyl, C$_1$–C$_4$ alkylsulfonyl, C$_1$–C$_8$ alkoxycarbonylamino, C$_1$–C$_8$ alkoxycarbonyl, cyano, halo, azido, C$_1$–C$_8$ alkyl, C$_1$–C$_8$ haloalkyl of 1–3 halo radicals or C$_1$–C$_8$ haloalkoxy of 1–3 halo radicals;

wherein each R$^{20}$ is independently a hydrogen, C$_1$–C$_8$ alkyl, C$_2$–C$_8$ alkenyl, aryl, heteroaryl, aryl-C$_1$–C$_4$- alkyl, heteroaryl-$C_1$–$C_4$-alkyl, $C_1$–$C_8$ alkanoyl, aroyl or heteroaroyl radical; wherein the alkyl and alkenyl radicals are optionally substituted by —C(O)$R^{22}$; and wherein the aryl and heteroaryl radicals are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals; and each $R^{21}$ is independently a $C_1$–$C_8$ alkyl, $C_1$–$C_8$ alkyl-C(O)$R^{22}$, aryl, heteroaryl, aryl-$C_1$–$C_4$-alkyl or heteroaryl-$C_1$–$C_4$-alkyl radical; wherein the aryl and heteroaryl radicals are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals;

wherein each $R^{22}$ is independently a hydroxy, $C_1$–$C_8$ alkoxy, aryloxy, aryl-$C_1$–$C_4$-alkoxy, heteroaryloxy, heteroaryl-$C_1$–$C_4$-alkoxy or —$NR^{23}R^{24}$ radical; wherein each $R^{23}$ is independently a hydrogen, $C_1$–$C_8$ alkyl, aryl, aryl-$C_1$–$C_4$-alkyl, heteroaryl or heteroaryl-$C_1$–$C_4$-alkyl radical; and each $R^{24}$ is independently a hydrogen or $C_1$–$C_8$ alkyl radical; or —$NR^{23}R^{24}$ represents a heterocyclyl or heteroaryl radical; wherein the heterocyclyl, aryl and heteroaryl radicals of $R^{22}$, $R^{23}$ and —$NR^{23}R^{24}$ are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals; and $R^5$, $R^6$, $R^7$ and $R^8$ are each independently a hydrogen or $C_1$–$C_4$ alkyl radical; or one of $CR^5$—$CR^6$, $CR^6$—$CR^7$ or $CR^7$—$CR^8$ is C=C;

wherein $R^9$ and $R^{10}$ are each independently -B-A, provided that the combined total number of aryl, heteroaryl, cycloalkyl and heterocyclyl radicals in $R^9$, $R^{10}$, $R^{11}$ and $R^{12}$ is 0–3;

wherein each B is independently a
(1) bond;
(2) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano or halo, and/or (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;
(3) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or
(4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_8$ haloalkyl of 1–3 halo radicals or $C_1$–$C_8$ haloalkoxy of 1–3 halo radicals;

each A is independently a
(1) hydrogen radical;
(2) halo, cyano or nitro radical;
(3) —C(O)—$R^{30}$, —C(O)—$OR^{31}$, —C(O)—$NR^{32}R^{31}$ or —C($NR^{32}$)—$NR^{32}R^{31}$ radical;
(4) —$OR^{31}$, —O—C(O)—$R^{31}$, —O—C(O)—$NR^{32}R^{31}$ or —O—C(O)—$NR^{33}$—S(O)$_2$—$R^{30}$ radical;
(5) —$SR^{31}$, —S(O)—$R^{30}$, —S(O)$_2$—$R^{30}$, —S(O)$_2$—$NR^{32}R^{31}$, —S(O)$_2$—$NR^{33}$—C(O)—$R^{31}$, —S(O)$_2$—$NR^{33}$—C(O)—$OR^{30}$ or —S(O)$_2$—$NR^{33}$—C(O)—$NR^{32}R^{31}$ radical; or
(6) —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R^{31}$ radical;

wherein each $R^{30}$ is independently
(1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

each $R^{31}$ is independently hydrogen radical or $R^{30}$;

wherein each $R^{32}$ is independently
(1) hydrogen radical;

(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; and each $R^{33}$ is independently (1) hydrogen radical;

(2) $C_1$–$C_4$ alkyl radical optionally substituted by a radical of heterocyclyl, aryl or heteroaryl which is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_3$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; or (3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; and each $R^{34}$ is independently hydrogen or $C_1$–$C_4$ alkyl, aryl, heteroaryl, aryl-$C_1$–$C_4$-alkyl or heteroaryl-$C_1$–$C_4$-alkyl radical, where in the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; and wherein cycloalkyl is a monocyclic, bicyclic or tricyclic carbocyclic alkyl radical of 3–10 ring members, which is optionally partially unsaturated or benzo-fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl, biphenyl or naphthyl radical; and heteroaryl is a radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein $R^1$ is (1) a $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —$OR^3$, —$SR^3$, —S(O)$R^3$, —S(O)$_2R^3$, —C(O)$R^3$, —$NR^3R^4$, aryl, heteroaryl, cycloalkyl or heterocyclyl; or (2) an aryl radical optionally substituted by a monocyclic heteroaryl or heterocyclyl radical of 5–6 ring members each of which is optionally substituted by a phenyl radical or monocyclic heteroaryl radical of 5–6 ring members; or (3) a heteroaryl radical optionally substituted by a phenyl or a monocyclic heteroaryl or heterocyclyl radical of 5–6 ring members each of which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —S(O)$R^3$, —S(O)$_2R^3$, —C(O)$R^3$, —$NR^3R^4$, amino, $C_1$–$C_4$ alkanoylamino, $C_1$–$C_4$ alkylsulfonylamino, $C_1$–$C_4$ alkoxycarbonylamino, $C_1$–$C_4$ alkoxycarbonyl, cyano, halo, azido, $C_1$–$C_6$ alkyl or $C_1$–$C_4$ haloalkyl of 1–3 halo radicals; provided that the total number of phenyl, aryl, heteroaryl, cycloalkyl and heterocyclyl radicals in $R^1$ is 0–3;

wherein each $R^3$ is independently a $C_1$–$C_4$ alkyl, $C_1$–$C_4$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals; and each $R^4$ is independently a hydrogen or $C_1$–$C_4$ alkyl radical;

V is —$CR^8R^{11}$— or —$CR^8R^{11}$—$CHR^{12}$—; wherein $R^{11}$ and $R^{12}$ are each independently (1) a hydrogen, —$OR^{20}$, —$SR^{21}$, —C(O)$R^{22}$, —$NR^{23}$—C(O)—$R^{31}$, —$NR^{33}$C(O)—$OR^{30}$, —$NR^{33}$—C(O)—$NR^{32}R^{31}$, —$NR^{33}$—S(O)$_2$—$R^{30}$, —$NR^{33}$—S(O)$_2$—$NR^{32}R^{31}$, cycloalkyl, aryl or heteroaryl radical; or (2) an $C_1$–$C_8$ alkyl, $C_2$–$C_8$ alkenyl or $C_2$–$C_8$ alkynyl radical optionally substituted with 1–3 radicals of —$OR^{20}$, —$SR^{21}$, —C(O)$R^{22}NR^{33}$C(O)—$R^{31}$, —$NR^{33}$—C(O)—$OR^{30}$, —$NR^{33}$—C(O)—$NR^{32}R^{31}$, —$NR^{33}$—S(O)$_2$—$R^{30}$, —$NR^{33}$—S(O)$_2$—$NR^{32}R^{31}$, aryl or heteroaryl; wherein the cycloalkyl, aryl and heteroaryl radicals of (1) and (2) are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

wherein each $R^{20}$ is independently a hydrogen, $C_1$–$C_4$ alkyl, $C_2$–$C_4$ alkenyl, aryl, heteroaryl, aryl-$C_1$–$C_4$-alkyl, heteroaryl-$C_1$–$C_4$-alkyl, $C_1$–$C_4$ alkanoyl, aroyl or heteroaroyl radical; wherein the alkyl and alkenyl radicals are optionally substituted by —C(O)$R^{22}$; and wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals; and each $R^{21}$ is independently a $C_1$–$C_4$ alkyl, $C_1$–$C_4$ alkyl-C(O)$R^{22}$, aryl, heteroaryl, aryl-$C_1$–$C_4$-alkyl or heteroaryl-$C_1$–$C_4$-alkyl radical; wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

wherein each $R^{22}$ is independently a hydroxy, $C_1$–$C_4$ alkoxy, aryloxy, aryl-$C_1$–$C_2$-alkoxy, heteroaryloxy, heteroaryl-$C_1$–$C_2$-alkoxy or —$NR^{23}R^{24}$ radical; wherein each $R^{23}$ is independently a hydrogen, $C_1$–$C_4$ alkyl, aryl, aryl-$C_1$–$C_2$-alkyl, heteroaryl or heteroaryl-$C_1$–$C_2$-alkyl radical; and each $R^{24}$ is independently a hydrogen or $C_1$–$C_4$ alkyl radical; or —$NR^{23}R^{24}$ represents a heterocyclyl or heteroaryl radical; wherein the heterocyclyl, aryl and heteroaryl radicals of $R^{22}$, $R^{23}$ and —$NR^{23}R^{24}$ are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals; and wherein each B is independently a
(1) bond;
(2) $C_1$–$C_8$ alkyl radical optionally substituted by (a) a radical of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;
(3) heterocyclyl radical; or
(4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;

wherein each $R^{30}$ is independently
(1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

each $R^{31}$ is independently hydrogen radical or $R^{30}$;

wherein each $R^{32}$ is independently hydrogen or $C_1$–$C_4$ alkyl radical;

each $R^{33}$ is independently hydrogen or $C_1$–$C_4$ alkyl radical; and each $R^{34}$ is independently hydrogen or $C_1$–$C_4$ alkyl radical.

4. The compound of claim 3 or a pharmaceutically acceptable salt thereof, wherein $R^1$ is (1) a $C_1$–$C_{12}$ alkyl radical optionally substituted by 1–3 radicals of —OH, —$OR^3$, —$SR^3$, —$S(O)R^3$, —$S(O)_2R^3$, —$C(O)R^3$, —$NR^3R^4$, aryl, heteroaryl, cycloalkyl or heterocyclyl; or (2) an aryl radical optionally substituted by a monocyclic heteroaryl or heterocyclyl radical of 5–6 ring members each of which is optionally substituted by a phenyl radical or monocyclic heteroaryl radical of 5–6 ring members; or (3) a heteroaryl radical optionally substituted by a phenyl or a monocyclic heteroaryl or heterocyclyl radical of 5–6 ring members each of which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)R^3$, —$S(O)_2R^3$, —$C(O)R^3$, —$NR^3R^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —$CF_3$ radicals; provided that the total number of phenyl, aryl, heteroaryl, cycloalkyl and heterocyclyl radicals in $R^1$ is 0–3;

wherein each $R^3$ is independently an $C_1$–$C_4$ alkyl, —$CF_3$, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —$CF_3$ or —$OCF_3$; and each $R^4$ is independently a hydrogen or methyl radical;

$R^2$ is a hydrogen or methyl radical;

V is —$CR^8R^{11}$— or —$CR^8R^{11}$—$CHR^{12}$—; wherein $R^{11}$ and $R^{12}$ are each independently (1) a hydrogen, —$OR^{20}$, —$SR^{21}$, —$C(O)R^{22}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_4$ alkyl, $C_2$–$C_4$ alkenyl or $C_2$–$C_4$ alkynyl radical optionally substituted with 1–3 radicals of —$OR^{20}$, —$SR^{21}$, —C(O)$R^{22}$, —$NR^{33}$—C(O)—$R^{31}$, —$NR^{33}$—C(O)—$OR^{30}$, —$NR^{33}$—C(O)—$NR^{32}R^{31}$, —$NR^{33}$—S(O)$_2$—$R^{30}$, —$NR^{33}$—S(O)$_2$—$NR^{32}R^{31}$, aryl or heteroaryl; wherein the cycloalkyl, aryl and heteroaryl radicals of (1) and (2) are optionally substituted by 1–3 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals;

wherein each $R^{20}$ is independently a hydrogen, $C_1$–$C_4$ alkyl, $C_2$–$C_4$ alkenyl, aryl, heteroaryl, aryl-$C_1$–$C_4$-alkyl, heteroaryl-$C_1$–$C_4$-alkyl, $C_1$–$C_4$ alkanoyl, aroyl or heteroaroyl radical; wherein the alkyl and alkenyl radicals are optionally substituted by —C(O)$R^{22}$; and wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals; and each $R^{21}$ is independently a $C_1$–$C_4$ alkyl, $C_1$–$C_4$ alkyl-C(O)$R^{22}$, aryl, heteroaryl, aryl-$C_1$–$C_4$-alkyl or heteroaryl-$C_1$–$C_4$-alkyl radical; wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals;

wherein each $R^{22}$ is independently a hydroxy, $C_1$–$C_4$ alkoxy, aryloxy, aryl-$C_1$–$C_2$-alkoxy, heteroaryloxy, heteroaryl-$C_1$–$C_2$-alkoxy or —$NR^{23}R^{24}$ radical; wherein each $R^{23}$ is independently a hydrogen, $C_1$–$C_4$ alkyl, aryl, aryl-$C_1$–$C_2$-alkyl, heteroaryl or heteroaryl-$C_1$–$C_2$-alkyl radical; and each $R^{24}$ is independently a hydrogen or $C_1$–$C_4$ alkyl radical; or —$NR^{23}R^{24}$ represents a heterocyclyl or heteroaryl radical; wherein the heterocyclyl, aryl and heteroaryl radicals of $R^{22}$, $R^{23}$ and —$NR^{23}R^{24}$ are optionally substituted by 1–3 radicals of hydroxy, $C_1$–$C_4$ alkoxy, $C_1$–$C_4$ alkylthiol, amino, acetylamino, methylsulfonylamino, methylsulfinyl, methylsulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals; and wherein each B is independently a
  (1) bond;
  (2) $C_1$–$C_8$ alkyl radical optionally substituted by (a) a radical of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;
  (3) heterocyclyl radical; or
  (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

each A is independently a
  (1) hydrogen radical;
  (2) halo, cyano or nitro radical;
  (3) —C(O)—$R^{30}$, —C(O)—$OR^{31}$, —C(O)—$NR^{32}R^{31}$ or —C($NR^{32}$)—$NR^{32}R^{31}$ radical;
  (4) —$OR^{31}$, —O—C(O)—$R^{31}$ or —O—C(O)—$NR^{32}R^{31}$ radical;
  (5) —$SR^{31}$, —S(O)—$R^{30}$, —S(O)$_2$—$R^{30}$ or —S(O)$_2$—$NR^{32}R^{31}$ radical; or
  (6) —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R$-radical;

wherein each $R^{30}$ is independently
  (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals;
  (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

each $R^{31}$ is independently hydrogen radical or $R^{30}$; and
each $R^{33}$ is independently a hydrogen or methyl radical.

5. The compound of claim 4 or a pharmaceutically acceptable salt thereof, wherein V is —$CR^8R^{11}$—; wherein $R^{11}$ is (1) a hydrogen, —$OR^{20}$, —$SR^{21}$, —C(O)$R^{22}$, —$NR^{33}$—C(O)—$R^{31}$, —$NR^{33}$—C(O)—$NR^{32}R^{31}$, —$NR^{33}$—S(O)$_2$—$NR^{32}R^{31}$, cycloalkyl, aryl or heteroaryl radical; or (2) an $C_1$–$C_4$ alkyl, $C_2$–$C_4$ alkenyl radical optionally substituted with 1–3 radicals of —$OR^{20}$, —$SR^{21}$, —C(O)$R^{22}$, —$NR^{33}$—C(O)—$OR^{30}$, —$NR^{33}$—C(O)—$NR^{32}R^{31}$, —$NR^{33}$—S(O)$_2$—$R^{30}$, —$NR^{33}$—S(O)$_2$—$NR^{32}R^{31}$, aryl or heteroaryl; wherein the cycloalkyl, aryl and heteroaryl radicals of (1) and (2) are optionally substituted by 1–2 radicals of hydroxy, $C_1$–$C_4$ alkoxy, $C_1$–$C_4$ alkylthiol, amino, acetylamino, methylsulfonylamino, methylsulfinyl, methysulfonyl, $C_1$–$C_4$ alkoxycarbonylamino, $C_1$–$C_4$ alkoxycarbonyl, cyano, halo, azido, $C_1$–$C_4$ alkyl, —$CF_3$ or —$OCF_3$ radicals.

6. The compound of claim 5 or a pharmaceutically acceptable salt thereof, wherein
$R^1$ is (1) an $C_1$–$C_{12}$ alkyl radical optionally substituted by 1–3 radicals of —OH, —$OR^3$, —$SR^3$, —$S(O)_2R^3$, —$NR^3R^4$, aryl, heteroaryl, cycloalkyl or heterocyclyl; or (2) an aryl radical optionally substituted by a monocyclic heteroaryl or heterocyclyl radical of 5–6 ring members each of which is optionally substituted by a phenyl radical or monocyclic heteroaryl radical of 5–6 ring members; or (3) a heteroaryl radical optionally substituted by a phenyl or a monocyclic heteroaryl or heterocyclyl radical of 5–6 ring members each of which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)_2R^3$, —$NR^3R^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —$CF_3$ radicals; provided that the total number of phenyl, aryl, heteroaryl, cycloalkyl and heterocyclyl radicals in $R^1$ is 0–2;

wherein each $R^3$ is independently a $C_1$–$C_4$ alkyl, —$CF_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —$CF_3$ or —$OCF_3$;

$R^2$ is a hydrogen radical;

V is —$CR^8R^{11}$—; wherein $R^{11}$ is (1) a hydrogen, —$OR^{20}$, —$SR^{21}$, —$C(O)R^{22}$, —$NR^{33}13$ $C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, cycloalkyl, aryl or heteroaryl radical; or (2) an $C_1$–$C_4$ alkyl or $C_2$–$C_4$ alkenyl radical optionally substituted with 1–3 radicals of —$OR^{20}$, —$SR^{21}$, —$C(O)R^{22}$, —$NR^{33}$—$C(O)$—$R^{31}$, —$NR^{33}C(O)$—$OR^{30}$, —$NR^{33}$—$C(O)$—$NR^{32}R^{31}$, —$NR^{33}$—$S(O)_2$—$R^{30}$, —$NR^{33}$—$S(O)_2$—$NR^{32}R^{31}$, aryl or heteroaryl; wherein the cycloalkyl, aryl and heteroaryl radicals of (1) and (2) are optionally substituted by 1–2 radicals of hydroxy, $C_1$–$C_4$ alkoxy, $C_1$–$C_4$ alkylthiol, methylsulfonyl, halo, azido, $C_1$–$C_4$ alkyl, —$CF_3$ or —$OCF_3$ radicals;

wherein each $R^{22}$ is independently a hydroxy, $C_1$–$C_4$ alkoxy, aryloxy, aryl-$C_1$–$C_2$-alkoxy, heteroaryloxy, heteroaryl-$C_1$–$C_2$-alkoxy or —$NR^{23}R^{24}$ radical; wherein each $R^{23}$ is independently a hydrogen, $C_1$–$C_4$ alkyl, aryl, aryl-$C_1$–$C_2$-alkyl, heteroaryl or heteroaryl-$C_1$–$C_2$-alkyl radical; and each $R^{24}$ is independently a hydrogen or $C_1$–$C_4$ alkyl radical; or —$NR^{23}R^{24}$ represents a heterocyclyl or heteroaryl radical; wherein the heterocyclyl, aryl and heteroaryl radicals of $R^{22}$, $R^{23}$ and —$NR^{23}R^{24}$ are optionally substituted by 1–2 radicals of hydroxy, $C_1$–$C_4$ alkoxy, $C_1$–$C_4$ alkylthiol, halo, azido, $C_1$–$C_4$ alkyl, —$CF_3$ or —$OCF_3$ radicals; and wherein each B is independently a
(1) bond;
(2) $C_1$–$C_4$ alkyl radical optionally substituted by (a) a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, hydroxy, $C_1$–$C_2$ alkoxy, and/or (b) 1–2 halo radicals, and/or (c) a radical of heterocyclyl, aryl or heteroaryl optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $c_1$–$C_2$ alkoxy, $C_1$–$C_2$ alkylthio, halo, $C_1$–$C_4$ alkyl, —$CF_3$ or —$OCF_3$ radicals;

(3) heterocyclyl radical; or
(4) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

each A is independently a
(1) hydrogen radical;
(2) halo radical;
(3) —$C(O)$—$R^{30}$, —$C(O)$—$OR^{31}$, —$C(O)$—$NR^{32}R^{31}$ or —$C(NR^{32})$—$NR^{32}R^{31}$ radical;
(4) —$OR^{31}$ radical;
(5) —$SR^{31}$, —$S(O)_2$—$R^{30}$ or —$S(O)_2$—$NR^{32}R^{31}$ radical; or
(6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{-S(O)_2}$—$R^{30}$ or —$NR^{33}$—$S(O)_2$—$NR^{32}R^{31}$ radical;

wherein each $R^{30}$ is independently
(1) —$CF_3$ or $C_1$–$C_4$ alkyl radical optionally substituted by 1–2 radicals of —$CO_2R^{34}$, amino, $C_1$–$C_2$ alkylamino, di-($C_1$–$C_2$ alkyl)amino, $C_1$–$C_2$ alkanoylamino, ($C_1$–$C_4$ alkoxy)carbonylamino, N-(($C_1$–$C_4$ alkoxy)carbonyl)-N-($C_1$–$C_4$ alkyl) amino, hydroxy, $C_1$–$C_4$ alkoxy, or aryl-$C_1$–$C_2$-alkoxy, heterocyclyl, aryl or heteroaryl radicals, wherein the heterocyclyl, aryl and heteroaryl radicals are optionally substituted by 1–3 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —$CF_3$ or —$OCF_3$ radicals;
(2) heterocyclyl radical optionally substituted by 1–2 radicals of ($C_1$–$C_4$ alkoxy)carbonyl, hydroxy or $C_1$–$C_4$ alkyl; or
(3) aryl or heteroaryl radicals optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —$CF_3$ or —$OCF_3$ radicals;

each $R^{31}$ is independently hydrogen radical or $R^{30}$; and wherein cycloalkyl is a monocyclic carbocyclic alkyl radical of 3–6 ring members, which is optionally partially unsaturated or benzo-fused; and heterocyclyl is a radical of a monocyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals.

7. The compound of claim 6 or a pharmaceutically acceptable salt thereof, wherein
$R^1$ is (1) an $C_1$–$C_4$ alkyl radical substituted by 1–2 radicals of —OH, —$OR^3$, —$NR^3R^4$, aryl or heteroaryl; or (2) an aryl radical optionally substituted by a monocyclic heteroaryl radical of 5–6 ring members; or (3) a heteroaryl radical optionally substituted by a phenyl radical; wherein the phenyl, aryl and heteroaryl radicals of (1), (2) and (3) are optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals; provided that the total number of phenyl, aryl and heteroaryl radicals in R$^1$ is 0–2;

wherein each R$^3$ is independently a $C_1$–$C_4$ alkyl, —CF$_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_2$ alkoxy, $C_1$–$C_2$ alkylthiol, amino, acetylamino, methylsulfonylamino, $C_1$–$C_2$ alkylsulfonyl, $C_1$–$C_4$ alkoxycarbonylamino, $C_1$–$C_4$ alkoxycarbonyl, halo, $C_1$–$C_2$ alkyl, —CF$_3$ or —OCF$_3$;

V is —CR$^8$R$^{11}$—; wherein R$^{11}$ is (1) a hydrogen, —OR$^{20}$, —NR$^{33}$—C(O)—R$^{31}$, —NR$^{33}$—S(O)$_2$—R$^{30}$, cycloalkyl, aryl or heteroaryl radical; or (2) an $C_1$–$C_4$ alkyl or $C_2$–$C_4$ alkenyl radical optionally substituted with 1–2 radicals of —OR$^{20}$, —SR$^{21}$, —C(O)R$^{22}$, —NR$^{33}$—C(O)—R$^{31}$, —NR$^{33}$—S(O)$_2$—R$^{30}$, aryl or heteroaryl; wherein the cycloalkyl, aryl and heteroaryl radicals of (1) and (2) are optionally substituted by 1–2 radicals of hydroxy, $C_1$–$C_2$ alkoxy, $C_1$–$C_2$ alkylthiol, halo, azido, $C_1$–$C_2$ alkyl, —CF$_3$ or —OCF$_3$ radicals;

wherein each R$^{20}$ is independently a hydrogen, $C_1$–$C_4$ alkyl, $C_1$–$C_4$ alkyl-C(O)R$^{22}$, $C_2$–$C_4$ alkenyl, aryl, heteroaryl, aryl-$C_1$–$C_2$-alkyl, heteroaryl-$C_1$–$C_2$-alkyl or $C_1$–$C_4$ alkanoyl radical; and wherein the aryl and heteroaryl radicals are optionally substituted by 1–2 radicals of hydroxy, $C_1$–$C_4$ alkoxy, $C_1$–$C_4$ alkylthiol, halo, azido, $C_1$–$C_2$ alkyl, —CF$_3$ or —OCF$_3$ radicals; and each R$^{21}$ is independently a $C_1$–$C_4$ alkyl, $C_1$–$C_4$ alkyl-C(O)R$^{22}$, aryl, heteroaryl, aryl-$C_1$–$C_2$-alkyl or heteroaryl-$C_1$–$C_2$-alkyl radical; wherein the aryl and heteroaryl radicals are optionally substituted by 1–2 radicals of hydroxy, $C_1$–$C_4$ alkoxy, $C_1$–$C_4$ alkylthiol, halo, azido, $C_1$–$C_2$ alkyl, —CF$_3$ or —OCF$_3$ radicals;

wherein each R$^{22}$ is independently a hydroxy or —NR$^{23}$R$^{24}$ radical; wherein each R$^{23}$ is independently a hydrogen, $C_1$–$C_2$ alkyl, aryl, aryl-$C_1$–$C_2$-alkyl, heteroaryl or heteroaryl-$C_1$–$C_2$-alkyl radical; and each R$^{24}$ is independently a hydrogen or $C_1$–$C_2$ alkyl radical; or —NR$^{23}$R$^{24}$ represents a heteroaryl radical; wherein the aryl and heteroaryl radicals of R$^{22}$, R$^{23}$ and —NR$^{23}$R$^{24}$ are optionally substituted by 1–2 radicals of hydroxy, $C_1$–$C_2$ alkoxy, $C_1$–$C_2$ alkylthiol, halo, azido, $C_1$–$C_2$ alkyl, —CF$_3$ or —OCF$_3$ radicals; and wherein each B is independently a
(1) bond;
(2) $C_1$–$C_4$ alkyl radical; or
(3) aryl or heteroaryl radical optionally substituted by a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —CF$_3$ or —OCF$_3$ radicals;

each A is independently a
(1) hydrogen radical;
(2) halo radical;
(3) —C(O)—R$^{30}$, —C(O)—NR$^{32}$R$^{31}$ or —C(NR$^{32}$)—NR$^{32}$R$^{31}$ radical;

(4) —OR$^{31}$ radical;
(5) —SR$^{31}$, —S(O)$_2$—R$^{30}$ or —S(O)$_2$—NR$^{32}$R$^{31}$ radical; or
(6) —NR$^{32}$R$^{31}$, —NR$^{33}$—C(O)—R$^{31}$ or —NR$^{33}$—S(O)$_2$—R$^{30}$ radical;

wherein each R$^{30}$ is independently
(1) heterocyclyl radical optionally substituted by 1–2 radicals of ($C_1$–$C_4$ alkoxy)carbonyl, hydroxy or $C_1$–$C_4$ alkyl; or
(2) heteroaryl radicals optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —CF$_3$ or —OCF$_3$ radicals; and each R$^{31}$ is independently hydrogen radical or
(1) —CF$_3$ or $C_1$–$C_4$ alkyl radical optionally substituted by 1–2 radicals of hydroxy, $C_1$–$C_2$ alkoxy or aryl-$C_1$–$C_2$-alkoxy, aryl or heteroaryl radicals, wherein the aryl and heteroaryl radicals are optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —CF$_3$ or —OCF$_3$ radicals; or
(2) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —CF$_3$ or —OCF$_3$ radicals.

8. The compound of claim 7 or a pharmaceutically acceptable salt thereof, wherein R$^1$ is aryl or heteroaryl radicals optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals; provided that the total number of aryl and heteroaryl radicals in R$^1$ is 1–2;

wherein each R$^3$ is independently a $C_1$–$C_4$ alkyl, —CF$_3$, aryl, heteroaryl, arylmethyl or heteroarylmethyl radical;

V is —CR$^8$R$^{11}$—; wherein R$^{11}$ is (1) a hydrogen, —OR$^{20}$, —NR$^{33}$—C(O)—R$^{31}$, —NR$^{33}$—S(O)$_2$—R$^{30}$, cycloalkyl, aryl or heteroaryl radical; or (2) an $C_1$–$C_4$ alkyl or $C_2$–$C_4$ alkenyl radical optionally substituted with 1–2 radicals of —OR$^{20}$, —NR$^{33}$—C(O)—R$^{31}$, —NR$^{33}$—S(O)$_2$—R$^{30}$, aryl or heteroaryl; wherein the cycloalkyl, aryl and heteroaryl radicals of (1) and (2) are optionally substituted by 1–2 radicals of hydroxy, $C_1$–$C_2$ alkoxy, $C_1$–$C_2$ alkylthiol, halo, azido, $C_1$–$C_2$ alkyl, —CF$_3$ or —OCF$_3$ radicals;

wherein each R$^{20}$ is independently a hydrogen, $C_1$–$C_4$ alkyl, $C_2$–$C_4$ alkenyl, aryl, heteroaryl, aryl-$C_1$–$C_2$-alkyl, heteroaryl-$C_1$–$C_2$-alkyl or $C_1$–$C_4$ alkanoyl radical; and wherein each B is independently a
(1) bond;
(2) $C_1$–$C_4$ alkyl radical; or
(3) aryl or heteroaryl radical;

each A is independently a
(1) hydrogen radical;
(2) halo radical; or
(3) —C(O)—R$^{30}$ or —C(O)—NR$^{32}$R$^{31}$ radical;

wherein each R$^{30}$ is independently a heterocyclyl radical optionally substituted by $C_1$–$C_4$ alkyl;

each R$^{31}$ is independently hydrogen radical or (1) —CF$_3$ or C$_1$–C$_4$ alkyl radical optionally substituted by 1–2 radicals of aryl or heteroaryl radicals; or
(2) aryl or heteroaryl radical; and wherein each R$^{32}$ is independently a hydrogen or methyl radical.

9. The compound of claim 8 or a pharmaceutically acceptable salt thereof, wherein R$^1$ is an aryl radical optionally substituted by 1–2 radicals of hydroxy, —OR$^3$, —S(O)$_2$R$^3$, —NR$^3$R$^4$, amino, acetylamino, methylsulfonylamino, halo, C$_1$–C$_4$ alkyl or —CF$_3$ radicals; provided that the total number of aryl and heteroaryl radicals in R$^1$ is 1–2;

V is —CR$^8$R$^{11}$—; wherein R$^{11}$ is (1) a hydrogen, —OR$^{20}$, aryl or heteroaryl radical; or (2) an C$_1$–C$_4$ alkyl or C$_2$–C$_4$ alkenyl radical optionally substituted with 1–2 radicals of —OR$^{20}$, aryl or heteroaryl; wherein the aryl and heteroaryl radicals of (1) and (2) are optionally substituted by 1–2 radicals of hydroxy, C$_1$–C$_2$ alkoxy, halo, C$_1$–C$_2$ alkyl, —CF$_3$ or —OCF$_3$ radicals; provided the total number of aryl and heteroaryl radicals in R$^{11}$ is 0–2;

R$^5$, R$^6$, R$^7$, R$^8$, R$^9$ and R$^{10}$ are each a hydrogen radical; or one of CR$^5$—CR$^6$, CR$^6$—CR$^7$ or CR$^7$—CR$^8$ is C=C; and wherein heterocyclyl is a radical of pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl or its sulfoxide or sulfone derivative, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl or ethylenedioxyphenyl; aryl is a phenyl, biphenyl or naphthyl radical; and heteroaryl is a radical of imidazolyl, pyrrolyl, pyrazolyl, pyridyl, pyrazinyl, triazolyl, furyl, thienyl, oxazolyl, thiazolyl, indolyl, quinolinyl, isoquinolinyl, 5,6,7,8-tetrahydroquinolyl, 5,6,7,8-tetrahydroisoquinolinyl, quinoxalinyl, benzothiazolyl, β-carbolinyl, benzofuryl, benzimidazolyl or benzoxazolyl.

10. The compound of claim 9 or a pharmaceutically acceptable salt thereof, wherein R$^1$ is an phenyl radical optionally substituted by 1–2 radicals of hydroxy, —OR$^3$, —S(O)$_2$R$^3$, —NR$^3$R$^4$, amino, acetylamino, methylsulfonylamino, halo, C$_1$–C$_4$ alkyl or —CF$_3$ radicals; provided that the total number of aryl and heteroaryl radicals in R$^1$ is 1–2;

wherein each R$^3$ is independently an C$_1$–C$_4$ alkyl, —CF$_3$, phenyl, heteroaryl, phenylmethyl or heteroarylmethyl radical;

V is —CR$^8$R$^{11}$—; wherein R$^{11}$ is (1) a hydrogen, —OR$^{20}$, phenyl or heteroaryl radical; or (2) an C$_1$–C$_4$ alkyl or C$_2$–C$_4$ alkenyl radical optionally substituted with 1–2 radicals of —OR$^{20}$, phenyl or heteroaryl; wherein the phenyl and heteroaryl radicals of (1) and (2) are optionally substituted by 1–2 radicals of hydroxy, C$_1$–C$_2$ alkoxy, halo, C$_1$–C$_2$ alkyl, —CF$_3$ or —OCF$_3$ radicals; provided the total number of aryl and heteroaryl radicals in R$^{11}$ is 0–2;

wherein each R$^{20}$ is independently a hydrogen, C$_1$–C$_4$ alkyl, C$_2$–C$_4$ alkenyl, phenyl, heteroaryl, phenyl-C$_1$–C$_2$-alkyl, heteroaryl-C$_1$–C$_2$-alkyl or radical; and wherein heterocyclyl is a radical of pyrrolidinyl, piperidinyl, piperazinyl, morpholinyl, thiamorpholinyl, 4-benzyl-piperazin-1-yl or pyrimidinyl; and heteroaryl is a radical of imidazolyl, pyrrolyl, pyrazolyl, pyridyl, pyrazinyl, indolyl, quinolinyl, isoquinolinyl, benzothiazolyl, benzofuryl, benzimidazolyl or benzoxazolyl.

11. The compound of claim 10 or a pharmaceutically acceptable salt thereof, wherein R$^1$ is an phenyl radical optionally substituted by 1–2 radicals of hydroxy, —OR$^3$, halo, methyl or —CF$_3$ radicals; provided that the total number of aryl and heteroaryl radicals in R$^1$ is 1–2;

wherein each R$^3$ is independently an methyl, —CF$_3$, phenyl, heteroaryl, phenylmethyl or heteroarylmethyl radical;

V is —CR$^8$R$^{11}$—; wherein R$^{11}$ is (1) a hydrogen, —OR$^{20}$, phenyl or heteroaryl radical; or (2) an C$_1$–C$_4$ alkyl or C$_2$–C$_4$ alkenyl radical optionally substituted with 1–2 radicals of —OR$^{20}$, phenyl or heteroaryl; wherein the phenyl and heteroaryl radicals of (1) and (2) are optionally substituted by 1–2 radicals of hydroxy, methoxy, halo, methyl, —CF$_3$ or —OCF$_3$ radicals; provided the total number of aryl and heteroaryl radicals in R$^{11}$ is 0–2; and wherein each R$^{20}$ is independently a hydrogen, methyl, propenyl, phenyl, heteroaryl, phenyl-C$_1$–C$_2$-alkyl or heteroaryl-C$_1$–C$_2$-alkyl radical.

12. The compound of claim 1 or a pharmaceutically acceptable salt thereof, which is cis-3-benzyl-1-(4-methoxyphenylsulfonyl)-azepane-2-hydroxamic acid;

trans-3-benzyl-1-(4-methoxyphenylsulfonyl)-azepane-2-hydroxamic acid;

trans-3-phenyl-1-(4-methoxyphenylsulfonyl)-azepane-2-hydroxamic acid;

1-(4-methoxyphenylsulfonyl)-azepane-2-hydroxamic acid;

acetic acid (2-hydroxycarbamoyl-1-(4-methoxyphenylsulfonyl)-azepan-3-yl)methyl ester;

3-hydroxymethyl-1-(4-methoxyphenylsulfonyl)-azepane-2-hydroxamic acid;

3-benzyloxymethyl-1-(4-methoxyphenylsulfonyl)-azepane-2-hydroxamic acid;

1-(4-methoxyphenylsulfonyl)-3-phenylsulfanylmethyl-azepane-2-hydroxamic acid;

1-(4-methoxyphenylsulfonyl)-3-styryl-azepane-2-hydroxamic acid;

3-(2-hydroxycarbamoyl-1-(4-methoxyphenylsulfonyl)-azepan-3-yl)acrylic acid;

acetic acid (2-hydroxycarbamoyl-1-(4-methoxyphenylsulfonyl)-2,3,4,7-tetrahydro-1H-azepin-3-yl)methyl ester;

3-hydroxymethyl-1-(4-methoxyphenylsulfonyl)-2,3,4,7-tetrahydro-1H-azepine-2-hydroxamic acid;

3-benzyloxymethyl-1-(4-methoxyphenylsulfonyl)-2,3,4,7-tetrahydro-1H-azepine-2-hydroxamic acid;

1-(4-methoxyphenylsulfonyl)-3-phenylsulfanylmethyl-2,3,4,7-tetrahydro-1H-azepine-2-hydroxamic acid;

3-benzofuran-2-yl-1-(4-methoxyphenylsulfonyl)-2,3,4,7-tetrahydro-1H-azepine-2-hydroxamic acid;

1-(4-methoxyphenylsulfonyl)-azepane-2,3-dicarboxylic acid 2-(hydroxamide) 3-(phenmethylamide);

1-(4-methoxyphenylsulfonyl)-azepane-2,3-dicarboxylic acid 2-(hydroxamide) 3-(phenethylamide);

1-(4-methoxyphenylsulfonyl)-azepane-2,3-dicarboxylic acid 2-(hydroxamide) 3-(phenpropylamide);

1-(4-methoxyphenylsulfonyl)-azepane-2,3-dicarboxylic acid 2-(hydroxamide) 3-(4-phenoxy-2-ethylamide);

1-(4-methoxyphenylsulfonyl)-azepane-2,3-dicarboxylic acid 2-(hydroxamide) 3-(phenylmethylsulfanylethylamide);

1-(4-methoxyphenylsulfonyl)-azepane-2,3-dicarboxylic acid 2-(hydroxamide) 3-(4-Phenoxyphenethylamide);

Cis-3-(4-Phenylbenzyl)-1-(4-methoxyphenylsulfonyl)-azepane-2-hydroxamic acid;

Trans-3-(4-Phenylbenzyl)-1-(4-methoxyphenylsulfonyl)-azepane-2-hydroxamic acid;

Trans-3-Methyl-1-(4-methoxyphenylsulfonyl)-azepane-2-hydroxamic acid; or (2-Hydroxycarbamoyl-1-(4-methoxyphenylsulfonyl)-2,3,4,7-tetrahydro-1H-azepine-3-yl)-carbamic acid benzyl ester.

13. A pharmaceutical composition comprising a compound of according to any of claims 1–12 and a pharmaceutically acceptable carrier.

14. A method for prophylaxis or treatment of inflammation comprising administering an effective amount of a compound of according to any of claims 1–12.

15. A method for prophylaxis or treatment of inflammation comprising administering an effective amount of a composition of claim 13.

16. A method for prophylaxis or treatment of connective tissue degradation comprising administering an effective amount of a compound of according to any of claims 1–12.

17. A method for prophylaxis or treatment of connective tissue degradation comprising administering an effective amount of a composition of claim 13.

18. A method of treating rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; HIV infections; cytomegalovirus (CMV) infections; influenza; adenovirus infections; the herpesvirus infections; herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; or fever or mylagias due to infection comprising administering an effective amount of a compound of according to any of claims 1–12.

19. A method of treating rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; HIV infections; cytomegalovirus (CMV) infections; influenza; adenovirus infections; the herpesvirus infections; herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; or fever or mylagias due to infection comprising administering an effective amount of a composition of claim 13.

20. A method of lowering plasma concentrations of TNF-$\alpha$ comprising administering an effective amount of a compound of according to any of claims 1–12.

21. A method of lowering plasma concentrations of TNF-$\alpha$ comprising administering an effective amount of a composition of claim 13.

22. A method of treating neuroinflammatory disorders or angiogenesis dependent diseases comprising administering an effective amount of a compound of according to any of claims 1–12.

23. A method of treating neuroinflammatory disorders or angiogenesis dependent diseases comprising administering an effective amount of a composition of claim 13.

24. A method of treating rheumatoid arthritis, osteoarthritis, osteopenias, periodontitis, gingivitis, corneal ulceration, epidermal ulceration, gastric ulceration, tumour metastasis, tumour invasion, tumour growth, myelin degradation, cancer, psoriasis, proliferative retinopathies, neovascular glaucoma, ocular tumours, angiofibromas, hemangiomas, nephritis, pulmonary inflammation or restenosis comprising administering an effective amount of a compound of according to any of claims 1–12.

25. A method of treating rheumatoid arthritis, osteoarthritis, osteopenias, periodontitis, gingivitis, corneal ulceration, epidermal ulceration, gastric ulceration, tumour metastasis, tumour invasion, tumour growth, myelin degradation, cancer, psoriasis, proliferative retinopathies, neovascular glaucoma, ocular tumours, angiofibromas, hemangiomas, nephritis, pulmonary inflammation or restenosis comprising administering an effective amount of a composition of claim 13.

* * * * *

UNITED STATES PATENT AND TRADEMARK OFFICE
CERTIFICATE OF CORRECTION

PATENT NO. : 6,107,291
DATED : August 22, 2000
INVENTOR(S) : Russo-Rodriguez et al.

It is certified that error appears in the above-identified patent and that said Letters Patent is hereby corrected as shown below:

Column 3,
Line 48, change "—$SR_3$," to -- —$SR^3$, --.

Column 14,
Line 7, change "—C(O))" to -- —C(O) --.

Column 15,
Line 47, change "$CO_2R^{34}$" to -- —$CO_2R^{34}$ --.

Column 21,
Line 60, change "ore" to -- more --.
Line 61, change "referable" to -- preferably --.

Column 39,
Line 65, change "azeiane" to -- azepane --.

Column 42,
Line 24, change "azeoane" to -- azepane --.

Column 43,
Line 57, change "azenane" to -- azepane --.

Column 46,
Lines 1-10, change

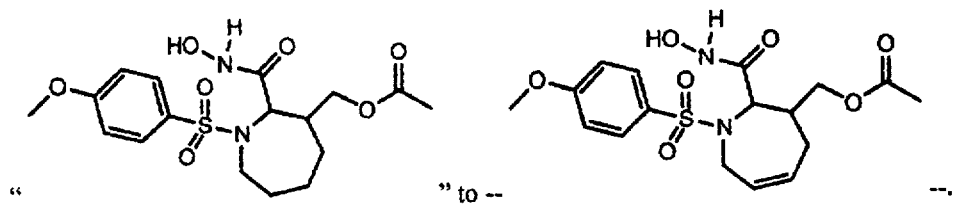

" to -- --.

UNITED STATES PATENT AND TRADEMARK OFFICE
CERTIFICATE OF CORRECTION

PATENT NO. : 6,107,291
DATED : August 22, 2000
INVENTOR(S) : Russo-Rodriguez et al.

It is certified that error appears in the above-identified patent and that said Letters Patent is hereby corrected as shown below:

Column 48,
Lines 20-30, change

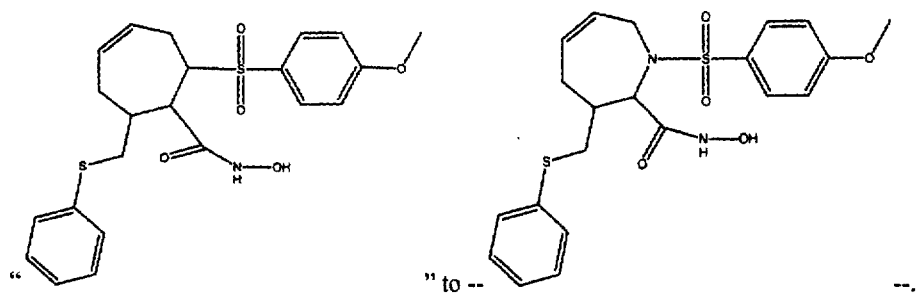

Column 49,
Line 67, change "(M-H)$^{30}$ 426" to -- (M-H)$^+$ 426 --.

Column 52,
Line 1, change "LiOH.H$_2$O" to -- LiOH•H$_2$O --.

Column 56,
Lines 5-15, change

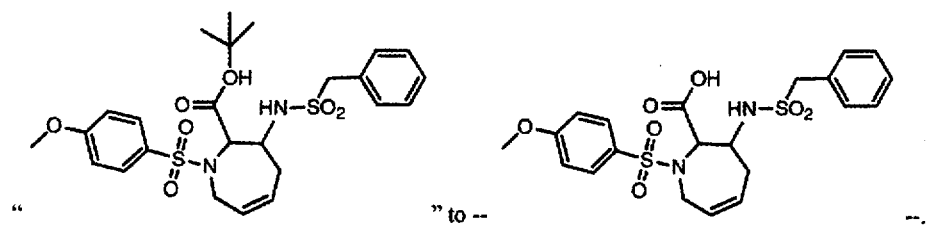

Column 58,
Line 47, change "7-Benzhvdryloxy" to -- 7-Benzhydryloxy --.

UNITED STATES PATENT AND TRADEMARK OFFICE
CERTIFICATE OF CORRECTION

PATENT NO. : 6,107,291
DATED : August 22, 2000
INVENTOR(S) : Russo-Rodriguez et al.

It is certified that error appears in the above-identified patent and that said Letters Patent is hereby corrected as shown below:

Column 60,
Line 9, change "(4-Phenoxylphenethylamide):" to -- (4-Phenoxyphenethylamide): --.

Column 68,
Line 30, change "1-propylNH—" to -- i-propylNH— --.

Column 71,
Line 61, change "BtO—C(O) —" to -- EtO—C(O) — --.

Column 76,
Lines 57-58, change "polynomnial" to -- polynomial --.

Column 84,
Line 64, change "—C($NR^{32}$)—$NR^{32}R$ radical" to -- —C($NR^{32}$)—$NR^{32}R^{31}$ radical --.

Column 85,
Line 2, change "—S(O)$_2R^{33}$—C(O) —$R^{31}$," to -- —S(O)$_2NR^{33}$—C(O) —$R^{31}$, --.

Column 90,
Line 34, change "—$NR^{23}$—C(O) —$R^{31}$," to -- —$NR^{33}$—C(O) —$R^{31}$, --.

Column 94,
Line 17, change "—$NR^{32}R^{radical}$" to -- —$NR^{32}R^{31}$ radical --.
Lines 59-60, change "—$NR^{33}$—C(O) —$NR^{32}R^{31}$, —$NR^{33}$—S(O)$_2$—$NR^{32}R^{31}$," to -- —$NR^{33}$—C(O) —$OR^{30}$, —$NR^{33}$—C(O)—$NR^{32}R^{31}$, —$NR^{33}$—S(O)$_2$—$R^{30}$, —$NR^{33}$—S(O)$_2$—$NR^{32}R^{31}$, --.
Line 64, change "—$NR^{33}$—C(O) —$OR^{30}$," to -- —$NR^{33}$—C(O) —$OR^{31}$, —$NR^{33}$—C(O)—$OR^{30}$, --.

Column 95,
Line 39, change "—$NR^{33}13C(O)$—$R^{31}$," to -- —$NR^{33}$—C(O)—$OR^{31}$, --.

UNITED STATES PATENT AND TRADEMARK OFFICE
CERTIFICATE OF CORRECTION

PATENT NO. : 6,107,291
DATED : August 22, 2000
INVENTOR(S) : Russo-Rodriguez et al.

It is certified that error appears in the above-identified patent and that said Letters Patent is hereby corrected as shown below:

<u>Column 96,</u>
Lines 27-28, change "—NR$^{S(O)}{}_2$—R$^{30}$," to -- —NR$^{33}$—S(O)$_2$—R$^{30}$, --.

Signed and Sealed this

Seventh Day of May, 2002

*Attest:*

*Attesting Officer*

JAMES E. ROGAN
*Director of the United States Patent and Trademark Office*